(12) United States Patent
Lee et al.

(10) Patent No.: US 7,547,779 B2
(45) Date of Patent: Jun. 16, 2009

(54) PREPARATION OF 1,6-DISUBSTITUTED AZABENZIMIDAZOLES AS KINASE INHIBITORS

(75) Inventors: Dennis Lee, King of Prussia, PA (US); Robert A. Stavenger, King of Prussia, PA (US); Krista B. Goodman, King of Prussia, PA (US); Mark A. Hilfiker, King of Prussia, PA (US); Haifeng Cui, King of Prussia, PA (US); Andrew Q. Viet, King of Prussia, PA (US); Joseph P. Marino, King of Prussia, PA (US)

(73) Assignee: Glaxo Group Limited, Greenford, Middlesex (GB)

( * ) Notice: Subject to any disclaimer, the term of this patent is extended or adjusted under 35 U.S.C. 154(b) by 443 days.

(21) Appl. No.: 10/574,676

(22) PCT Filed: Oct. 6, 2004

(86) PCT No.: PCT/US2004/032824

§ 371 (c)(1),
(2), (4) Date: Apr. 4, 2006

(87) PCT Pub. No.: WO2005/037197

PCT Pub. Date: Apr. 28, 2005

(65) Prior Publication Data

US 2008/0234261 A1 Sep. 25, 2008

Related U.S. Application Data

(60) Provisional application No. 60/508,894, filed on Oct. 6, 2003, provisional application No. 60/531,949, filed on Dec. 23, 2003.

(51) Int. Cl.
*C07D 413/00* (2006.01)
*C07D 401/00* (2006.01)
*C07D 471/02* (2006.01)
*C07D 491/02* (2006.01)

(52) U.S. Cl. .......................... 544/127; 544/362; 546/118

(58) Field of Classification Search ................. 546/118; 514/303, 234.2, 253.04; 544/127, 362
See application file for complete search history.

(56) References Cited

U.S. PATENT DOCUMENTS

2003/0125344 A1 7/2003 Nagarathnam et al.

FOREIGN PATENT DOCUMENTS

| DE | 3722992 A2 | 1/1989 |
| WO | 03080610 | * 10/2003 |
| WO | WO03080610 A1 | 10/2003 |

OTHER PUBLICATIONS

Takemoto et al., Circulation, (Jul. 2, 2002) vol. 106, No. 1, pp. 57-62.*

* cited by examiner

*Primary Examiner*—D. Margaret Seaman
*Assistant Examiner*—Niloofar Rahmani
(74) *Attorney, Agent, or Firm*—Reid S. Willis; John Lemanowicz

(57) ABSTRACT

Novel inhibitors of Rho-kinases are disclosed.

2 Claims, No Drawings

PREPARATION OF 1,6-DISUBSTITUTED AZABENZIMIDAZOLES AS KINASE INHIBITORS

This application is a 371 of International Application Number PCT/US04/032824 filed 6 Oct. 2004, which claims priority to 60/508,894 filed 6 Oct. 2003 and 60/531,949 filed 23 Dec. 2003.

An important large family of enzymes is the protein kinase enzyme family. Currently, there are about 500 different known protein kinases. Protein kinases serve to catalyze the phosphorylation of an amino acid side chain in various proteins by the transfer of the γ-phosphate of the ATP-Mg$^{2+}$ complex to said amino acid side chain. These enzymes control the majority of the signaling processes inside cells, thereby governing cell function, growth, differentiation and destruction (apoptosis) through reversible phosphorylation of the hydroxyl groups of serine, threonine and tyrosine residues in proteins. Studies have shown that protein kinases are key regulators of many cell functions, including signal transduction, transcriptional regulation, cell motility, and cell division. Several oncogenes have also been shown to encode protein kinases, suggesting that kinases play a role in oncogenesis. These processes are highly regulated, often by complex intermeshed pathways where each kinase will itself be regulated by one or more kinases. Consequently, aberrant or inappropriate protein kinase activity can contribute to the rise of disease states associated with such aberrant kinase activity. Due to their physiological relevance, variety and ubiquitousness, protein kinases have become one of the most important and widely studied family of enzymes in biochemical and medical research.

The protein kinase family of enzymes is typically classified into two main subfamilies: Protein Tyrosine Kinases and Protein Serine/Threonine Kinases, based on the amino acid residue they phosphorylate. The serine/threonine kinases (PSTK), includes cyclic AMP- and cyclic GMP-dependent protein kinases, calcium- and phospholipid-dependent protein kinase, calcium- and calmodulin-dependent protein kinases, casein kinases, cell division cycle protein kinases and others. These kinases are usually cytoplasmic or associated with the particulate fractions of cells, possibly by anchoring proteins. Aberrant protein serine/threonine kinase activity has been implicated or is suspected in a number of pathologies such as rheumatoid arthritis, psoriasis, septic shock, bone loss, many cancers and other proliferative diseases. Accordingly, serine/threonine kinases and the signal transduction pathways which they are part of are important targets for drug design. The tyrosine kinases phosphorylate tyrosine residues. Tyrosine kinases play an equally important role in cell regulation. These kinases include several receptors for molecules such as growth factors and hormones, including epidermal growth factor receptor, insulin receptor, platelet derived growth factor receptor and others. Studies have indicated that many tyrosine kinases are transmembrane proteins with their receptor domains located on the outside of the cell and their kinase domains on the inside. Much work is also under progress to identify modulators of tyrosine kinases as well.

A major signal transduction systems utilized by cells is the RhoA-signalling pathways. RhoA is a small GTP binding protein that can be activated by several extracellular stimuli such as growth factor, hormones, mechanic stress, osmotic change as well as high concentration of metabolite like glucose. RhoA activation involves GTP binding, conformation alteration, post-translational modification (geranylgeranyllization and farnesylation) and activation of its intrinsic GTPase activity. Activated RhoA is capable of interacting with several effector proteins including ROCKs (ROCK1 and ROCK2, also referred to below as 'ROCK' or 'ROCKs') and transmit signals into cellular cytoplasm and nucleus.

ROCK1 and 2 constitute a family of kinases that can be activated by RhoA-GTP complex via physical association. Activated ROCKs phosphorylate a number of substrates and play important roles in pivotal cellular functions. The substrates for ROCKs include myosin binding subunit of myosin light chain phosphatase (MBS, also named MYPT1), adducin, moesin, myosin light chain (MLC), LIM kinase as well as transcription factor FHL. The phosphorylation of theses substrates modulate the biological activity of the proteins and thus provide a means to alter cell's response to external stimuli. One well documented example is the participation of ROCK in smooth muscle contraction. Upon stimulation by phenylephrine, smooth muscle from blood vessels contracts. Studies have shown that phenylephrine stimulates b-adrenergic receptors and leads to the activation of RhoA. Activated RhoA in turn stimulates kinase activity of ROCK1 and which in turn phosphorylates MBS. Such phosphorylation inhibits the enzyme activity of myosin light chain phosphatase and increases the phosphorylation of myosin light chain itself by a calcium-dependent myosin light chain kinase (MLCK) and consequently increases the contractility of myosin-actin bundle, leading to smooth muscle contraction. This phenomena is also sometimes called calcium sensitization. In addition to smooth muscle contraction, ROCKs have also been shown to be involved in cellular functions including apoptosis, cell migration, transcriptional activation, fibrosis, cytokinesis, inflammation and cell proliferation. Moreover, in neurons ROCK plays a critical role in the inhibition of axonal growth by myelin-associated inhibitory factors such as myelin-associated glycoprotein (MAG). ROCK-activity also mediates the collapse of growth cones in developing neurons. Both processes are thought to be mediated by ROCK-induced phosphorylation of substrates such as LIM kinase and myosin light chain phosphatase, resulting in increased contractility of the neuronal actin-myosin system.

The present inventors have discovered novel azabenzimidazole compounds, which are inhibitors of ROCK activity and show interesting selectivity over other protein kinases. Such derivatives are useful in the treatment of disorders associated with inappropriate ROCK activity.

DETAILED DESCRIPTION OF THE INVENTION

The present invention thus provides compounds of the general formula (I)

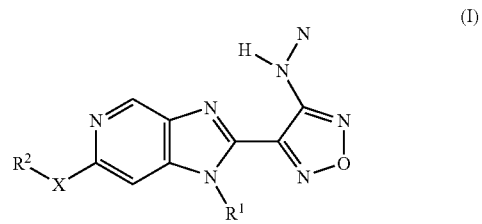

and physiologically acceptable salts wherein,
X represents $C_{1-6}$ alkyl, $NR^3$, O or $S(O)_n$ were n is 0, 1, or 2;
$R^1$ represents $C_{1-6}$ alkyl, optionally substituted by a group selected from the group consisting of optionally substituted phenyl, $C_{1-3}$ alkoxy, $C_{3-7}$cycloalkyl, heteroaryl, heterocyclyl, $NH_2$, $R^4R^5N$, acylamino, hydroxy, $CONR^4R^5$, $NR^4COR^5$, $SO_2NR^4R^5$, $NR^4SO_2R^5$, $OalkNR^4R^5$, or $SalkNR^4R^5$, alkenyl optionally substituted phenyl, heterocyclyl, or heteoaryl, optionally substituted phenyl, heteroaryl, cycloalkyl, cycloalkylalkyl, heterocyclyl;

$R^2$ represents $C_{1-6}$ alkyl, optionally substituted by a group selected from the group consisting of optionally substituted phenyl, $C_{3-7}$cycloalkyl, heteroaryl, heterocyclyl, $NH_2$, $R^4R^5N$, acylamino, hydroxy, $CO_2R^4$, $CONR^4R^5$, $NR^4COR^5$, $NR^4CSR^5$, $SO_2NR^4R^5$, $NR^4SO_2R^5$, $OalkNR^4R^5$, optionally substituted phenyl, heteroaryl, heterocyclyl, $CONR^4R^5$;

$R^3$ represents hydrogen, $C_{1-6}$ alkyl, and $C_{3-7}$ cycloalkyl or $R^3$ and $R^2$ together form a ring;

$R^4$ and $R^5$ independently represent a group selected from hydrogen, $C_{1-6}$ alkyl, $C_{3-7}$ cycloalkyl, $C_{3-7}$ cycloalkylalkyl, aryl, aralkyl, heteroaryl, heteroarylalkyl, heterocyclyl or heterocyclylalkyl;

Alk is a $C_{2-4}$ straight or branched alkylene chain;

and the group $X-R^2$ can represent F, Cl, or Br.

It will be appreciated that any of the substituents $R^1$ to $R^5$ as defined in formula (1) above may contain at least one asymmetric center and it is to be understood that the invention includes all possible enantiomers arising therefrom and mixtures thereof including racemates.

The present invention thus provides compounds of the general formula (I)

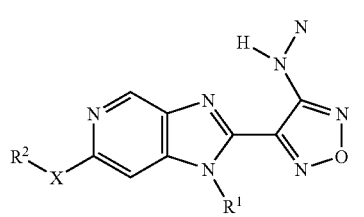

and physiologically acceptable salts wherein,

X is O or S;

$R^1$ represents $C_{1-4}$ alkyl, optionally substituted phenyl, heteroaryl, $C_{3-6}$cycloalkyl, $C_{3-6}$cycloalkylalkyl;

$R^2$ represents $C_{1-3}$ alkyl, optionally substituted by a group selected from the group consisting of optionally substituted phenyl, $C_{1-3}$ alkoxy $C_{3-7}$cycloalkyl, heteroaryl, heterocyclyl, $NH_2$, $R^4R^5N$, acylamino, hydroxy, $CO_2R^4$, $CONR^4R^5$, $NR^4COR^5$, $SO_2NR^4R^5$, $NR^4SO_2R^5$ optionally substituted phenyl, heteroaryl, heterocyclyl, $CONR^4R^5$;

$R^4$ and $R^5$, independently, represent a group selected from hydrogen, $C_{1-6}$ alkyl, $C_{3-7}$ cycloalkyl, $C_{3-7}$ cycloalkylalkyl, aryl, aralkyl, heteroaryl, heteroarylalkyl, heterocyclyl and heterocyclylalkyl, or $R^4$ and $R^5$ together form a ring;

Alk is a $C_{2-4}$ straight or branched alkylene chain.

It will be appreciated that any of the substituents $R^1$ to $R^5$ as defined in formula (1) above may contain at least one asymmetric center and it is to be understood that the invention includes all possible enantiomers arising therefrom and mixtures thereof including racemates.

The present invention thus provides compounds of the general formula (I)

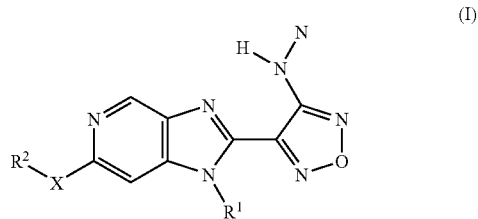

and physiologically acceptable salts wherein,

X is O;

$R^1$ represents $C_{1-4}$ alkyl, optionally substituted phenyl, heteroaryl, heterocyclyl, $C_{1-3}$ alkoxy, $C_{3-6}$cycloalkyl, $C_{3-6}$cycloalkylalkyl;

$R^2$ represents optionally substituted phenyl, heteroaryl, heterocyclyl, $CONR^4R^5$;

$R^4$ and $R^5$, independently, represent a group selected from hydrogen, $C_{1-6}$ alkyl, $C_{3-7}$ cycloalkyl, $C_{3-7}$ cycloalkylalkyl, aryl, aralkyl, heteroaryl, heteroarylalkyl, heterocyclyl and heterocyclylalkyl, or $R^4$ and $R^5$ together form a ring;

Alk is a $C_{2-4}$ straight or branched alkylene chain.

It will be appreciated that any of the substituents $R^1$ to $R^5$ as defined in formula (1) above may contain at least one asymmetric center and it is to be understood that the invention includes all possible enantiomers arising therefrom and mixtures thereof including racemates.

The term alkyl as a group or part of a group e.g. alkoxy, alkylthio, alkylamino, dialkylamino, optionally substituted alkyl e.g. aminoalkyl, cycloalkylalkyl, aralkyl, heteroarylalkyl or heterocyclylalkyl refers to a $C_{1-6}$ straight or branched chain alkyl group.

The term halogen includes fluorine, chlorine, bromine or iodine.

The term aryl as a group or part of a group e.g. aryloxy, aralkyl or arylamino refers to an optionally substituted phenyl or fused bicyclic aryl group e.g. naphthyl. The terms aryl, optionally substituted phenyl, heteroaryl, $C_{3-7}$ cycloalkyl as a group or part of a group and 4-7 membered heterocyclyl as a group or part of a group includes such groups which are optionally substituted with 1 to 3 substituents which may be the same or different and selected from halogen, aryl, heteroaryl, heterocyclylalkyl, hydroxy, alkyl, alkoxy, trifluoroalkyl, amino, alkylamino, dialkylamino, arylamino, heteroarylamino, heterocyclylamino, acylamino, aminoalkyl, alkylaminoalkyl, dialkylaminoalkyl, acylaminoalkyl, arylaminoalkyl, heteroarylaminoalkyl, cycloalkylaminoalkyl, heteroclylaminoalkyl, hydroxyalkyl, $CONR^4R^5$, $CSNR^4R^5$, $CH_2CONR^4R^5$, carboxy, carboxamido, alkoxycarbonyl, aminoalkoxy, dialkylaminoalkoxy, acylaminoalkoxy, sulphonamido, aminosulphonyl, cyano, formyl, nitro, $R^6O$ or $R^6S(O)_n$ wherein $R^6$ is a group selected from alkyl, aryl, heteroaryl or heterocyclylalkoxy and n is zero, one or two, or each of the said groups can form part of a fused bicyclic ring system containing up to 10 ring members and which can be at least partially saturated.

The term heteroaryl as a group or part of a group e.g. heteroaryloxy refers to a 5, or 6 membered ring or a fused 5,6 or 6,6 bicyclic ring system.

When heteroaryl represents a 5 membered group it contains a heteroatom selected from O, N or S and may optionally contain a further 1 to 3 nitrogen atoms. Examples of such groups include furanyl, thienyl, isoxazolyl, oxazolyl or imidazolyl.

When heteroaryl represents a 6-membered group it contains from 1 to 3 nitrogen atoms. Examples of such groups include pyridyl, pyrimidinyl, or triazinyl. The term 5,6 fused bicyclic heteroaryl group refers to a group in which the 5-membered ring contains an oxygen, sulphur or NH group and may optionally contain a further 1 to 2 nitrogen atoms, and the 6 membered ring optionally contains from 1 to 3 nitrogen atoms. Examples of such groups include benzofuranyl, benzothienyl, benzimidazole, benzotriazole or indolyl.

The term 6,6-fused bicyclic heteroaryl group refers to a bicyclic heteroaryl group which contains at least one nitrogen atom in one of the rings and may contain up to 3 nitrogen atoms in each ring. Examples of such groups include quinolinyl, isoquinolinyl or naphthyridinyl also the term 6,6 fused bicyclic heteroaryl group refers to a 6-membered heteroaryl group which is fused to a partially saturated carbocyclic group. Examples of such a group includes tetrahydroquinolinyl or tetrahydroisoquinolinyl.

The term heterocyclyl as a group or part of a group e.g. heterocyclylalkyl or heterocyclylalkylidene refers to a bridged heterocyclic group or a 4-7 membered heterocyclyl group which is linked to the rest of the compound of formula (1) via a carbon or nitrogen atom in that group and which contains one or two hetero atoms selected from N, O or $S(O)_n$, and when the heterocyclyl group contains a ring member NH or the heterocyclyl group is substituted by a primary or secondary amino group then the term also includes N-alkyl, N-optionally substituted phenyl, N-aralkyl, N-sulfonyl, or, N-acyl derivatives thereof. The term heterocyclic also includes bridged heterocyclic. Examples of such heterocyclic groups include optionally substituted pyrrolidine, piperidine, piperazine, homopiperazine, morpholine, thiomorpholine and (8-methyl-8-aza-bicyclo[3.2.1]oct-3-yl)-amine.

The term cycloalkyl as a group or part of a group e.g. cycloalkylalkyl or cycloalkylidene refers to a 3-7 membered carbocyclic group.

The term fused bicyclic ring system containing up to 11 ring members and which is at least partially saturated includes carbocyclic and heterocyclic 6,5, 6,6 and 6,7 bicyclic ring systems. Examples of such 6,5 and 6,6 carbocyclic ring systems include those wherein the bicyclic ring comprises a benzene ring fused to a 5-, 6- or membered carbocyclic ring which is at least partially saturated e.g. tetrahydronaphthyl, indanyl or indenyl. Examples of such 6,5, 6,6 or 6,7 heterocyclic rings include those wherein one ring is benzene which is fused to a 5, 6 or 7 membered ring containing one or two hetero atoms selected from O, S or N e.g. indolinyl, isoindolinyl, 2,3-dihydro-1H-isoindol-5-yl, dihydrobenzofuranyl, dihydrobenzothienyl, 1,3-benzodioxolyl, benzopyrrolyl, 1,3-benozodithiolyl, 1,4-benzodioxanyl, chromanyl, chromenyl or 2,3,4,5-tetrahydro-1H-benzo[c]azepin-8-yl The term acyl as a group or part of the acylamino group refers to an alkanoyl, aroyl, aralkanoyl, alkoxycarbonyl, aryloxycaronyl or aralkoxycarbonyl group.

The compounds of formula (I) form salts with inorganic and organic acids and the invention includes such salts formed with physiologically acceptable inorganic and organic acids.

The group $R^1$ is preferably a group such as, but not limited to, $C_{1-6}$alkyl such as ethyl, $C_{3-7}$cycloalkylalkyl e.g. $C_{3-7}$ cycloalkylmethyl such as cyclopropylmethyl, optionally substituted phenyl such as phenyl or phenyl substituted by hydroxy, amino e.g. methansulfonylamino, alkoxy, e.g. 2-dimethylaminoethoxy, 2-methylaminoethoxy, aminoethoxy, heterocyclylalkoxy e.g. N-methyl-pyrrolidino-2-yl-methoxy, 6,6 fused bicyclicheterocyclic e.g. 2-methyl tetrahydroisoquinolin-7-yl, 2-(aminoacetyl)-tetrahydroisoquinolin-7-yl, 2-(aminocarbonylmethyl)-tetrahydroisoquinolin-7-yl or tetrahydroisoquinolin-7-yl.

The group X is preferably, but not limited to, O or S.

Preferred examples of $R^2$ include, but are not limited to, alkyl, e.g. methyl, acetylaminoethyl, [1-(2-methylpropanoyl)proline]-3-yl, aralkyl, e.g. benzyl, cycloalkyl, e.g. cyclopentyl, alkenyl, e.g. 2-methoxycarbonylethenyl, optionally substituted phenyl (e.g. phenyl or phenyl substituted by one or two groups selected from alkyl, e.g. methyl, isopropyl, 1-hydroxyethyl, 1-hydroxy-1-methyl-propyl, alkylthioether, e.g. methylthio, alkylsulfinyl, e.g. methylsulfinyl, alkylsulfonyl, e.g. methylsulfonyl, alkoxy e.g. methoxy or ethoxy, hydroxy, hydroxymethyl, methoxycarbonylmethyl, carboxymethyl, trifluoromethyl, amino, alkylamino, e.g. dimethylamino, alkylthionoamdio, e.g. thionoacetamido, alkylamido e.g., acetamido, propanamido, methoxyacetamido, butanamido, 2-methylpropanamido, 2-methoxypropanamido, N-methylacetamido, cyclopropylacetamido, heteroaraalkylamido, e.g., 5-methyl-thioazol-2-ylacetamido, 1,5-dimethylpyrazol-4-ylacetamide, arylamido, e.g. 4-ethoxybenzimido, 4-methoxybenzamido, 3-methoxybenzamido, 4-cyanobenzamido, heteroarylamido, e.g. 3-pyridylamido, 2-furanylamido, benzamido, 4-fluorobenzamido, carboxyl, methoxycarbonyl, carboxamido, e.g. carboxamido, N,N-dimethylcarboxamide, N-methylcarboxamido, N-(2-methoxyethyl)carboxamido, N-(3-ethoxypropyl)carboxamido, N-ethylcarboxamido, piperidincarbonyl, aminoalkylcarboxamido, e.g. 2-morpholinoethylcarboxamido, 3-morpholinopropylcarboxamido, ureido, e.g. ureido, N'-methylureido, N'-benzylureido, N',N'-morpholinureido, N'-phenylureido, alkylsulfonamido, e.g. methansulfonamido, butansulfonamido, arylsulfonamido, e.g. 4-fluorobenzenesulfonamido, 4-methylbenzenesulfonamido, 4-methoxybenzenesulfonamido, sulfonyl urea, e.g. dimethylaminosulfonamide, halogen, e.g. fluoro, chloro, acyl, e.g. acetyl, propanoyl, cyano, nitro, or heterocyclyl e.g. morpholino), heteroaryl, e.g. 2-imidazolyl, 2-thioazolyl, 2,5-dimethylfuran-3-yl. 2-pyridyl, chromenyl, 7-methoxy-benzothiazol-2-yl, 7-aza-benzothiazol-2-yl, Examples of suitable compounds according to the invention include those listed below and found in Examples 1-24.

3-{[2-(4-Amino-furazan-3-yl)-1-ethyl-1H-imidazo[4,5-c]pyridin-6-yl]thio}phenol,

N-(3-{[2-(4-Amino-furazan-3-yl)-1-ethyl-1H-imidazo[4,5-c]pyridin-6-yl]thio}phenyl)acetamide;

N-(3-{[2-(4-Amino-furazan-3-yl)-1-ethyl-1H-imidazo[4,5-c]pyridin-6-yl]thio}phenyl)ethanethioamide;

4-(6-{[3,4-Bis(methyloxy)phenyl]thio}-1-ethyl-1H-imidazo[4,5-c]pyridin-2-yl)-furazan-3-amine;

Methyl 3-{[2-(4-amino-furazan-3-yl)-1-ethyl-1H-imidazo[4,5-c]pyridin-6-yl]thio}benzoate;

4-(1-Ethyl-6-{[3-(methyloxy)phenyl]thio}-1H-imidazo[4,5-c]pyridin-2-yl)-furazan-3-amine;

3-{[2-(4-Amino-furazan-3-yl)-1-ethyl-1H-imidazo[4,5-c]pyridin-6-yl]thio}benzoic acid;

4-(1-Ethyl-6-{[2-(methyloxy)phenyl]thio}-1H-imidazo[4,5-c]pyridin-2-yl)-furazan-3-amine;

4-[1-Ethyl-6-(1H-imidazol-2-ylthio)-1H-imidazo[4,5-c]pyridin-2-yl]-furazan-3-amine;

4-[6-(Cyclopentylthio)-1-ethyl-1H-imidazo[4,5-c]pyridin-2-yl]-furazan-3-amine;

4-[1-Ethyl-6-(1,3-thiazol-2-ylthio)-1H-imidazo[4,5-c]pyridin-2-yl]-furazan-3-amine;

4-{1-Ethyl-6-[(phenylmethyl)thio]-1H-imidazo[4,5-c]pyridin-2-yl}-furazan-3-amine;

4-[1-Ethyl-6-(phenylthio)-1H-imidazo[4,5-c]pyridin-2-yl]-furazan-3-amine;
methyl 2-{[2-(4-amino-furazan-3-yl)-1-ethyl-1H-imidazo[4,5-c]pyridin-6-yl]thio}benzoate;
N-(4-{[2-(4-Amino-furazan-3-yl)-1-ethyl-1H-imidazo[4,5-c]pyridin-6-yl]thio}phenyl)acetamide;
4-{6-[(3-Chloro-4-fluorophenyl)thio]-1-ethyl-1H-imidazo[4,5-c]pyridin-2-yl}-furazan-3-amine;
4-{[2-(4-Amino-furazan-3-yl)-1-ethyl-1H-imidazo[4,5-c]pyridin-6-yl]thio}benzoic acid;
N-(2-{[2-(4-Amino-furazan-3-yl)-1-ethyl-1H-imidazo[4,5-c]pyridin-6-yl]thio}ethyl)acetamide;
4-{6-[(2,5-dimethyl-3-furanyl)thio]-1-ethyl-1H-imidazo[4,5-c]pyridin-2-yl}-furazan-3-amine;
4-[1-Ethyl-6-(phenylsulfinyl)-1H-imidazo[4,5-c]pyridin-2-yl]-furazan-3-amine;
4-{6-[(3,4-Dichlorophenyl)thio]-1-ethyl-1H-imidazo[4,5-c]pyridin-2-yl}-furazan-3-amine;
4-[1-Ethyl-6-(2-pyridinylthio)-1H-imidazo[4,5-c]pyridin-2-yl]-furazan-3-amine;
4-{1-Ethyl-6-[(4-fluorophenyl)thio]-1H-imidazo[4,5-c]pyridin-2-yl}-furazan-3-amine;
7-{[2-(4-Amino-furazan-3-yl)-1-ethyl-1H-imidazo[4,5-c]pyridin-6-yl]thio}-3-methyl-2H-chromen-2-one;
4-(1-Ethyl-6-{[4-(trifluoromethyl)phenyl]thio}-1H-imidazo[4,5-c]pyridin-2-yl)-furazan-3-amine;
1-((2S)-3-{[2-(4-Amino-furazan-3-yl)-1-ethyl-1H-imidazo[4,5-c]pyridin-6-yl]thio}-2-methylpropanoyl)-L-proline;
4-(1-Ethyl-6-{[4-(methylthio)phenyl]thio}-1H-imidazo[4,5-c]pyridin-2-yl)-furazan-3-amine;
4-[1-Ethyl-6-(4-pyridinylthio)-1H-imidazo[4,5-c]pyridin-2-yl]-furazan-3-amine;
4-[1-Ethyl-6-([1,3]thiazolo[4,5-b]pyridin-2-ylthio)-1H-imidazo[4,5-c]pyridin-2-yl]-furazan-3-amine;
4-(1-Ethyl-6-{[5-(methyloxy)-1,3-benzothiazol-2-yl]thio}-1H-imidazo[4,5-c]pyridin-2-yl)-furazan-3-amine;
Methyl (2E)-3-(4-{[2-(4-amino-furazan-3-yl)-1-ethyl-1H-imidazo[4,5-c]pyridin-6-yl]thio}phenyl)-2-propenoate;
4-(1-Ethyl-6-{[4-(methylsulfonyl)phenyl]sulfinyl}-1H-imidazo[4,5-c]pyridin-2-yl)-furazan-3-amine;
4-(1-Ethyl-6-{[4-(methylsulfinyl)phenyl]sulfinyl}-1H-imidazo[4,5-c]pyridin-2-yl)-furazan-3-amine;
4-{6-[(4-Fluorophenyl)oxy]-1-phenyl-1H-imidazo[4,5-c]pyridin-2-yl}-furazan-3-amine;
4-(1-Ethyl-6-{[3-(methyloxy)phenyl]oxy}-1H-imidazo[4,5-c]pyridin-2-yl)-furazan-3-amine;
4-{6-[(3,4-Dimethylphenyl)oxy]-1-ethyl-1H-imidazo[4,5-c]pyridin-2-yl}-furazan-3-amine;
N-(3-{[2-(4-Amino-furazan-3-yl)-1-phenyl-1H-imidazo[4,5-c]pyridin-6-yl]oxy}phenyl)acetamide;
4-{6-[(3-Aminophenyl)oxy]-1-phenyl-1H-imidazo[4,5-c]pyridin-2-yl}-furazan-3-amine;
4-{6-[(4-Aminophenyl)oxy]-1-phenyl-1H-imidazo[4,5-c]pyridin-2-yl}-furazan-3-amine;
3-{[2-(4-Amino-furazan-3-yl)-1-ethyl-1H-imidazo[4,5-c]pyridin-6-yl]oxy}benzonitrile;
1-(3-{[2-(4-Amino-furazan-3-yl)-1-ethyl-1H-imidazo[4,5-c]pyridin-6-yl]oxy}phenyl)ethanone;
N-(4-{[2-(4-Amino-furazan-3-yl)-1-phenyl-1H-imidazo[4,5-c]pyridin-6-yl]oxy}phenyl)acetamide;
4-(1-Ethyl-6-{[3-(1-methylethyl)phenyl]oxy}-1H-imidazo[4,5-c]pyridin-2-yl)-furazan-3-amine;
4-(6-{[3-(Dimethylamino)phenyl]oxy}-1-ethyl-1H-imidazo[4,5-c]pyridin-2-yl)-furazan-3-amine;
4-(1-Ethyl-6-{[3-(4-morpholinyl)phenyl]oxy}-1H-imidazo[4,5-c]pyridin-2-yl)-furazan-3-amine;
N-(3-{[2-(4-Amino-furazan-3-yl)-1-ethyl-1H-imidazo[4,5-c]pyridin-6-yl]oxy}phenyl)-4-methylbenzenesulfonamide;
4-(1-Ethyl-7-{[3-(methyloxy)phenyl]oxy}-1H-imidazo[4,5-c]pyridin-2-yl)-furazan-3-amine;
1,1-Dimethylethyl (3-{[2-(4-amino-furazan-3-yl)-1-ethyl-1H-imidazo[4,5-c]pyridin-6-yl]oxy}phenyl)carbamate;
4-{2-(4-Amino-furazan-3-yl)-6-[(4-fluorophenyl)oxy]-1H-imidazo[4,5-c]pyridin-1-yl}phenol;
4-{6-[(3-Aminophenyl)oxy]-1-ethyl-1H-imidazo[4,5-c]pyridin-2-yl}-furazan-3-amine;
N-(3-{[2-(4-Amino-furazan-3-yl)-1-ethyl-1H-imidazo[4,5-c]pyridin-6-yl]oxy}phenyl)methanesulfonamide;
N-(3-{[2-(4-Amino-furazan-3-yl)-1-(4-hydroxyphenyl)-1H-imidazo[4,5-c]pyridin-6-yl]oxy}phenyl)acetamide;
N-(3-{[2-(4-Amino-furazan-3-yl)-1-ethyl-1H-imidazo[4,5-c]pyridin-6-yl]oxy}phenyl)-N'-methylurea;
N-(3-{[2-(4-Amino-furazan-3-yl)-1-(4-{[2-(dimethylamino)ethyl]oxy}phenyl)-1H-imidazo[4,5-c]pyridin-6-yl]oxy}phenyl)acetamide;
N-(4-{[2-(4-Amino-furazan-3-yl)-1-(4-{[2-(dimethylamino)ethyl]oxy}phenyl)-1H-imidazo[4,5-c]pyridin-6-yl]oxy}phenyl)acetamide;
Methyl 4-{[2-(4-amino-furazan-3-yl)-1-ethyl-1H-imidazo[4,5-c]pyridin-6-yl]oxy}benzoate;
Methyl 3-{[2-(4-amino-furazan-3-yl)-1-ethyl-1H-imidazo[4,5-c]pyridin-6-yl]oxy}benzoate;
4-[6-[(4-Fluorophenyl)oxy]-1-(2-methyl-1,2,3,4-tetrahydro-7-isoquinolinyl)-1H-imidazo[4,5-c]pyridin-2-yl]-furazan-3-amine;
1-(3-{[2-(4-Amino-furazan-3-yl)-1-ethyl-1H-imidazo[4,5-c]pyridin-6-yl]oxy}phenyl)ethanol;
2-(3-{[2-(4-Amino-furazan-3-yl)-1-ethyl-1H-imidazo[4,5-c]pyridin-6-yl]oxy}phenyl)-2-butanol;
6-{[2-(4-Amino-furazan-3-yl)-1-ethyl-1H-imidazo[4,5-c]pyridin-6-yl]oxy}-3,4-dihydro-1(2H)-naphthalenone;
N-(3-{[2-(4-Amino-furazan-3-yl)-1-ethyl-1H-imidazo[4,5-c]pyridin-6-yl]oxy}phenyl)-N'-(phenylmethyl)urea;
Methyl (3-{[2-(4-amino-furazan-3-yl)-1-ethyl-1H-imidazo[4,5-c]pyridin-6-yl]oxy}phenyl)acetate;
(3-{[2-(4-Amino-furazan-3-yl)-1-ethyl-1H-imidazo[4,5-c]pyridin-6-yl]oxy}phenyl)acetic acid;
4-{[2-(4-Amino-furazan-3-yl)-1-ethyl-1H-imidazo[4,5-c]pyridin-6-yl]oxy}benzonitrile;
3-{[2-(4-Amino-furazan-3-yl)-1-ethyl-1H-imidazo[4,5-c]pyridin-6-yl]oxy}benzoic acid;
N-(3-{[2-(4-Amino-furazan-3-yl)-1-(4-{[2-(methylamino)ethyl]oxy}phenyl)-1H-imidazo[4,5-c]pyridin-6-yl]oxy}phenyl)acetamide;
N-(3-{[1-{4-[(2-Aminoethyl)oxy]phenyl}-2-(4-amino-furazan-3-yl)-1H-imidazo[4,5-c]pyridin-6-yl]oxy}phenyl)acetamide;
N-[3-({2-(4-Amino-furazan-3-yl)-1-[4-({[(2S)-1-methyl-2-pyrrolidinyl]methyl}oxy)phenyl]-1H-imidazo[4,5-c]pyridin-6-yl}oxy)phenyl]acetamide;
N-(3-{[2-(4-Amino-furazan-3-yl)-1-ethyl-1H-imidazo[4,5-c]pyridin-6-yl]oxy}phenyl)-4-(methyloxy)benzamide;
N-(3-{[2-(4-Amino-furazan-3-yl)-1-ethyl-1H-imidazo[4,5-c]pyridin-6-yl]oxy}phenyl)-4-fluorobenzamide;
N-(3-{[2-(4-Amino-furazan-3-yl)-1-ethyl-1H-imidazo[4,5-c]pyridin-6-yl]oxy}phenyl)-2-furancarboxamide;
N-(3-{[2-(4-Amino-furazan-3-yl)-1-ethyl-1H-imidazo[4,5-c]pyridin-6-yl]oxy}phenyl)-2-methylpropanamide;
N-(3-{[2-(4-Amino-furazan-3-yl)-1-ethyl-1H-imidazo[4,5-c]pyridin-6-yl]oxy}phenyl)butanamide;
N-(3-{[2-(4-Amino-furazan-3-yl)-1-ethyl-1H-imidazo[4,5-c]pyridin-6-yl]oxy}phenyl)-2-(methyloxy)acetamide;

3-{[2-(4-Amino-furazan-3-yl)-1-ethyl-1H-imidazo[4,5-c] pyridin-6-yl]oxy}phenol;

Methyl 3-{[2-(4-amino-furazan-3-yl)-1-phenyl-1H-imidazo [4,5-c]pyridin-6-yl]oxy}benzoate;

3-{[2-(4-Amino-furazan-3-yl)-1-phenyl-1H-imidazo[4,5-c] pyridin-6-yl]oxy}benzoic acid;

N-(3-{[2-(4-Amino-furazan-3-yl)-1-ethyl-1H-imidazo[4,5-c]pyridin-6-yl]oxy}phenyl)-4-morpholinecarboxamide;

N-(3-{[2-(4-Amino-furazan-3-yl)-1-ethyl-1H-imidazo[4,5-c]pyridin-6-yl]oxy}phenyl)benzamide;

N-(3-{[2-(4-Amino-furazan-3-yl)-1-ethyl-1H-imidazo[4,5-c]pyridin-6-yl]oxy}phenyl)-4-fluorobenzenesulfonamide;

N-(4-{[2-(4-Amino-furazan-3-yl)-1-(4-hydroxyphenyl)-1H-imidazo[4,5-c]pyridin-6-yl]oxy}phenyl)acetamide;

3-{[2-(4-Amino-furazan-3-yl)-1-phenyl-1H-imidazo[4,5-c] pyridin-6-yl]oxy}-N,N-dimethylbenzamide;

3-{[2-(4-Amino-furazan-3-yl)-1-phenyl-1H-imidazo[4,5-c] pyridin-6-yl]oxy}-N-methylbenzamide;

3-{[2-(4-Amino-furazan-3-yl)-1-phenyl-1H-imidazo[4,5-c] pyridin-6-yl]oxy}benzamide;

4-{1-Phenyl-6-{[3-(1-piperidinylcarbonyl)phenyl]oxy}-1H-imidazo[4,5-c]pyridin-2-yl)-furazan-3-amine;

3-{[2-(4-Amino-furazan-3-yl)-1-phenyl-1H-imidazo[4,5-c] pyridin-6-yl]oxy}-N-methylbenzamide;

N-(3-{[2-(4-Amino-furazan-3-yl)-1-ethyl-1H-imidazo[4,5-c]pyridin-6-yl]oxy}phenyl)-N-methylacetamide;

N-(3-{[2-(4-Amino-furazan-3-yl)-1-(1,2,3,4-tetrahydro-7-isoquinolinyl)-1H-imidazo[4,5-c]pyridin-6-yl] oxy}phenyl)acetamide;

3-{[2-(4-Amino-furazan-3-yl)-1-phenyl-1H-imidazo[4,5-c] pyridin-6-yl]oxy}-N-[2-(methyloxy)ethyl]benzamide;

3-{[2-(4-Amino-furazan-3-yl)-1-phenyl-1H-imidazo[4,5-c] pyridin-6-yl]oxy}-N-[2-(4-morpholinyl)ethyl]benzamide;

1-(3-{[2-(4-Amino-furazan-3-yl)-1-phenyl-1H-imidazo[4,5-c]pyridin-6-yl]oxy}phenyl)ethanone;

N-(3-{[2-(4-Amino-furazan-3-yl)-1-ethyl-1H-imidazo[4,5-c]pyridin-6-yl]oxy}phenyl)-N'-phenylurea;

N-(3-{[2-(4-Amino-furazan-3-yl)-1-ethyl-1H-imidazo[4,5-c]pyridin-6-yl]oxy}phenyl)-4-(methyloxy)benzenesulfonamide;

N-(3-{[2-(4-Amino-furazan-3-yl)-1-ethyl-1H-imidazo[4,5-c]pyridin-6-yl]oxy}phenyl)-N,N-dimethylsulfamide;

N-(3-{[2-(4-Amino-furazan-3-yl)-1-ethyl-1H-imidazo[4,5-c]pyridin-6-yl]oxy}phenyl)-1-butanesulfonamide;

N-(3-{[2-(4-Amino-furazan-3-yl)-1-ethyl-1H-imidazo[4,5-c]pyridin-6-yl]oxy}phenyl)-3-pyridinecarboxamide;

4-{1-Athyl-6-[(phenylmethyl)oxy]-1H-imidazo[4,5-c]pyridin-2-yl}-furazan-3-amine;

N-(3-{[2-(4-Amino-furazan-3-yl)-1-(4-{[2-(dimethylamino)ethyl]oxy}phenyl)-1H-imidazo[4,5-c]pyridin-6-yl]oxy}phenyl)methanesulfonamide;

4-{6-[(3-Nitrophenyl)oxy]-1-phenyl-1H-imidazo[4,5-c]pyridin-2-yl}-furazan-3-amine;

N-(3-{[2-(4-Amino-furazan-3-yl)-1-ethyl-1H-imidazo[4,5-c]pyridin-6-yl]oxy}phenyl)-4-cyanobenzamide;

N-(3-{[2-(4-Amino-furazan-3-yl)-1-ethyl-1H-imidazo[4,5-c]pyridin-6-yl]oxy}phenyl)cyclohexanecarboxamide;

N-(3-{[2-(4-Amino-furazan-3-yl)-1-ethyl-1H-imidazo[4,5-c]pyridin-6-yl]oxy}phenyl)-3-(methyloxy)benzamide;

N-(3-{[2-(4-Amino-furazan-3-yl)-1-ethyl-1H-imidazo[4,5-c]pyridin-6-yl]oxy}phenyl)-4-(dimethylamino)benzamide;

N-(3-{[2-(4-Amino-furazan-3-yl)-1-ethyl-1H-imidazo[4,5-c]pyridin-6-yl]oxy}phenyl)-4-(methyloxy)benzamide;

N-(3-{[2-(4-Amino-furazan-3-yl)-1-ethyl-1H-imidazo[4,5-c]pyridin-6-yl]oxy}phenyl)urea;

3-{[2-(4-Amino-furazan-3-yl)-1-phenyl-1H-imidazo[4,5-c] pyridin-6-yl]oxy}-N-(cyclopropylmethyl)benzamide;

3-{[2-(4-Amino-furazan-3-yl)-1-phenyl-1H-imidazo[4,5-c] pyridin-6-yl]oxy}-N-[(4-methyl-1,3-thiazol-2-yl)methyl] benzamide;

3-{[2-(4-Amino-furazan-3-yl)-1-phenyl-1H-imidazo[4,5-c] pyridin-6-yl]oxy}-N-[(1,5-dimethyl-1H-pyrazol-4-yl) methyl]benzamide;

3-{[2-(4-Amino-furazan-3-yl)-1-phenyl-1H-imidazo[4,5-c] pyridin-6-yl]oxy}-N-[3-(4-morpholinyl)propyl]benzamide;

4-[6-[(4-Fluorophenyl)oxy]-1-(1,2,3,4-tetrahydro-7-isoquinolinyl)-1H-imidazo[4,5-c]pyridin-2-yl]-furazan-3-amine;

4-[2-(4-Amino-furazan-3-yl)-6-bromo-1H-imidazo[4,5-c] pyridin-1-yl]phenol;

N-[5-{[2-(4-Amino-furazan-3-yl)-1-ethyl-1H-imidazo[4,5-c]pyridin-6-yl]thio}-2-(methyloxy)phenyl]acetamide;

1-(3-{[2-(4-Amino-furazan-3-yl)-1-ethyl-1H-imidazo[4,5-c]pyridin-6-yl]oxy}phenyl)-1-propanone;

3-{[2-(4-Amino-furazan-3-yl)-1-phenyl-1H-imidazo[4,5-c] pyridin-6-yl]oxy}-N-[3-(ethyloxy)propyl]benzamide;

N-(4-{2-(4-Amino-furazan-3-yl)-6-[(4-fluorophenyl)oxy]-1H-imidazo[4,5-c]pyridin-1-yl}phenyl)methanesulfonamide;

4-{1-(Aminoacetyl)-1,2,3,4-tetrahydro-7-isoquinolinyl]-6-[(4-fluorophenyl)oxy]-1H-imidazo[4,5-c]pyridin-2-yl}-furazan-3-amine;

N-(3-{[2-(4-Amino-furazan-3-yl)-1-ethyl-1H-imidazo[4,5-c]pyridin-6-yl]oxy}phenyl)-4-(ethyloxy)benzamide;

N-(3-{[2-(4-Amino-furazan-3-yl)-1-ethyl-1H-imidazo[4,5-c]pyridin-6-yl]oxy}phenyl)-3-methylbutanamide;

4-({[(3-{[2-(4-Amino-furazan-3-yl)-1-ethyl-1H-imidazo[4,5-c]pyridin-6-yl]oxy}phenyl)amino]carbonyl}amino) benzoic acid;

4-[6-Bromo-1-(4-{[2-(dimethylamino)ethyl]oxy}phenyl)-1H-imidazo[4,5-c]pyridin-2-yl]-furazan-3-amine;

2-[7-{2-(4-Amino-furazan-3-yl)-6-[(4-fluorophenyl)oxy]-1H-imidazo[4,5-c]pyridin-1-yl}-3,4-dihydro-2(1H)-isoquinolinyl]acetamide;

3-{[2-(4-Amino-furazan-3-yl)-1-ethyl-1H-imidazo[4,5-c] pyridin-6-yl]amino}benzenethiol;

2-(4-Amino-furazan-3-yl)-1-ethyl-N-(phenylmethyl)-1H-imidazo[4,5-c]pyridin-6-amine;

4-[6-[(4-Fluorophenyl)oxy]-1-(4-{[2-(methylamino)ethyl] oxy}phenyl)-1H-imidazo[4,5-c]pyridin-2-yl]-furazan-3-amine;

4-{2-(4-Amino-furazan-3-yl)-6-[(4-fluorophenyl)oxy]-1H-imidazo[4,5-c]pyridin-1-yl}-2-chlorophenol;

4-{1-(3-Chloro-4-{[2-(dimethylamino)ethyl]oxy}phenyl)-6-[(4-fluorophenyl)oxy]-1H-imidazo[4,5-c]pyridin-2-yl}-furazan-3-amine;

3-{[2-(4-Amino-furazan-3-yl)-1-(4-hydroxyphenyl)-1H-imidazo[4,5-c]pyridin-6-yl]oxy}-N-[2-(4-morpholinyl) ethyl]benzamide;

N-[2-(Acetylamino)ethyl]-3-{[2-(4-amino-furazan-3-yl)-1-phenyl-1H-imidazo[4,5-c]pyridin-6-yl]oxy}benzamide;

3-{[2-(4-Amino-furazan-3-yl)-1-phenyl-1H-imidazo[4,5-c] pyridin-6-yl]oxy}-N-(tetrahydro-2-furanylmethyl)benzamide;

3-{[2-(4-Amino-furazan-3-yl)-1-phenyl-1H-imidazo[4,5-c] pyridin-6-yl]oxy}-N-[2-(dimethylamino)ethyl]benzamide;

3-{[2-(4-Amino-furazan-3-yl)-1-phenyl-1H-imidazo[4,5-c] pyridin-6-yl]oxy}-N-[2-(1-methyl-1H-pyrrol-2-yl)ethyl] benzamide;

3-{[2-(4-Amino-furazan-3-yl)-1-phenyl-1H-imidazo[4,5-c]pyridin-6-yl]oxy}-N-[2-(2-pyridinyl)ethyl]benzamide;

3-{[2-(4-Amino-furazan-3-yl)-1-phenyl-1H-imidazo[4,5-c]pyridin-6-yl]oxy}-N-[3-(dimethylamino)propyl]benzamide;

4-[6-(1H-Benzimidazol-4-yloxy)-1-phenyl-1H-imidazo[4,5-c]pyridin-2-yl]-furazan-3-amine;

N-(3-{[2-(4-Amino-furazan-3-yl)-1-ethyl-1H-imidazo[4,5-c]pyridin-6-yl]oxy}phenyl)-6-methyl-3-pyridinecarboxamide;

N-(3-{[2-(4-Amino-furazan-3-yl)-1-ethyl-1H-imidazo[4,5-c]pyridin-6-yl]oxy}phenyl)-2-methyl-3-pyridinecarboxamide;

4-{1-[4-(Aminomethyl)phenyl]-6-[(4-fluorophenyl)oxy]-1H-imidazo[4,5-c]pyridin-2-yl}-furazan-3-amine;

3-{[2-(4-Amino-furazan-3-yl)-1-phenyl-1H-imidazo[4,5-c]pyridin-6-yl]oxy}-N-[3-(1H-imidazol-1-yl)propyl]benzamide;

3-{[2-(4-Amino-furazan-3-yl)-1-phenyl-1H-imidazo[4,5-c]pyridin-6-yl]oxy}-N-[2-(1-pyrrolidinyl)ethyl]benzamide;

3-{[2-(4-Amino-furazan-3-yl)-1-phenyl-1H-imidazo[4,5-c]pyridin-6-yl]oxy}-N-[2-(4-hydroxyphenyl)ethyl]benzamide;

3-{[2-(4-Amino-furazan-3-yl)-1-phenyl-1H-imidazo[4,5-c]pyridin-6-yl]oxy}-N-[2-(3-pyridinyl)ethyl]benzamide;

3-{[2-(4-Amino-furazan-3-yl)-1-phenyl-1H-imidazo[4,5-c]pyridin-6-yl]oxy}-N-[2-(phenyloxy)ethyl]benzamide;

3-{[2-(4-Amino-furazan-3-yl)-1-phenyl-1H-imidazo[4,5-c]pyridin-6-yl]oxy}-N-{2-[3,5-bis(methyloxy)phenyl]ethyl}benzamide;

3-{[2-(4-Amino-furazan-3-yl)-1-phenyl-1H-imidazo[4,5-c]pyridin-6-yl]oxy}-N-[3-(2-oxo-1-pyrrolidinyl)propyl]benzamide;

3-{[2-(4-Amino-furazan-3-yl)-1-phenyl-1H-imidazo[4,5-c]pyridin-6-yl]oxy}-N-(1,3-benzodioxol-5-ylmethyl)benzamide;

3-{[2-(4-Amino-furazan-3-yl)-1-phenyl-1H-imidazo[4,5-c]pyridin-6-yl]oxy}-N-(1,4-dioxan-2-ylmethyl)benzamide;

3-{[2-(4-Amino-furazan-3-yl)-1-phenyl-1H-imidazo[4,5-c]pyridin-6-yl]oxy}-N-(4-pyridinylmethyl)benzamide;

3-{[2-(4-Amino-furazan-3-yl)-1-phenyl-1H-imidazo[4,5-c]pyridin-6-yl]oxy}-N-[3-(1-pyrrolidinyl)propyl]benzamide;

3-{[2-(4-Amino-furazan-3-yl)-1-phenyl-1H-imidazo[4,5-c]pyridin-6-yl]oxy}-N-[3-(4-methyl-1-piperazinyl)propyl]benzamide;

3-{[2-(4-Amino-furazan-3-yl)-1-phenyl-1H-imidazo[4,5-c]pyridin-6-yl]oxy}-N-[2-(4-pyridinyl)ethyl]benzamide;

3-{[2-(4-Amino-furazan-3-yl)-1-phenyl-1H-imidazo[4,5-c]pyridin-6-yl]oxy}-N-(2-cyanoethyl)benzamide;

N-(3-{[2-(4-Amino-furazan-3-yl)-1-ethyl-1H-imidazo[4,5-c]pyridin-6-yl]oxy}-2-methylphenyl)acetamide;

7-{[2-(4-Amino-furazan-3-yl)-1-ethyl-1H-imidazo[4,5-c]pyridin-6-yl]oxy}-4-methyl-2(1H)-quinolinone;

N-(3-{[2-(4-Amino-furazan-3-yl)-1-ethyl-1H-imidazo[4,5-c]pyridin-6-yl]oxy}phenyl)-2-(dimethylamino)-5-pyrimidinecarboxamide;

N-(3-{[2-(4-Amino-furazan-3-yl)-1-ethyl-1H-imidazo[4,5-c]pyridin-6-yl]oxy}phenyl)-2-(methyloxy)-3-pyridinecarboxamide;

N-(3-{[2-(4-Amino-furazan-3-yl)-1-ethyl-1H-imidazo[4,5-c]pyridin-6-yl]oxy}phenyl)-4-(1-piperidinyl)benzamide;

N-(3-{[2-(4-Amino-furazan-3-yl)-1-ethyl-1H-imidazo[4,5-c]pyridin-6-yl]oxy}phenyl)-4-(methyloxy)-3-(trifluoromethyl)benzamide;

N-(3-{[2-(4-Amino-furazan-3-yl)-1-ethyl-1H-imidazo[4,5-c]pyridin-6-yl]oxy}phenyl)-3-fluoro-4-(methyloxy)benzamide;

N-(3-{[2-(4-Amino-furazan-3-yl)-1-ethyl-1H-imidazo[4,5-c]pyridin-6-yl]oxy}phenyl)-3-chloro-4-(methyloxy)benzamide;

N-(3-{[2-(4-Amino-furazan-3-yl)-1-ethyl-1H-imidazo[4,5-c]pyridin-6-yl]oxy}phenyl)-4-(4-morpholinyl)benzamide;

N-(3-{[2-(4-Amino-furazan-3-yl)-1-ethyl-1H-imidazo[4,5-c]pyridin-6-yl]oxy}phenyl)-2-methyl-1,3-thiazole-5-carboxamide;

N-(3-{[2-(4-Amino-furazan-3-yl)-1-ethyl-1H-imidazo[4,5-c]pyridin-6-yl]oxy}phenyl)-1-methyl-1H-1,2,3-benzotriazole-5-carboxamide;

N-(3-{[2-(4-Amino-furazan-3-yl)-1-ethyl-1H-imidazo[4,5-c]pyridin-6-yl]oxy}phenyl)-4-methyl-3,4-dihydro-2H-1,4-benzoxazine-7-carboxamide;

N-(3-{[2-(4-Amino-furazan-3-yl)-1-(1,2,3,4-tetrahydro-7-isoquinolinyl)-1H-imidazo[4,5-c]pyridin-6-yl]oxy}phenyl)-4-(methyloxy)benzamide;

N-[(3-{[2-(4-Amino-furazan-3-yl)-1-phenyl-1H-imidazo[4,5-c]pyridin-6-yl]oxy}phenyl)carbonyl]-beta-alanine;

3-{[2-(4-Amino-furazan-3-yl)-1-phenyl-1H-imidazo[4,5-c]pyridin-6-yl]oxy}-N-(3-amino-3-oxopropyl)benzamide;

N-[4-(Aminomethyl)phenyl]-3-{[2-(4-amino-furazan-3-yl)-1-phenyl-1H-imidazo[4,5-c]pyridin-6-yl]oxy}benzamide;

4-[6-(1H-Benzimidazol-5-yloxy)-1-ethyl-1H-imidazo[4,5-c]pyridin-2-yl]-furazan-3-amine;

N-(3-{[2-(4-Amino-furazan-3-yl)-1-ethyl-1H-imidazo[4,5-c]pyridin-6-yl]oxy}phenyl)-4-{[2-(4-morpholinyl)ethyl]oxy}benzamide;

N-(3-{[2-(4-Amino-furazan-3-yl)-1-ethyl-1H-imidazo[4,5-c]pyridin-6-yl]oxy}phenyl)pyrazolo[1,5-a]pyridine-3-carboxamide;

N-(3-{[2-(4-Amino-furazan-3-yl)-1-ethyl-1H-imidazo[4,5-c]pyridin-6-yl]oxy}phenyl)-1-methyl-1H-imidazole-2-carboxamide;

N-(3-{[2-(4-Amino-furazan-3-yl)-1-ethyl-1H-imidazo[4,5-c]pyridin-6-yl]oxy}phenyl)-6-[(2,2,2-trifluoroethyl)oxy]-3-pyridinecarboxamide;

N-(3-{[2-(4-Amino-furazan-3-yl)-1-ethyl-1H-imidazo[4,5-c]pyridin-6-yl]oxy}phenyl)-4-(3,5-dimethyl-1H-pyrazol-1-yl)benzamide;

N-(3-{[2-(4-Amino-furazan-3-yl)-1-ethyl-1H-imidazo[4,5-c]pyridin-6-yl]oxy}phenyl)-4-(trifluoromethyl)-3-pyridinecarboxamide;

4-[2-(4-Amino-furazan-3-yl)-6-(methyloxy)-1H-imidazo[4,5-c]pyridin-1-yl]phenol;

N-(3-{[2-(4-Amino-furazan-3-yl)-1-ethyl-1H-imidazo[4,5-c]pyridin-6-yl]oxy}phenyl)-4-(1H-imidazol-1-yl)benzamide;

N-(3-{[2-(4-Amino-furazan-3-yl)-1-ethyl-1H-imidazo[4,5-c]pyridin-6-yl]oxy}phenyl)-6-(1H-pyrazol-1-yl)-3-pyridinecarboxamide;

4-[1-(4-{[2-(Dimethylamino)ethyl]oxy}phenyl)-6-(methyloxy)-1H-imidazo[4,5-c]pyridin-2-yl]-furazan-3-amine;

N-(3-{[2-(4-Amino-furazan-3-yl)-1-ethyl-1H-imidazo[4,5-c]pyridin-6-yl]oxy}phenyl)-4-{[2-(dimethylamino)ethyl]oxy}benzamide;

N-(3-{[2-(4-Amino-furazan-3-yl)-1-ethyl-1H-imidazo[4,5-c]pyridin-6-yl]oxy}phenyl)-1-methyl-4-piperidinecarboxamide;

4-{2-(4-Amino-furazan-3-yl)-6-[(3-aminophenyl)oxy]-1H-imidazo[4,5-c]pyridin-1-yl}phenyl 4-(methyloxy)benzoate;

N-(3-{[2-(4-Amino-furazan-3-yl)-1-(4-hydroxyphenyl)-1H-imidazo[4,5-c]pyridin-6-yl]oxy}phenyl)-4-(dimethylamino)butanamide;

4-{2-(4-Amino-furazan-3-yl)-6-[(3-aminophenyl)oxy]-1H-imidazo[4,5-c]pyridin-1-yl}phenyl 2-methylpropanoate;

N'-(3-{[2-(4-Amino-furazan-3-yl)-1-(4-hydroxyphenyl)-1H-imidazo[4,5-c]pyridin-6-yl]oxy}phenyl)-N,N-dimethylsulfamide;

N-(3-{[2-(4-Amino-furazan-3-yl)-1-(4-{[2-(dimethylamino)ethyl]oxy}phenyl)-1H-imidazo[4,5-c]pyridin-6-yl]oxy}phenyl)-4-(methyloxy)benzamide;

N-(3-{[2-(4-Amino-furazan-3-yl)-1-(4-hydroxyphenyl)-1H-imidazo[4,5-c]pyridin-6-yl]oxy}phenyl)methanesulfonamide;

N-(3-{[2-(4-Amino-furazan-3-yl)-1-ethyl-1H-imidazo[4,5-c]pyridin-6-yl]oxy}phenyl)-3,4-bis(methyloxy)benzamide;

N-(3-{[2-(4-Amino-furazan-3-yl)-1-ethyl-1H-imidazo[4,5-c]pyridin-6-yl]oxy}phenyl)-2,3-dihydro-1-benzofuran-5-carboxamide;

N-(3-{[2-(4-Amino-furazan-3-yl)-1-ethyl-1H-imidazo[4,5-c]pyridin-6-yl]oxy}phenyl)-4-chloro-2-pyridinecarboxamide;

N-(3-{[2-(4-Amino-furazan-3-yl)-1-(4-{[2-(dimethylamino)ethyl]oxy}phenyl)-1H-imidazo[4,5-c]pyridin-6-yl]oxy}phenyl)-6-methyl-3-pyridinecarboxamide;

N-(3-{[2-(4-Amino-furazan-3-yl)-1-ethyl-1H-imidazo[4,5-c]pyridin-6-yl]oxy}phenyl)-4-(dimethylamino)butanamide;

5-{[2-(4-Amino-furazan-3-yl)-1-ethyl-1H-imidazo[4,5-c]pyridin-6-yl]oxy}-1,3-dimethyl-1,3-dihydro-2H-benzimidazol-2-one;

3-{[2-(4-Amino-furazan-3-yl)-1-(4-fluorophenyl)-1H-imidazo[4,5-c]pyridin-6-yl]oxy}-N-[2-(4-morpholinyl)ethyl]benzamide;

3-{[2-(4-Amino-furazan-3-yl)-1-(4-fluorophenyl)-1H-imidazo[4,5-c]pyridin-6-yl]oxy}-N-[3-(4-methyl-1-piperazinyl)propyl]benzamide;

3-({2-(4-Amino-furazan-3-yl)-1-[4-(trifluoromethyl)phenyl]-1H-imidazo[4,5-c]pyridin-6-yl}oxy)-N-[2-(4-morpholinyl)ethyl]benzamide;

3-({2-(4-Amino-furazan-3-yl)-1-[4-(trifluoromethyl)phenyl]-1H-imidazo[4,5-c]pyridin-6-yl}oxy)-N-[3-(4-methyl-1-piperazinyl)propyl]benzamide;

N'-(3-{[2-(4-Amino-furazan-3-yl)-1-(4-{[2-(dimethylamino)ethyl]oxy}phenyl)-1H-imidazo[4,5-c]pyridin-6-yl]oxy}phenyl)-N,N-dimethylsulfamide;

N-(3-{[2-(4-Amino-furazan-3-yl)-1-(4-{[2-(dimethylamino)ethyl]oxy}phenyl)-1H-imidazo[4,5-c]pyridin-6-yl]oxy}phenyl)-2-methylpropanamide;

Methyl 37-{[2-(4-amino-furazan-3-yl)-1-(phenylmethyl)-1H-imidazo[4,5-c]pyridin-6-yl]oxy}benzoate;

3-{[2-(4-Amino-furazan-3-yl)-1-(phenylmethyl)-1H-imidazo[4,5-c]pyridin-6-yl]oxy}benzoic acid;

3-{[2-(4-Amino-furazan-3-yl)-1-(phenylmethyl)-1H-imidazo[4,5-c]pyridin-6-yl]oxy}-N-[2-(4-morpholinyl)ethyl]benzamide;

N-(3-{[2-(4-Amino-furazan-3-yl)-1-(4-{[2-(dimethylamino)ethyl]oxy}phenyl)-1H-imidazo[4,5-c]pyridin-6-yl]oxy}phenyl)-N'-methylurea;

3-{[2-(4-Amino-furazan-3-yl)-1-(4-fluorophenyl)-1H-imidazo[4,5-c]pyridin-6-yl]oxy}-N-[3-(2-oxo-1-pyrrolidinyl)propyl]benzamide;

3-({2-(4-Amino-furazan-3-yl)-1-[4-(trifluoromethyl)phenyl]-1H-imidazo[4,5-c]pyridin-6-yl}oxy)-N-[3-(2-oxo-1-pyrrolidinyl)propyl]benzamide;

3-{[2-(4-Amino-furazan-3-yl)-1-phenyl-1H-imidazo[4,5-c]pyridin-6-yl]oxy}-N-{[4-(methyloxy)phenyl]methyl}benzamide;

3-{[2-(4-Amino-furazan-3-yl)-1-phenyl-1H-imidazo[4,5-c]pyridin-6-yl]oxy}-N-[4-(methyloxy)phenyl]benzamide;

3-{[2-(4-Amino-furazan-3-yl)-1-phenyl-1H-imidazo[4,5-c]pyridin-6-yl]oxy}-N-[4-(dimethylamino)phenyl]benzamide;

3-{[2-(4-Amino-furazan-3-yl)-1-phenyl-1H-imidazo[4,5-c]pyridin-6-yl]oxy}-N-[3-(dimethylamino)phenyl]benzamide;

N-(3-{[2-(4-Amino-furazan-3-yl)-1-phenyl-1H-imidazo[4,5-c]pyridin-6-yl]oxy}phenyl)-4-(dimethylamino)benzamide;

N-(3-{[2-(4-Amino-furazan-3-yl)-1-phenyl-1H-imidazo[4,5-c]pyridin-6-yl]oxy}phenyl)-4-(methyloxy)benzamide;

3-{[2-(4-Amino-furazan-3-yl)-1-ethyl-1H-imidazo[4,5-c]pyridin-6-yl]oxy}-N-[3-(2-oxo-1-pyrrolidinyl)propyl]benzamide;

3-{[2-(4-Amino-furazan-3-yl)-1-ethyl-1H-imidazo[4,5-c]pyridin-6-yl]oxy}-N-[2-(4-morpholinyl)ethyl]benzamide;

3-{[2-(4-Amino-furazan-3-yl)-1-ethyl-1H-imidazo[4,5-c]pyridin-6-yl]oxy}-N-[3-(4-methyl-1-piperazinyl)propyl]benzamide;

4-(Aminomethyl)-N-(3-{[2-(4-amino-furazan-3-yl)-1-ethyl-1H-imidazo[4,5-c]pyridin-6-yl]oxy}phenyl)benzamide;

N-(3-{[2-(4-Amino-furazan-3-yl)-1-ethyl-1H-imidazo[4,5-c]pyridin-6-yl]oxy}phenyl)-3-(3-pyridinyl)propanamide;

4-(Aminomethyl)-N-(3-{[2-(4-amino-furazan-3-yl)-1-phenyl-1H-imidazo[4,5-c]pyridin-6-yl]oxy}phenyl)benzamide;

Methyl 3-{[2-(4-amino-furazan-3-yl)-1H-imidazo[4,5-c]pyridin-6-yl]oxy}benzoate;

3-{[2-(4-amino-furazan-3-yl)-1-ethyl-1H-imidazo[4,5-c]pyridin-6-yl]oxy}-N-[4-(dimethylamino)phenyl]benzamide;

3-{[2-(4-Amino-furazan-3-yl)-1-ethyl-1H-imidazo[4,5-c]pyridin-6-yl]oxy}-N-[4-(4-morpholinyl)phenyl]benzamide;

3-{[2-(4-Amino-furazan-3-yl)-1-ethyl-1H-imidazo[4,5-c]pyridin-6-yl]oxy}-N-[4-(methyloxy)phenyl]benzamide;

N-(3-{[2-(4-Amino-furazan-3-yl)-1-phenyl-1H-imidazo[4,5-c]pyridin-6-yl]oxy}phenyl)-3-(4-morpholinyl)propanamide;

3-({2-(4-Amino-furazan-3-yl)-1-[2-(4-morpholinyl)ethyl]-1H-imidazo[4,5-c]pyridin-6-yl}oxy)benzoic acid;

3-({2-(4-Amino-furazan-3-yl)-1-[2-(4-morpholinyl)ethyl]-1H-imidazo[4,5-c]pyridin-6-yl}oxy)-N-[3-(2-oxo-1-pyrrolidinyl)propyl]benzamide;

3-({2-(4-Amino-furazan-3-yl)-1-[2-(4-morpholinyl)ethyl]-1H-imidazo[4,5-c]pyridin-6-yl}oxy)-N-[3-(4-methyl-1-piperazinyl)propyl]benzamide;

4-{1-Ethyl-6-[(3-{[3-(4-morpholinyl)propyl]oxy}phenyl)oxy]-1H-imidazo[4,5-c]pyridin-2-yl}-furazan-3-amine;

1-{3-[(3-{[2-(4-Amino-furazan-3-yl)-1-ethyl-1H-imidazo[4,5-c]pyridin-6-yl]oxy}phenyl)oxy]propyl}-2-pyrrolidinone;

4-{6-[(3-{[3-(4-Acetyl-1-piperazinyl)propyl]oxy}phenyl)oxy]-1-ethyl-1H-imidazo[4,5-c]pyridin-2-yl}-furazan-3-amine;

1-(3-{[2-(4-Amino-furazan-3-yl)-1-ethyl-1H-imidazo[4,5-c]pyridin-6-yl]oxy}phenyl)-4-(4-morpholinyl)-1-butanone;

3-{[2-(4-Amino-furazan-3-yl)-1H-imidazo[4,5-c]pyridin-6-yl]oxy}-N-[2-(4-morpholinyl)ethyl]benzamide;

3-({2-(4-Amino-furazan-3-yl)-1-[2-(methyloxy)phenyl]-1H-imidazo[4,5-c]pyridin-6-yl}oxy)-N-[3-(2-oxo-1-pyrrolidinyl)propyl]benzamide;

3-({2-(4-Amino-furazan-3-yl)-1-[2-(methyloxy)phenyl]-1H-imidazo[4,5-c]pyridin-6-yl}oxy)-N-[3-(4-methyl-1-piperazinyl)propyl]benzamide;

3-({2-(4-Amino-furazan-3-yl)-1-[2-(methyloxy)phenyl]-1H-imidazo[4,5-c]pyridin-6-yl}oxy)-N-[2-(4-morpholinyl)ethyl]benzamide;

3-{[2-(4-Amino-furazan-3-yl)-1-ethyl-1H-imidazo[4,5-c]pyridin-6-yl]oxy}-N-(4-{[2-(4-morpholinyl)ethyl]oxy}phenyl)benzamide;

3-{[2-(4-Amino-furazan-3-yl)-1-phenyl-1H-imidazo[4,5-c]pyridin-6-yl]oxy}-N-[2-(4-morpholinyl)ethyl]benzenesulfonamide;

N-(3-{[2-(4-Amino-furazan-3-yl)-1-ethyl-1H-imidazo[4,5-c]pyridin-6-yl]oxy}phenyl)-3-(3-hydroxyphenyl)propanamide;

N-(3-{[2-(4-Amino-furazan-3-yl)-1-ethyl-1H-imidazo[4,5-c]pyridin-6-yl]oxy}phenyl)-3-(4-hydroxyphenyl)propanamide;

N-(3-{[2-(4-Amino-furazan-3-yl)-1-ethyl-1H-imidazo[4,5-c]pyridin-6-yl]oxy}phenyl)-4-(2-oxo-1-pyrrolidinyl)butanamide;

3-({2-(4-Amino-furazan-3-yl)-1-[2-(methyloxy)ethyl]-1H-imidazo[4,5-c]pyridin-6-yl}oxy)-N-[3-(2-oxo-1-pyrrolidinyl)propyl]benzamide;

3-({2-(4-Amino-furazan-3-yl)-1-[2-(methyloxy)ethyl]-1H-imidazo[4,5-c]pyridin-6-yl}oxy)-N-[2-(4-morpholinyl)ethyl]benzamide;

3-{[2-(4-Amino-furazan-3-yl)-1-ethyl-1H-imidazo[4,5-c]pyridin-6-yl]oxy}-N-{2-[4-hydroxy-3-(methyloxy)phenyl]ethyl}benzamide;

N-(3-{[2-(4-Amino-furazan-3-yl)-1-phenyl-1H-imidazo[4,5-c]pyridin-6-yl]oxy}phenyl)-3-(2-oxo-1-pyrrolidinyl)propanamide;

N-(3-{[2-(4-Amino-furazan-3-yl)-1-phenyl-1H-imidazo[4,5-c]pyridin-6-yl]oxy}phenyl)-4-(2-oxo-1-pyrrolidinyl)butanamide;

3-{[2-(4-Amino-furazan-3-yl)-1-(cyclopropylmethyl)-1H-imidazo[4,5-c]pyridin-6-yl]oxy}-N-[2-(4-morpholinyl)ethyl]benzamide;

3-{[2-(4-Amino-furazan-3-yl)-1-ethyl-1H-imidazo[4,5-c]pyridin-6-yl]oxy}-N-(4-piperidinylmethyl)benzamide;

3-{[2-(4-Amino-furazan-3-yl)-1-ethyl-1H-imidazo[4,5-c]pyridin-6-yl]oxy}-N-[2-(4-piperidinyl)ethyl]benzamide;

N-(3-{[2-(4-Amino-furazan-3-yl)-1-phenyl-1H-imidazo[4,5-c]pyridin-6-yl]oxy}phenyl)-4-{[2-(4-morpholinyl)ethyl]oxy}benzamide;

N-[2-(4-Acetyl-1-piperazinyl)ethyl]-3-{[2-(4-amino-furazan-3-yl)-1-ethyl-1H-imidazo[4,5-c]pyridin-6-yl]oxy}benzamide;

3-{[2-(4-Amino-furazan-3-yl)-1-ethyl-1H-imidazo[4,5-c]pyridin-6-yl]oxy}-N-[3-(4-methyl-1-piperazinyl)-3-oxopropyl]benzamide;

3-{[2-(4-Amino-furazan-3-yl)-1 ethyl-1H-imidazo[4,5-c]pyridin-6-yl]oxy}-N-(4-{[2-(dimethylamino)ethyl]oxy}phenyl)benzamide; and N-(3-{[2-(4-Amino-furazan-3-yl)-1-(cyclopropylmethyl)-1H-imidazo[4,5-c]pyridin-6-yl]oxy}phenyl)-4-{[2-(4-morpholinyl)ethyl]oxy}benzamide;

3-{[2-(4-Amino-furazan-3-yl)-1-ethyl-1H-imidazo[4,5-c]pyridin-6-yl]oxy}-N-(4-{[3-(dimethylamino)propyl]oxy}phenyl)benzamide;

N-(3-{[2-(4-Amino-furazan-3-yl)-1-ethyl-1H-imidazo[4,5-c]pyridin-6-yl]oxy}phenyl)-4-{[3-(1-piperidinyl)propyl]oxy}benzamide;

N-(3-{[2-(4-Amino-furazan-3-yl)-1-ethyl-1H-imidazo[4,5-c]pyridin-6-yl]oxy}phenyl)-4-{[2-(diethylamino)ethyl]oxy}benzamide;

N-(3-{[2-(4-Amino-furazan-3-yl)-1-ethyl-1H-imidazo[4,5-c]pyridin-6-yl]oxy}phenyl)-4-{[2-(1-pyrrolidinyl)ethyl]oxy}benzamide;

N-(3-{[2-(4-Amino-furazan-3-yl)-1-ethyl-1H-imidazo[4,5-c]pyridin-6-yl]oxy}phenyl)-4-({2-[bis(1-methylethyl)amino]ethyl}oxy)benzamide;

N-(3-{[2-(4-Amino-furazan-3-yl)-1-ethyl-1H-imidazo[4,5-c]pyridin-6-yl]oxy}phenyl)-4-{[2-(1-piperidinyl)ethyl]oxy}benzamide;

N-(3-{[2-(4-Amino-furazan-3-yl)-1-ethyl-1H-imidazo[4,5-c]pyridin-6-yl]oxy}phenyl)-4-hydroxybenzamide;

N-[4-(Acetylamino)phenyl]-3-{[2-(4-amino-furazan-3-yl)-1-ethyl-1H-imidazo[4,5-c]pyridin-6-yl]oxy}benzamide;

3-{[2-(4-Amino-furazan-3-yl)-1-ethyl-1H-imidazo[4,5-c]pyridin-6-yl]oxy}-N-(2-oxo-2-phenylethyl)benzamide;

N-[4-(Aminocarbonyl)phenyl]-3-{[2-(4-amino-furazan-3-yl)-1-ethyl-1H-imidazo[4,5-c]pyridin-6-yl]oxy}benzamide;

3-{[2-(4-Amino-furazan-3-yl)-1-ethyl-1H-imidazo[4,5-c]pyridin-6-yl]oxy}-N-[2-hydroxy-2-(4-hydroxyphenyl)ethyl]benzamide;

3-{[2-(4-Amino-furazan-3-yl)-1-(6-methyl-2-pyridinyl)-1H-imidazo[4,5-c]pyridin-6-yl]oxy}-N-[3-(2-oxo-1-pyrrolidinyl)propyl]benzamide;

3-{[2-(4-Amino-furazan-3-yl)-1-(6-methyl-2-pyridinyl)-1H-imidazo[4,5-c]pyridin-6-yl]oxy}-N-[2-(4-morpholinyl)ethyl]benzamide;

N-(3-{[2-(4-Amino-furazan-3-yl)-1-ethyl-1H-imidazo[4,5-c]pyridin-6-yl]oxy}phenyl)-6-{[2-(4-morpholinyl)ethyl]oxy}-3-pyridinecarboxamide;

4-{1-Ethyl-6-[(3-{[2-(4-morpholinyl)ethyl]oxy}phenyl)oxy]-1H-imidazo[4,5-c]pyridin-2-yl}-furazan-3-amine;

3-{[2-(4-Amino-furazan-3-yl)-1-ethyl-1H-imidazo[4,5-c]pyridin-6-yl]oxy}-N-[2-(4-thiomorpholinyl)ethyl]benzamide;

3-{[2-(4-Amino-furazan-3-yl)-1-ethyl-1H-imidazo[4,5-c]pyridin-6-yl]oxy}-N-[2-(tetrahydro-2H-pyran-4-yl)ethyl]benzamide;

N-(3-{[2-(4-Amino-furazan-3-yl)-1-ethyl-1H-imidazo[4,5-c]pyridin-6-yl]oxy}phenyl)-4-{[3-(1-piperazinyl)propyl]oxy}benzamide;

3-{[2-(4-Amino-furazan-3-yl)-1-ethyl-1H-imidazo[4,5-c]pyridin-6-yl]oxy}-N-[2-(1,1-dioxido-4-thiomorpholinyl)ethyl]benzamide;

3-{[2-(4-Amino-furazan-3-yl)-1-ethyl-1H-imidazo[4,5-c]pyridin-6-yl]oxy}-N-[2-(1-oxido-4-thiomorpholinyl)ethyl]benzamide;

3-{[2-(4-Amino-furazan-3-yl)-1-ethyl-1H-imidazo[4,5-c]pyridin-6-yl]oxy}-N-[3-(1-piperidinyl)propyl]benzamide;

N-(3-{[2-(4-Amino-furazan-3-yl)-1-ethyl-1H-imidazo[4,5-c]pyridin-6-yl]oxy}phenyl)-4-[(1-methyl-4-piperidinyl)oxy]benzamide;

N-(3-{[2-(4-Amino-furazan-3-yl)-1-ethyl-1H-imidazo[4,5-c]pyridin-6-yl]oxy}phenyl)-3-(4-piperidinyl)propanamide;

N-(3-{[2-(4-Amino-furazan-3-yl)-1-ethyl-1H-imidazo[4,5-c]pyridin-6-yl]oxy}phenyl)-4-{[2-(1-piperazinyl)ethyl]oxy}benzamide;

1-(3-{[2-(4-Amino-furazan-3-yl)-1-ethyl-1H-imidazo[4,5-c]pyridin-6-yl]oxy}phenyl)-4-(4-morpholinyl)-1-butanol;

4-[1-Ethyl-6-({3-[(1E)-3-(4-methyl-1-piperazinyl)-3-oxo-1-propen-1-yl]phenyl}oxy)-1H-imidazo[4,5-c]pyridin-2-yl]-furazan-3-amine;

4-[1-Ethyl-6-(f{3-[3-(4-methyl-1-piperazinyl)-3-oxopropyl]
phenyl}oxy)-1H-imidazo[4,5-c]pyridin-2-yl]-furazan-3-
amine;
3-({2-(4-Amino-furazan-3-yl)-1-[2-(methyloxy)ethyl]-1H-
imidazo[4,5-c]pyridin-6-yl}oxy)-N-[3-(4-methyl-1-pip-
erazinyl)-3-oxopropyl]benzamide;
3-{[2-(4-Amino-furazan-3-yl)-1-(4-fluorophenyl)-1H-imi-
dazo[4,5-c]pyridin-6-yl]oxy}-N-[3-(4-methyl-1-piperazi-
nyl)-3-oxopropyl]benzamide;
1-(3-{[2-(4-Amino-furazan-3-yl)-1-ethyl-1H-imidazo[4,5-
c]pyridin-6-yl]oxy}phenyl)-2-methyl-4-(4-morpholinyl)-
1-butanone;
3-{[2-(4-Amino-furazan-3-yl)-1-ethyl-1H-imidazo[4,5-c]
pyridin-6-yl]oxy}-N-{4-[(1,1-dioxido-4-thiomorpholi-
nyl)methyl]phenyl}benzamide;
1-(3-{[2-(4-Amino-furazan-3-yl)-1-ethyl-1H-imidazo[4,5-
c]pyridin-6-yl]oxy}phenyl)-4-(4-methyl-1-piperazinyl)-
4-oxo-1-butanone;
4-(1-(1,2,3,4-Tetrahydro-7-isoquinolinyl)-6-{[4-(trifluo-
romethyl)phenyl]oxy}-1H-imidazo[4,5-c]pyridin-2-yl)-
furazan-3-amine;
N-(3-{[2-(4-Amino-furazan-3-yl)-1-(4-{[2-(4-morpholinyl)
ethyl]oxy}phenyl)-1H-imidazo[4,5-c]pyridin-6-yl]
oxy}phenyl)acetamide;
N-(3-{[2-(4-Amino-furazan-3-yl)-1-(4-{[2-(4-morpholinyl)
ethyl]oxy}phenyl)-1H-imidazo[4,5-c]pyridin-6-yl]
oxy}phenyl)acetamide;
3-({2-(4-Amino-furazan-3-yl)-1-[3-(methyloxy)propyl]-
1H-imidazo[4,5-c]pyridin-6-yl}oxy)-N-[3-(2-oxo-1-pyr-
rolidinyl)propyl]benzamide;
3-({2-(4-Amino-furazan-3-yl)-1-[3-(methyloxy)propyl]-
1H-imidazo[4,5-c]pyridin-6-yl}oxy)-N-[2-(4-morpholi-
nyl)ethyl]benzamide;
3-{[2-(4-Amino-furazan-3-yl)-1-(2-methyl-4-pyridinyl)-
1H-imidazo[4,5-c]pyridin-6-yl]oxy}-N-[2-(4-morpholi-
nyl)ethyl]benzamide;
Methyl 3-{[2-(4-amino-furazan-3-yl)-1-(1,3-benzodioxol-5-
yl)-1H-imidazo[4,5-c]pyridin-6-yl]oxy}benzoate;
3-{[2-(4-Amino-furazan-3-yl)-1-(1,3-benzodioxol-5-yl)-
1H-imidazo[4,5-c]pyridin-6-yl]oxy}-N-[3-(2-oxo-1-pyr-
rolidinyl)propyl]benzamide;
Methyl 3-{[2-(4-amino-furazan-3-yl)-1-(1H-indazol-5-yl)-
1H-imidazo[4,5-c]pyridin-6-yl]oxy}benzoate;
3-{[2-(4-Amino-furazan-3-yl)-1-(1H-indazol-5-yl)-1H-imi-
dazo[4,5-c]pyridin-6-yl]oxy}-N-[3-(2-oxo-1-pyrrolidi-
nyl)propyl]benzamide;
N-(3-{[2-(4-Amino-furazan-3-yl)-1-(4-{[2-(1-pyrrolidinyl)
ethyl]oxy}phenyl)-1H-imidazo[4,5-c]pyridin-6-yl]
oxy}phenyl)acetamide;
3-({2-(4-Amino-furazan-3-yl)-1-[2-(dimethylamino)ethyl]-
1H-imidazo[4,5-c]pyridin-6-yl}oxy)-N-[3-(2-oxo-1-pyr-
rolidinyl)propyl]benzamide;
Methyl 3-{[2-(4-amino-furazan-3-yl)-1-(4-piperidinyl)-1H-
imidazo[4,5-c]pyridin-6-yl]oxy}benzoate;
Methyl 3-{[2-(4-amino-furazan-3-yl)-1-(4-bromophenyl)-
1H-imidazo[4,5-c]pyridin-6-yl]oxy}benzoate;
Methyl 3-{[2-(4-amino-furazan-3-yl)-1-(1H-benzimidazol-
5-yl)-1H-imidazo[4,5-c]pyridin-6-yl]oxy}benzoate;
N-(3-{[2-(4-Amino-furazan-3-yl)-1-ethyl-1H-imidazo[4,5-
c]pyridin-6-yl]oxy}phenyl)-4-(4-morpholinylmethyl)
benzamide;
N-[3-{[2-(4-Amino-furazan-3-yl)-1-ethyl-1H-imidazo[4,5-
c]pyridin-6-yl]oxy}-5-(trifluoromethyl)phenyl]aceta-
mide;
4-(6-{[3-Amino-5-(trifluoromethyl)phenyl]oxy}-1-ethyl-
1H-imidazo[4,5-c]pyridin-2-yl)-furazan-3-amine;
3-{[2-(4-Amino-furazan-3-yl)-1-phenyl-1H-imidazo[4,5-c]
pyridin-6-yl]oxy}-N-[3-(dimethylamino)propyl]-N-me-
thylbenzamide;
N-(3-{[2-(4-Amino-furazan-3-yl)-1-(4-{[2-(diethylamino)
ethyl]oxy}phenyl)-1H-imidazo[4,5-c]pyridin-6-yl]
oxy}phenyl)acetamide;
3-{[2-(4-Amino-furazan-3-yl)-1-ethyl-1H-imidazo[4,5-c]
pyridin-6-yl]oxy}-N-{4-[(dimethylamino)methyl]
phenyl}benzamide;
3-{[2-(4-Amino-furazan-3-yl)-1-ethyl-1H-imidazo[4,5-c]
pyridin-6-yl]oxy}-N-{4-[2-(dimethylamino)ethyl]
phenyl}benzamide;
3-{[2-(4-Amino-furazan-3-yl)-1-ethyl-1H-imidazo[4,5-c]
pyridin-6-yl]oxy}-N-{4-[2-(1-pyrrolidinyl)ethyl]
phenyl}benzamide;
3-{[2-(4-Amino-furazan-3-yl)-1-ethyl-1H-imidazo[4,5-c]
pyridin-6-yl]oxy}-N-[3-(1-methyl-4-piperidinyl)propyl]
benzamide;
3-{[2-(4-Amino-furazan-3-yl)-1-ethyl-1H-imidazo[4,5-c]
pyridin-6-yl]oxy}-N-methyl-N-[3-(1-methyl-4-piperidi-
nyl)propyl]benzamide;
3-{[2-(4-Amino-furazan-3-yl)-1-(4-piperidinyl)-1H-imi-
dazo[4,5-c]pyridin-6-yl]oxy}-N-[3-(2-oxo-1-pyrrolidi-
nyl)propyl]benzamide;
3-{[2-(4-Amino-furazan-3-yl)-1-(4-bromophenyl)-1H-imi-
dazo[4,5-c]pyridin-6-yl]oxy}-N-[3-(2-oxo-1-pyrrolidi-
nyl)propyl]benzamide;
3-{[2-(4-Amino-furazan-3-yl)-1-(1H-benzimidazol-5-yl)-
1H-imidazo[4,5-c]pyridin-6-yl]oxy}-N-[3-(2-oxo-1-pyr-
rolidinyl)propyl]benzamide;
3-{[2-(4-Amino-furazan-3-yl)-1-(4-bromophenyl)-1H-imi-
dazo[4,5-c]pyridin-6-yl]oxy}-N-[3-(4-methyl-1-piperazi-
nyl)-3-oxopropyl]benzamide;
3-{[2-(4-Amino-furazan-3-yl)-1-(4-piperidinyl)-1H-imi-
dazo[4,5-c]pyridin-6-yl]oxy}-N-[3-(4-methyl-1-piperazi-
nyl)-3-oxopropyl]benzamide;
4-(1-(4-{[2-(Dimethylamino)ethyl]oxy}phenyl)-6-{[3-(me-
thylsulfonyl)phenyl]oxy}-1H-imidazo[4,5-c]pyridin-2-
yl)-furazan-3-amine;
3-{[2-(4-Amino-furazan-3-yl)-1-(4-fluorophenyl)-1H-imi-
dazo[4,5-c]pyridin-6-yl]oxy}-N-[3-(1-methyl-4-piperidi-
nyl)propyl]benzamide;
N-(3-{[2-(4-Amino-furazan-3-yl)-1-ethyl-1H-imidazo[4,5-
c]pyridin-6-yl]oxy}phenyl)-4-[(dimethylamino)methyl]
benzamide;
N-[3-({2-(4-Amino-furazan-3-yl)-1-[2-(methyloxy)ethyl]-
1H-imidazo[4,5-c]pyridin-6-yl}oxy)phenyl]acetamide;
3-{[2-(4-Amino-furazan-3-yl)-1-ethyl-1H-imidazo[4,5-c]
pyridin-6-yl]oxy}-N-[2-(4-methyl-1-piperazinyl)ethyl]
benzamide;
N-[3-({2-(4-Amino-furazan-3-yl)-1-[3-(methyloxy)propyl]-
1H-imidazo[4,5-c]pyridin-6-yl}oxy)phenyl]acetamide;
4-{1-Ethyl-6-[(3-{[3-(1-methyl-4-piperidinyl)propyl]
oxy}phenyl)oxy]-1H-imidazo[4,5-c]pyridin-2-yl}-fura-
zan-3-amine;
3-{[2-(4-Amino-furazan-3-yl)-1-(1,2,3,4-tetrahydro-7-iso-
quinolinyl)-1H-imidazo[4,5-c]pyridin-6-yl]oxy}-N-[3-
(2-oxo-1-pyrrolidinyl)propyl]benzamide;
N-(3-{[2-(4-Amino-furazan-3-yl)-1-(4-{[2-(1-piperidinyl)
ethyl]oxy}phenyl)-1H-imidazo[4,5-c]pyridin-6-yl]
oxy}phenyl)acetamide;
N-{3-[(2-(4-Amino-furazan-3-yl)-1-(4-{[(cyanomethyl)oxy]
phenyl}-1H-imidazo[4,5-c]pyridin-6-yl)oxy]phenyl}ac-
etamide;
4-(1-Ethyl-6-{[3-(1H-imidazol-1-yl)phenyl]oxy}-1H-imi-
dazo[4,5-c]pyridin-2-yl)-furazan-3-amine;

4-(1-Ethyl-6-{[3-(1,3-thiazol-5-yl)phenyl]oxy}-1H-imidazo[4,5-c]pyridin-2-yl)-furazan-3-amine;
4-(1-Ethyl-6-{[3-(1,3-oxazol-5-yl)phenyl]oxy}-1H-imidazo[4,5-c]pyridin-2-yl)-furazan-3-amine;
4-(1-Ethyl-6-{[3-(methylsulfonyl)phenyl]oxy}-1H-imidazo[4,5-c]pyridin-2-yl)-furazan-3-amine;
N~1~-(3-{[2-(4-Amino-furazan-3-yl)-1-ethyl-1H-imidazo[4,5-c]pyridin-6-yl]oxy}phenyl)-N~3~,N~3~-dimethyl-beta-alaninamide;
N-(3-{[2-(4-Amino-furazan-3-yl)-1-ethyl-1H-imidazo[4,5-c]pyridin-6-yl]oxy}phenyl)-4-(4-morpholinyl)butanamide;
N-(3-{[2-(4-Amino-furazan-3-yl)-1-ethyl-1H-imidazo[4,5-c]pyridin-6-yl]oxy}phenyl)-4-(diethylamino)butanamide;
N-(3-{[2-(4-Amino-furazan-3-yl)-1-ethyl-1H-imidazo[4,5-c]pyridin-6-yl]oxy}phenyl)-4-(methylamino)butanamide;
N-(5-{[2-(4-Amino-furazan-3-yl)-1-ethyl-1H-imidazo[4,5-c]pyridin-6-yl]oxy}-2-methylphenyl)acetamide;
N-(5-{[2-(4-Amino-furazan-3-yl)-1-ethyl-1H-imidazo[4,5-c]pyridin-6-yl]oxy}-2-chlorophenyl)acetamide;
4-{1-Ethyl-6-[(3-{[2-(1-methyl-4-piperidinyl)ethyl]oxy}phenyl)oxy]-1H-imidazo[4,5-c]pyridin-2-yl}-furazan-3-amine;
4-{1-Ethyl-6-[(3-{[4-(1-methyl-4-piperidinyl)butyl]oxy}phenyl)oxy]-1H-imidazo[4,5-c]pyridin-2-yl}-furazan-3-amine;
4-{1-(2,3-Dihydro-1H-isoindol-5-yl)-6-[(4-fluorophenyl)oxy]-1H-imidazo[4,5-c]pyridin-2-yl}-furazan-3-amine;
4-{1-Ethyl-6-[(3-{[(1-methyl-4-piperidinyl)methyl]oxy}phenyl)oxy]-1H-imidazo[4,5-c]pyridin-2-yl}-furazan-3-amine;
4-{1-Ethyl-6-[(3-{[(1-methyl-3-piperidinyl)methyl]oxy}phenyl)oxy]-1H-imidazo[4,5-c]pyridin-2-yl}-furazan-3-amine;
4-{1-Ethyl-6-[(3-{[2-(1-methyl-3-piperidinyl)ethyl]oxy}phenyl)oxy]-1H-imidazo[4,5-c]pyridin-2-yl}-furazan-3-amine;
Methyl 3-{[2-(4-amino-furazan-3-yl)-1-(2-methyl-1,3-benzoxazol-5-yl)-1H-imidazo[4,5-c]pyridin-6-yl]oxy}benzoate;
4-[1-Ethyl-6-({3-[4-(1-methyl-4-piperidinyl)butyl]phenyl}oxy)-1H-imidazo[4,5-c]pyridin-2-yl]-furazan-3-amine;
Methyl 3-{[2-(4-amino-furazan-3-yl)-1-ethyl-1H-imidazo[4,5-c]pyridin-6-yl]methyl}benzoate
3-{[2-(4-Amino-furazan-3-yl)-1-ethyl-1H-imidazo[4,5-c]pyridin-6-yl]methyl}-N-[2-(4-morpholinyl)ethyl]benzamide;
1-(3-{[2-(4-Amino-furazan-3-yl)-1-(1,2,3,4-tetrahydro-7-isoquinolinyl)-1H-imidazo[4,5-c]pyridin-6-yl]oxy}phenyl)ethanone.

Preferred Compound:
4-[1-Ethyl-6-(phenylthio)-1H-imidazo[4,5-c]pyridin-2-yl]-furazan-3-amine;
4-{1-Ethyl-6-[(4-fluorophenyl)thio]-1H-imidazo[4,5-c]pyridin-2-yl}-furazan-3-amine;
4-[1-Ethyl-6-(2-pyridinylthio)-1H-imidazo[4,5-c]pyridin-2-yl]-furazan-3-amine;
4-(1-Ethyl-6-{[3-(methyloxy)phenyl]thio}-1H-imidazo[4,5-c]pyridin-2-yl)-furazan-3-amine;
4-[1-Ethyl-6-(phenylsulfinyl)-1H-imidazo[4,5-c]pyridin-2-yl]-furazan-3-amine;
4-{1-Ethyl-6-[(phenylmethyl)thio]-1H-imidazo[4,5-c]pyridin-2-yl}-furazan-3-amine;
4-(6-{[3,4-Bis(methyloxy)phenyl]thio}-1-ethyl-1H-imidazo[4,5-c]pyridin-2-yl)-furazan-3-amine;
3-{[2-(4-Amino-furazan-3-yl)-1-ethyl-1H-imidazo[4,5-c]pyridin-6-yl]thio}phenol;
Methyl 3-{[2-(4-amino-furazan-3-yl)-1-ethyl-1H-imidazo[4,5-c]pyridin-6-yl]thio}benzoate;
4-[1-Ethyl-6-(1,3-thiazol-2-ylthio)-1H-imidazo[4,5-c]pyridin-2-yl]-furazan-3-amine;
N-(3-{[2-(4-Amino-furazan-3-yl)-1-ethyl-1H-imidazo[4,5-c]pyridin-6-yl]thio}phenyl)acetamide;
4-[1-Ethyl-6-([1,3]thiazolo[4,5-b]pyridin-2-ylthio)-1H-imidazo[4,5-c]pyridin-2-yl]-furazan-3-amine;
4-{[2-(4-Amino-furazan-3-yl)-1-ethyl-1H-imidazo[4,5-c]pyridin-6-yl]thio}benzoic acid;
N-(2-{[2-(4-Amino-furazan-3-yl)-1-ethyl-1H-imidazo[4,5-c]pyridin-6-yl]thio}ethyl)acetamide;
4-[1-Ethyl-6-(1H-imidazol-2-ylthio)-1H-imidazo[4,5-c]pyridin-2-yl]-furazan-3-amine;
3-{[2-(4-Amino-furazan-3-yl)-1-ethyl-1H-imidazo[4,5-c]pyridin-6-yl]thio}benzoic acid;
4-(1-Ethyl-6-{[4-(trifluoromethyl)phenyl]thio}-1H-imidazo[4,5-c]pyridin-2-yl)-furazan-3-amine;
4-{6-[(3,4-Dichlorophenyl)thio]-1-ethyl-1H-imidazo[4,5-c]pyridin-2-yl}-furazan-3-amine;
4-{6-[(3-Chloro-4-fluorophenyl)thio]-1-ethyl-1H-imidazo[4,5-c]pyridin-2-yl}-furazan-3-amine;
Methyl 2-{[2-(4-amino-furazan-3-yl)-1-ethyl-1H-imidazo[4,5-c]pyridin-6-yl]thio}benzoate;
4-(1-Ethyl-6-{[2-(methyloxy)phenyl]thio}-1H-imidazo[4,5-c]pyridin-2-yl)-furazan-3-amine;
4-(1-Ethyl-6-{[4-(methylthio)phenyl]thio}-1H-imidazo[4,5-c]pyridin-2-yl)-furazan-3-amine;
4-(1-Ethyl-6-{[4-(methylsulfinyl)phenyl]sulfinyl}-1H-imidazo[4,5-c]pyridin-2-yl)-furazan-3-amine;
4-(1-Ethyl-6-{[4-(methylsulfonyl)phenyl]sulfinyl}-1H-imidazo[4,5-c]pyridin-2-yl)-furazan-3-amine;
4-(1-Ethyl-6-{[5-(methyloxy)-1,3-benzothiazol-2-yl]thio}-1H-imidazo[4,5-c]pyridin-2-yl)-furazan-3-amine;
4-[6-(Cyclopentylthio)-1-ethyl-1H-imidazo[4,5-c]pyridin-2-yl]-furazan-3-amine;
1-((2S)-3-{[2-(4-Amino-furazan-3-yl)-1-ethyl-1H-imidazo[4,5-c]pyridin-6-yl]thio}-2-methylpropanoyl)-L-proline;
4-{6-[(2,5-Dimethyl-3-furanyl)thio]-1-ethyl-1H-imidazo[4,5-c]pyridin-2-yl}-furazan-3-amine;
4-[1-Ethyl-6-(4-pyridinylthio)-1H-imidazo[4,5-c]pyridin-2-yl]-furazan-3-amine;
N-(3-{[2-(4-Amino-furazan-3-yl)-1-ethyl-1H-imidazo[4,5-c]pyridin-6-yl]thio}phenyl)ethanethioamide;
7-{[2-(4-Amino-furazan-3-yl)-1-ethyl-1H-imidazo[4,5-c]pyridin-6-yl]thio}-3-methyl-2H-chromen-2-one;
N-[5-{[2-(4-Amino-furazan-3-yl)-1-ethyl-1H-imidazo[4,5-c]pyridin-6-yl]thio}-2-(methyloxy)phenyl]acetamide;
Methyl (2E)-3-(4-{[2-(4-amino-furazan-3-yl)-1-ethyl-1H-imidazo[4,5-c]pyridin-6-yl]thio}phenyl)-2-propenoate;
3-{[2-(4-Amino-furazan-3-yl)-1-ethyl-1H-imidazo[4,5-c]pyridin-6-yl]oxy}-N-(4-{[3-(dimethylamino)propyl]oxy}phenyl)benzamide;
3-{[2-(4-Amino-furazan-3-yl)-1-ethyl-1H-imidazo[4,5-c]pyridin-6-yl]oxy}-N-{4-[2-(1-pyrrolidinyl)ethyl]phenyl}benzamide;
3-{[2-(4-Amino-furazan-3-yl)-1-ethyl-1H-imidazo[4,5-c]pyridin-6-yl]oxy}-N-{4-[(dimethylamino)methyl]phenyl}benzamide;
3-{[2-(4-Amino-furazan-3-yl)-1-ethyl-1H-imidazo[4,5-c]pyridin-6-yl]oxy}-N-{4-[2-(dimethylamino)ethyl]phenyl}benzamide;
N-(3-{[2-(4-Amino-furazan-3-yl)-1-ethyl-1H-imidazo[4,5-c]pyridin-6-yl]oxy}phenyl)-4-{[2-(dimethylamino)ethyl]oxy}benzamide;

3-{[2-(4-Amino-furazan-3-yl)-1-ethyl-1H-imidazo[4,5-c] pyridin-6-yl]oxy}-N-[3-(1-methyl-4-piperidinyl)propyl] benzamide;

3-{[2-(4-Amino-furazan-3-yl)-1-ethyl-1H-imidazo[4,5-c] pyridin-6-yl]oxy}-N-(4-{[2-(dimethylamino)ethyl] oxy}phenyl)benzamide;

N-(3-{[2-(4-Amino-furazan-3-yl)-1-ethyl-1H-imidazo[4,5-c]pyridin-6-yl]oxy}phenyl)-4-[(dimethylamino)methyl] benzamide;

N-(3-{[2-(4-Amino-furazan-3-yl)-1-ethyl-1H-imidazo[4,5-c]pyridin-6-yl]oxy}phenyl)-4-{[2-(diethylamino)ethyl] oxy}benzamide;

N-(3-{[2-(4-Amino-furazan-3-yl)-1-ethyl-1H-imidazo[4,5-c]pyridin-6-yl]oxy}phenyl)-4-({2-[bis(1-methylethyl) amino]ethyl}oxy)benzamide;

N-(3-{[2-(4-Amino-furazan-3-yl)-1-ethyl-1H-imidazo[4,5-c]pyridin-6-yl]oxy}phenyl)-4-{[2-(1-piperidinyl)ethyl] oxy}benzamide;

3-{[2-(4-Amino-furazan-3-yl)-1-ethyl-1H-imidazo[4,5-c] pyridin-6-yl]oxy}-N-[2-(4-methyl-1-piperazinyl)ethyl] benzamide;

3-{[2-(4-Amino-furazan-3-yl)-1-ethyl-1H-imidazo[4,5-c] pyridin-6-yl]oxy}-N-[3-(4-methyl-1-piperazinyl)propyl] benzamide;

3-{[2-(4-Amino-furazan-3-yl)-1-ethyl-1H-imidazo[4,5-c] pyridin-6-yl]oxy}-N-(4-{[2-(4-morpholinyl)ethyl] oxy}phenyl)benzamide;

N-(3-{[2-(4-Amino-furazan-3-yl)-1-ethyl-1H-imidazo[4,5-c]pyridin-6-yl]oxy}phenyl)-4-{[2-(1-pyrrolidinyl)ethyl] oxy}benzamide;

4-(Aminomethyl)-N-(3-{[2-(4-amino-furazan-3-yl)-1-ethyl-1H-imidazo[4,5-c]pyridin-6-yl]oxy}phenyl)benzamide;

N-(3-{[2-(4-Amino-furazan-3-yl)-1-ethyl-1H-imidazo[4,5-c]pyridin-6-yl]oxy}phenyl)-3-(3-pyridinyl)propanamide;

3-{[2-(4-Amino-furazan-3-yl)-1-ethyl-1H-imidazo[4,5-c] pyridin-6-yl]oxy}-N-[2-(4-piperidinyl)ethyl]benzamide;

3-{[2-(4-Amino-furazan-3-yl)-1-ethyl-1H-imidazo[4,5-c] pyridin-6-yl]oxy}-N-{2-[4-hydroxy-3-(methyloxy)phenyl]ethyl}benzamide;

3-{[2-(4-Amino-furazan-3-yl)-1-ethyl-1H-imidazo[4,5-c] pyridin-6-yl]oxy}-N-[4-(4-morpholinyl)phenyl]benzamide;

N-(3-{[2-(4-Amino-furazan-3-yl)-1-ethyl-1H-imidazo[4,5-c]pyridin-6-yl]oxy}phenyl)-3-(4-piperidinyl)propanamide;

3-{[2-(4-Amino-furazan-3-yl)-1-(4-fluorophenyl)-1H-imidazo[4,5-c]pyridin-6-yl]oxy}-N-[3-(1-methyl-4-piperidinyl)propyl]benzamide;

N-(3-{[2-(4-Amino-furazan-3-yl)-1-ethyl-1H-imidazo[4,5-c]pyridin-6-yl]oxy}phenyl)-1-methyl-1H-1,2,3-benzotriazole-5-carboxamide;

N-(3-{[2-(4-Amino-furazan-3-yl)-1-ethyl-1H-imidazo[4,5-c]pyridin-6-yl]oxy}phenyl)-3-(4-hydroxyphenyl)propanamide;

3-{[2-(4-Amino-furazan-3-yl)-1-ethyl-1H-imidazo[4,5-c] pyridin-6-yl]oxy}-N-(2-oxo-2-phenylethyl)benzamide;

1-(3-{[2-(4-Amino-furazan-3-yl)-1-ethyl-1H-imidazo[4,5-c]pyridin-6-yl]oxy}phenyl)-4-(4-methyl-1-piperazinyl)-4-oxo-1-butanone;

N-(3-{[2-(4-Amino-furazan-3-yl)-1-ethyl-1H-imidazo[4,5-c]pyridin-6-yl]oxy}phenyl)-4-(4-morpholinylmethyl) benzamide;

N-(3-{[2-(4-Amino-furazan-3-yl)-1-ethyl-1H-imidazo[4,5-c]pyridin-6-yl]oxy}phenyl)-4-{[2-(4-morpholinyl)ethyl] oxy}benzamide;

3-{[2-(4-Amino-furazan-3-yl)-1-ethyl-1H-imidazo[4,5-c] pyridin-6-yl]oxy}-N-[3-(4-methyl-1-piperazinyl)-3-oxo-propyl]benzamide;

N-[4-(Acetylamino)phenyl]-3-{[2-(4-amino-furazan-3-yl)-1-ethyl-1H-imidazo[4,5-c]pyridin-6-yl]oxy}benzamide;

3-{[2-(4-Amino-furazan-3-yl)-1-ethyl-1H-imidazo[4,5-c] pyridin-6-yl]oxy}-N-[4-(dimethylamino)phenyl]benzamide;

N-(3-{[2-(4-Amino-furazan-3-yl)-1-ethyl-1H-imidazo[4,5-c]pyridin-6-yl]oxy}phenyl)-3-pyridinecarboxamide;

4-[2-(4-Amino-furazan-3-yl)-6-(methyloxy)-1H-imidazo[4,5-c]pyridin-1-yl]phenol;

N-(3-{[2-(4-Amino-furazan-3-yl)-1-(4-hydroxyphenyl)-1H-imidazo[4,5-c]pyridin-6-yl]oxy}phenyl)-4-(dimethylamino)butanamide;

N-(3-{[2-(4-Amino-furazan-3-yl)-1-ethyl-1H-imidazo[4,5-c]pyridin-6-yl]oxy}phenyl)-4-(diethylamino)butanamide;

3-{[2-(4-Amino-furazan-3-yl)-1-phenyl-1H-imidazo[4,5-c] pyridin-6-yl]oxy}-N-[3-(4-methyl-1-piperazinyl)propyl] benzamide;

3-{[2-(4-Amino-furazan-3-yl)-1-ethyl-1H-imidazo[4,5-c] pyridin-6-yl]oxy}-N-[2-hydroxy-2-(4-hydroxyphenyl) ethyl]benzamide;

3-{[2-(4-Amino-furazan-3-yl)-1-ethyl-1H-imidazo[4,5-c] pyridin-6-yl]oxy}-N-[2-(tetrahydro-2H-pyran-4-yl)ethyl] benzamide;

N-(3-{[2-(4-Amino-furazan-3-yl)-1-ethyl-1H-imidazo[4,5-c]pyridin-6-yl]oxy}phenyl)-4-{[3-(1-piperidinyl)propyl] oxy}benzamide;

N-[4-(Aminocarbonyl)phenyl]-3-{[2-(4-amino-furazan-3-yl)-1-ethyl-1H-imidazo[4,5-c]pyridin-6-yl] oxy}benzamide;

N-(3-{[2-(4-Amino-furazan-3-yl)-1-ethyl-1H-imidazo[4,5-c]pyridin-6-yl]oxy}phenyl)-4-{[2-(4-morpholinyl)ethyl] oxy}benzamide;

3-{[2-(4-Amino-furazan-3-yl)-1-ethyl-1H-imidazo[4,5-c] pyridin-6-yl]oxy}-N-(4-piperidinylmethyl)benzamide;

N-(3-{[2-(4-Amino-furazan-3-yl)-1-ethyl-1H-imidazo[4,5-c]pyridin-6-yl]oxy}phenyl)-4-(methylamino)butanamide;

3-{[2-(4-Amino-furazan-3-yl)-1-phenyl-1H-imidazo[4,5-c] pyridin-6-yl]oxy}-N-[2-(4-hydroxyphenyl)ethyl]benzamide;

3-{[2-(4-Amino-furazan-3-yl)-1-ethyl-1H-imidazo[4,5-c] pyridin-6-yl]oxy}-N-{4-[(1,1-dioxido-4-thiomorpholinyl)methyl]phenyl}benzamide;

3-{[2-(4-Amino-furazan-3-yl)-1-ethyl-1H-imidazo[4,5-c] pyridin-6-yl]oxy}-N-[3-(1-piperidinyl)propyl]benzamide;

N-(3-{[2-(4-Amino-furazan-3-yl)-1-(1,2,3,4-tetrahydro-7-isoquinolinyl)-1H-imidazo[4,5-c]pyridin-6-yl] oxy}phenyl)acetamide;

4-{1-Ethyl-6-[(3-{[4-(1-methyl-4-piperidinyl)butyl] oxy}phenyl)oxy]-1H-imidazo[4,5-c]pyridin-2-yl}-furazan-3-amine;

N-(3-{[2-(4-Amino-furazan-3-yl)-1-ethyl-1H-imidazo[4,5-c]pyridin-6-yl]oxy}phenyl)-4-(1H-imidazol-1-yl)benzamide;

N-(3-{[2-(4-Amino-furazan-3-yl)-1-ethyl-1H-imidazo[4,5-c]pyridin-6-yl]oxy}phenyl)-4-(4-morpholinyl)butanamide;

3-{[2-(4-Amino-furazan-3-yl)-1-(4-hydroxyphenyl)-1H-imidazo[4,5-c]pyridin-6-yl]oxy}-N-[2-(4-morpholinyl) ethyl]benzamide;

3-{[2-(4-Amino-furazan-3-yl)-1-ethyl-1H-imidazo[4,5-c] pyridin-6-yl]oxy}-N-[4-(methyloxy)phenyl]benzamide;

1-(3-{[2-(4-Amino-furazan-3-yl)-1-ethyl-1H-imidazo[4,5-c]pyridin-6-yl]oxy}phenyl)-4-(4-morpholinyl)-1-butanone;

N-(3-{[2-(4-Amino-furazan-3-yl)-1-ethyl-1H-imidazo[4,5-c]pyridin-6-yl]oxy}phenyl)-3,4-bis(methyloxy)benzamide;

N-(3-{[2-(4-Amino-furazan-3-yl)-1-(4-{[2-(dimethylamino)ethyl]oxy}phenyl)-1H-imidazo[4,5-c]pyridin-6-yl]oxy}phenyl)-6-methyl-3-pyridinecarboxamide;

3-{[2-(4-Amino-furazan-3-yl)-1-ethyl-1H-imidazo[4,5-c]pyridin-6-yl]oxy}-N-[2-(4 thiomorpholinyl)ethyl]benzamide;

N-[4-(Aminomethyl)phenyl]-3-{[2-(4-amino-furazan-3-yl)-1-phenyl-1H-imidazo[4,5-c]pyridin-6-yl]oxy}benzamide;

N-(3-{[2-(4-Amino-furazan-3-yl)-1-ethyl-1H-imidazo[4,5-c]pyridin-6-yl]oxy}phenyl)-2,3-dihydro-1-benzofuran-5-carboxamide;

N-[2-(4-Acetyl-1-piperazinyl)ethyl]-3-{[2-(4-amino-furazan-3-yl)-1-ethyl-1H-imidazo[4,5-c]pyridin-6-yl]oxy}benzamide;

3-{[2-(4-Amino-furazan-3-yl)-1-(4-fluorophenyl)-1H-imidazo[4,5-c]pyridin-6-yl]oxy}-N-[3-(4-methyl-1-piperazinyl)propyl]benzamide;

N-[3-{[2-(4-Amino-furazan-3-yl)-1-ethyl-1H-imidazo[4,5-c]pyridin-6-yl]oxy}-5-(trifluoromethyl)phenyl]acetamide;

N-(3-{[2-(4-Amino-furazan-3-yl)-1-ethyl-1H-imidazo[4,5-c]pyridin-6-yl]oxy}phenyl)urea;

3-{[2-(4-Amino-furazan-3-yl)-1-ethyl-1H-imidazo[4,5-c]pyridin-6-yl]oxy}-N-[2-(4-morpholinyl)ethyl]benzamide;

N-(3-{[2-(4-Amino-furazan-3-yl)-1-ethyl-1H-imidazo[4,5-c]pyridin-6-yl]oxy}phenyl)-4-hydroxybenzamide;

3-{[2-(4-Amino-furazan-3-yl)-1-(4-fluorophenyl)-1H-imidazo[4,5-c]pyridin-6-yl]oxy}-N-[3-(4-methyl-1-piperazinyl)-3-oxopropyl]benzamide;

N-(3-{[2-(4-Amino-furazan-3-yl)-1-ethyl-1H-imidazo[4,5-c]pyridin-6-yl]oxy}phenyl)-4-(4-morpholinyl)benzamide;

N-(3-{[2-(4-Amino-furazan-3-yl)-1-(4-{[2-(dimethylamino)ethyl]oxy}phenyl)-1H-imidazo[4,5-c]pyridin-6-yl]oxy}phenyl)-4-(methyloxy)benzamide;

N-(3-{[1-{4-[(2-Aminoethyl)oxy]phenyl}-2-(4-amino-furazan-3-yl)-1H-imidazo[4,5-c]pyridin-6-yl]oxy}phenyl)acetamide;

N-(3-{[2-(4-Amino-furazan-3-yl)-1-ethyl-1H-imidazo[4,5-c]pyridin-6-yl]oxy}phenyl)-6-methyl-3-pyridinecarboxamide;

N-(3-{[2-(4-Amino-furazan-3-yl)-1-ethyl-1H-imidazo[4,5-c]pyridin-6-yl]oxy}phenyl)-2-methyl-1,3-thiazole-5-carboxamide;

N-(3-{[2-(4-Amino-furazan-3-yl)-1-ethyl-1H-imidazo[4,5-c]pyridin-6-yl]oxy}phenyl)-4-(dimethylamino)butanamide;

N-(3-{[2-(4-Amino-furazan-3-yl)-1-ethyl-1H-imidazo[4,5-c]pyridin-6-yl]oxy}phenyl)-4-{[3-(1-piperazinyl)propyl]oxy}benzamide;

N-(3-{[2-(4-Amino-furazan-3-yl)-1-ethyl-1H-imidazo[4,5-c]pyridin-6-yl]oxy}phenyl)-2-(dimethylamino)-5-pyrimidinecarboxamide;

3-({2-(4-Amino-furazan-3-yl)-1-[2-(methyloxy)phenyl]-1H-imidazo[4,5-c]pyridin-6-yl}oxy)-N-[3-(4-methyl-1-piperazinyl)propyl]benzamide;

4-{1-Ethyl-6-[(3-{[2-(1-methyl-4-piperidinyl)ethyl]oxy}phenyl)oxy]-1H-imidazo[4,5-c]pyridin-2-yl}-furazan-3-amine;

3-{[2-(4-Amino-furazan-3-yl)-1-ethyl-1H-imidazo[4,5-c]pyridin-6-yl]oxy}-N-[3-(2-oxo-1-pyrrolidinyl)propyl]benzamide;

N-(3-{[2-(4-Amino-furazan-3-yl)-1-ethyl-1H-imidazo[4,5-c]pyridin-6-yl]oxy}phenyl)-2-furancarboxamide;

3-{[2-(4-Amino-furazan-3-yl)-1-phenyl-1H-imidazo[4,5-c]pyridin-6-yl]oxy}-N-[2-(3-pyridinyl)ethyl]benzamide;

N-(3-{[2-(4-Amino-furazan-3-yl)-1-ethyl-1H-imidazo[4,5-c]pyridin-6-yl]oxy}phenyl)-4-[(1-methyl-4-piperidinyl)oxy]benzamide;

N-(3-{[2-(4-Amino-furazan-3-yl)-1-(4-{[2-(methylamino)ethyl]oxy}phenyl)-1H-imidazo[4,5-c]pyridin-6-yl]oxy}phenyl)acetamide;

N-[3-({2-(4-Amino-furazan-3-yl)-1-[4-({[(2S)-1-methyl-2-pyrrolidinyl]methyl}oxy)phenyl]-1H-imidazo[4,5-c]pyridin-6-yl}oxy)phenyl]acetamide;

N-(3-{[2-(4-Amino-furazan-3-yl)-1-ethyl-1H-imidazo[4,5-c]pyridin-6-yl]oxy}phenyl)-4-(dimethylamino)benzamide;

N-(3-{[2-(4-Amino-furazan-3-yl)-1-ethyl-1H-imidazo[4,5-c]pyridin-6-yl]oxy}phenyl)-4-(2-oxo-1-pyrrolidinyl)butanamide;

N-1-(3-{[2-(4-Amino-furazan-3-yl)-1-ethyl-1H-imidazo[4,5-c]pyridin-6-yl]oxy}phenyl)-N~3~,N~3~-dimethyl-beta-alaninamide;

N-(3-{[2-(4-Amino-furazan-3-yl)-1-ethyl-1H-imidazo[4,5-c]pyridin-6-yl]oxy}phenyl)-2-(methyloxy)acetamide;

3-{[2-(4-Amino-furazan-3-yl)-1-phenyl-1H-imidazo[4,5-c]pyridin-6-yl]oxy}-N-[3-(1H-imidazol-1-yl)propyl]benzamide;

3-{[2-(4-Amino-furazan-3-yl)-1-phenyl-1H-imidazo[4,5-c]pyridin-6-yl]oxy}-N-[2-(4-pyridinyl)ethyl]benzamide;

N-(3-{[2-(4-Amino-furazan-3-yl)-1-ethyl-1H-imidazo[4,5-c]pyridin-6-yl]oxy}phenyl)-6-(1H-pyrazol-1-yl)-3-pyridinecarboxamide;

N-(3-{[2-(4-Amino-furazan-3-yl)-1-(4-{[2-(1-pyrrolidinyl)ethyl]oxy}phenyl)-1H-imidazo[4,5-c]pyridin-6-yl]oxy}phenyl)acetamide;

3-{[2-(4-Amino-furazan-3-yl)-1-ethyl-1H-imidazo[4,5-c]pyridin-6-yl]oxy}-N-[2-(1-oxido-4-thiomorpholinyl)ethyl]benzamide;

N-(3-{[2-(4-Amino-furazan-3-yl)-1-ethyl-1H-imidazo[4,5-c]pyridin-6-yl]oxy}phenyl)-4-{[2-(1-piperazinyl)ethyl]oxy}benzamide;

N-(3-{[2-(4-Amino-furazan-3-yl)-1-ethyl-1H-imidazo[4,5-c]pyridin-6-yl]oxy}phenyl)-4-(1-piperidinyl)benzamide;

N-(3-{[2-(4-Amino-furazan-3-yl)-1-ethyl-1H-imidazo[4,5-c]pyridin-6-yl]oxy}phenyl)-4-(methyloxy)benzamide;

N-(3-{[2-(4-Amino-furazan-3-yl)-1-ethyl-1H-imidazo[4,5-c]pyridin-6-yl]oxy}phenyl)benzamide;

N-(3-{[2-(4-Amino-furazan-3-yl)-1-(4-{[2-(diethylamino)ethyl]oxy}phenyl)-1H-imidazo[4,5-c]pyridin-6-yl]oxy}phenyl)acetamide;

4-{1-Ethyl-6-[(3-{[3-(1-methyl-4-piperidinyl)propyl]oxy}phenyl)oxy]-1H-imidazo[4,5-c]pyridin-2-yl}-furazan-3-amine;

3-{[2-(4-Amino-furazan-3-yl)-1-ethyl-1H-imidazo[4,5-c]pyridin-6-yl]oxy}phenol;

N-(3-{[2-(4-Amino-furazan-3-yl)-1-ethyl-1H-imidazo[4,5-c]pyridin-6-yl]oxy}phenyl)-4-(ethyloxy)benzamide;

3-{[2-(4-Amino-furazan-3-yl)-1-phenyl-1H-imidazo[4,5-c]pyridin-6-yl]oxy}-N-(1,4-dioxan-2-ylmethyl)benzamide;

N-(3-{[2-(4-Amino-furazan-3-yl)-1-ethyl-1H-imidazo[4,5-c]pyridin-6-yl]oxy}phenyl)-2-methyl-3-pyridinecarboxamide;

N-(3-{[2-(4-Amino-furazan-3-yl)-1-ethyl-1H-imidazo[4,5-c]pyridin-6-yl]oxy}phenyl)butanamide;

N-(3-{[2-(4-Amino-furazan-3-yl)-1-ethyl-1H-imidazo[4,5-c]pyridin-6-yl]oxy}phenyl)-4-methyl-3,4-dihydro-2H-1,4-benzoxazine-7-carboxamide;

4-{2-(4-Amino-furazan-3-yl)-6-[(4-fluorophenyl)oxy]-1H-imidazo[4,5-c]pyridin-1-yl}phenol;

3-{[2-(4-Amino-furazan-3-yl)-1-(1H-benzimidazol-5-yl)-1H-imidazo[4,5-c]pyridin-6-yl]oxy}-N-[3-(2-oxo-1-pyrrolidinyl)propyl]benzamide;

3-{[2-(4-Amino-furazan-3-yl)-1-phenyl-1H-imidazo[4,5-c]pyridin-6-yl]oxy}-N-(tetrahydro-2-furanylmethyl)benzamide;

3-{[2-(4-Amino-furazan-3-yl)-1-phenyl-1H-imidazo[4,5-c]pyridin-6-yl]oxy}-N-[3-(dimethylamino)propyl]benzamide;

3-{[2-(4-Amino-furazan-3-yl)-1-(4-bromophenyl)-1H-imidazo[4,5-c]pyridin-6-yl]oxy}-N-[3-(4-methyl-1-piperazinyl)-3-oxopropyl]benzamide;

N-(3-{[2-(4-Amino-furazan-3-yl)-1-ethyl-1H-imidazo[4,5-c]pyridin-6-yl]oxy}phenyl)-4-(dimethylamino)butanamide;

N-(3-{[2-(4-Amino-furazan-3-yl)-1-ethyl-1H-imidazo[4,5-c]pyridin-6-yl]oxy}phenyl)-4-fluorobenzamide;

4-(Aminomethyl)-N-(3-{[2-(4-amino-furazan-3-yl)-1-phenyl-1H-imidazo[4,5-c]pyridin-6-yl]oxy}phenyl)benzamide;

N-(3-{[2-(4-Amino-furazan-3-yl)-1-ethyl-1H-imidazo[4,5-c]pyridin-6-yl]oxy}phenyl)-6-{[2-(4-morpholinyl)ethyl]oxy}-3-pyridinecarboxamide;

N-(3-{[2-(4-Amino-furazan-3-yl)-1-(4-{[2-(1-piperidinyl)ethyl]oxy}phenyl)-1H-imidazo[4,5-c]pyridin-6-yl]oxy}phenyl)acetamide;

3-{[2-(4-Amino-furazan-3-yl)-1-phenyl-1H-imidazo[4,5-c]pyridin-6-yl]oxy}-N-[2-(4-morpholinyl)ethyl]benzamide;

N-(3-{[2-(4-Amino-furazan-3-yl)-1-ethyl-1H-imidazo[4,5-c]pyridin-6-yl]oxy}phenyl)-3-chloro-4-(methyloxy)benzamide;

3-{[2-(4-Amino-furazan-3-yl)-1-(4-piperidinyl)-1H-imidazo[4,5-c]pyridin-6-yl]oxy}-N-[3-(4-methyl-1-piperazinyl)-3-oxopropyl]benzamide;

3-{[2-(4-Amino-furazan-3-yl)-1-phenyl-1H-imidazo[4,5-c]pyridin-6-yl]oxy}-N-[3-(1-pyrrolidinyl)propyl]benzamide;

N-(3-{[2-(4-Amino-furazan-3-yl)-1-(cyclopropylmethyl)-1H-imidazo[4,5-c]pyridin-6-yl]oxy}phenyl)-4-{[2-(4-morpholinyl)ethyl]oxy}benzamide;

N-(3-{[2-(4-Amino-furazan-3-yl)-1-ethyl-1H-imidazo[4,5-c]pyridin-6-yl]oxy}phenyl)-3-fluoro-4-(methyloxy)benzamide;

3-{[2-(4-Amino-furazan-3-yl)-1-(cyclopropylmethyl)-1H-imidazo[4,5-c]pyridin-6-yl]oxy}-N-[2-(4-morpholinyl)ethyl]benzamide;

N-(3-{[2-(4-Amino-furazan-3-yl)-1-ethyl-1H-imidazo[4,5-c]pyridin-6-yl]oxy}phenyl)-3-(methyloxy)benzamide;

3-({2-(4-Amino-furazan-3-yl)-1-[2-(methyloxy)phenyl]-1H-imidazo[4,5-c]pyridin-6-yl}oxy)-N-[2-(4-morpholinyl)ethyl]benzamide;

N-(3-{[2-(4-Amino-furazan-3-yl)-1-ethyl-1H-imidazo[4,5-c]pyridin-6-yl]oxy}phenyl)-3-(3-hydroxyphenyl)propanamide;

N-(3-{[2-(4-Amino-furazan-3-yl)-1-(4-{[2-(dimethylamino)ethyl]oxy}phenyl)-1H-imidazo[4,5-c]pyridin-6-yl]oxy}phenyl)acetamide;

4-[6-[(4-Fluorophenyl)oxy]-1-(1,2,3,4-tetrahydro-7-isoquinolinyl)-1H-imidazo[4,5-c]pyridin-2-yl]-furazan-3-amine;

3-{[2-(4-Amino-furazan-3-yl)-1-(1,2,3,4-tetrahydro-7-isoquinolinyl)-1H-imidazo[4,5-c]pyridin-6-yl]oxy}-N-[3-(2-oxo-1-pyrrolidinyl)propyl]benzamide;

3-{[2-(4-Amino-furazan-3-yl)-1-(4-fluorophenyl)-1H-imidazo[4,5-c]pyridin-6-yl]oxy}-N-[2-(4-morpholinyl)ethyl]benzamide;

N-(3-{[2-(4-Amino-furazan-3-yl)-1-ethyl-1H-imidazo[4,5-c]pyridin-6-yl]oxy}phenyl)-6-[(2,2,2-trifluoroethyl)oxy]-3-pyridinecarboxamide;

N-(3-{[2-(4-Amino-furazan-3-yl)-1-ethyl-1H-imidazo[4,5-c]pyridin-6-yl]oxy}phenyl)-N'-methylurea;

3-{[2-(4-Amino-furazan-3-yl)-1-phenyl-1H-imidazo[4,5-c]pyridin-6-yl]oxy}-N-[3-(4-morpholinyl)propyl]benzamide;

N-(3-{[2-(4-Amino-furazan-3-yl)-1-phenyl-1H-imidazo[4,5-c]pyridin-6-yl]oxy}phenyl)-4-{[2-(4-morpholinyl)ethyl]oxy}benzamide;

3-{[2-(4-Amino-furazan-3-yl)-1-phenyl-1H-imidazo[4,5-c]pyridin-6-yl]oxy}-N-[4-(methyloxy)phenyl]benzamide;

4-(6-{[3-Amino-5-(trifluoromethyl)phenyl]oxy}-1-ethyl-1H-imidazo[4,5-c]pyridin-2-yl)-furazan-3-amine;

N-(3-{[2-(4-Amino-furazan-3-yl)-1-ethyl-1H-imidazo[4,5-c]pyridin-6-yl]oxy}phenyl)-1-methyl-4-piperidinecarboxamide;

3-{[2-(4-Amino-furazan-3-yl)-1-phenyl-1H-imidazo[4,5-c]pyridin-6-yl]oxy}-N-[2-(1-pyrrolidinyl)ethyl]benzamide;

3-({2-(4-Amino-furazan-3-yl)-1-[2-(methyloxy)phenyl]-1H-imidazo[4,5-c]pyridin-6-yl}oxy)-N-[3-(2-oxo-1-pyrrolidinyl)propyl]benzamide;

3-{[2-(4-Amino-furazan-3-yl)-1-phenyl-1H-imidazo[4,5-c]pyridin-6-yl]oxy}-N-(3-amino-3-oxopropyl)benzamide;

N-(3-{[2-(4-Amino-furazan-3-yl)-1-(4-hydroxyphenyl)-1H-imidazo[4,5-c]pyridin-6-yl]oxy}phenyl)methanesulfonamide;

3-{[2-(4-Amino-furazan-3-yl)-1-phenyl-1H-imidazo[4,5-c]pyridin-6-yl]oxy}-N-(4-pyridinylmethyl)benzamide;

N'-(3-{[2-(4-Amino-furazan-3-yl)-1-(4-hydroxyphenyl)-1H-imidazo[4,5-c]pyridin-6-yl]oxy}phenyl)-N,N-dimethylsulfamide;

Methyl 3-{[2-(4-amino-furazan-3-yl)-1-(H-benzimidazol-5-yl)-1H-imidazo[4,5-c]pyridin-6-yl]oxy}benzoate;

N-{3-[(2-(4-Amino-furazan-3-yl)-1-{4-[(cyanomethyl)oxy]phenyl}-1H-imidazo[4,5-c]pyridin-6-yl)oxy]phenyl}acetamide;

3-{[2-(4-Amino-furazan-3-yl)-1-phenyl-1H-imidazo[4,5-c]pyridin-6-yl]oxy}-N-[2-(2-pyridinyl)ethyl]benzamide;

N-(3-{[2-(4-Amino-furazan-3-yl)-1-(4-{[2-(dimethylamino)ethyl]oxy}phenyl)-1H-imidazo[4,5-c]pyridin-6-yl]oxy}phenyl)-N'-methylurea;

3-{[2-(4-Amino-furazan-3-yl)-1-ethyl-1H-imidazo[4,5-c]pyridin-6-yl]oxy}-N-[2-(1,1-dioxido-4-thiomorpholinyl)ethyl]benzamide;

N-(3-{[2-(4-Amino-furazan-3-yl)-1-phenyl-1H-imidazo[4,5-c]pyridin-6-yl]oxy}phenyl)acetamide;

3-{[2-(4-Amino-furazan-3-yl)-1-phenyl-1H-imidazo[4,5-c]pyridin-6-yl]oxy}-N-[3-(2-oxo-1-pyrrolidinyl)propyl]benzamide;

4-{1-Ethyl-6-[(3-{[(1-methyl-4-piperidinyl)methyl]oxy}phenyl)oxy]-1H-imidazo[4,5-c]pyridin-2-yl}-furazan-3-amine;

N-(3-{[2-(4-Amino-furazan-3-yl)-1-ethyl-1H-imidazo[4,5-c]pyridin-6-yl]oxy}phenyl)pyrazolo[1,5-a]pyridine-3-carboxamide;

N-(3-{[2-(4-Amino-furazan-3-yl)-1-(4-hydroxyphenyl)-1H-imidazo[4,5-c]pyridin-6-yl]oxy}phenyl)acetamide;

3-{[2-(4-Amino-furazan-3-yl)-1-phenyl-1H-imidazo[4,5-c]pyridin-6-yl]oxy}-N-[2-(dimethylamino)ethyl]benzamide;

N-(3-{[2-(4-Amino-furazan-3-yl)-1-ethyl-1H-imidazo[4,5-c]pyridin-6-yl]oxy}phenyl)-4-(3,5-dimethyl-1H-pyrazol-1-yl)benzamide;

3-({2-(4-Amino-furazan-3-yl)-1-[4-(trifluoromethyl)phenyl]-1H-imidazo[4,5-c]pyridin-6-yl}oxy)-N-[3-(4-methyl-1-piperazinyl)propyl]benzamide;

N-(3-{[2-(4-Amino-furazan-3-yl)-1-(4-{[2-(dimethylamino)ethyl]oxy}phenyl)-1H-imidazo[4,5-c]pyridin-6-yl]oxy}phenyl)methanesulfonamide;

3-{[2-(4-Amino-furazan-3-yl)-1-(4-fluorophenyl)-1H-imidazo[4,5-c]pyridin-6-yl]oxy}-N-[3-(2-oxo-1-pyrrolidinyl)propyl]benzamide;

4-[1-(4-{[2-(Dimethylamino)ethyl]oxy}phenyl)-6-(methyloxy)-1H-imidazo[4,5-c]pyridin-2-yl]-furazan-3-amine;

N-(3-{[2-(4-Amino-furazan-3-yl)-1-ethyl-1H-imidazo[4,5-c]pyridin-6-yl]oxy}phenyl)-1-methyl-4-piperidinecarboxamide;

1-(3-{[2-(4-Amino-furazan-3-yl)-1-ethyl-1H-imidazo[4,5-c]pyridin-6-yl]oxy}phenyl)ethanone;

N-(3-{[2-(4-Amino-furazan-3-yl)-1-ethyl-1H-imidazo[4,5-c]pyridin-6-yl]oxy}phenyl)-4-cyanobenzamide;

3-{[2-(4-Amino-furazan-3-yl)-1-(1H-indazol-5-yl)-1H-imidazo[4,5-c]pyridin-6-yl]oxy}-N-[3-(2-oxo-1-pyrrolidinyl)propyl]benzamide;

N-(3-{[2-(4-Amino-furazan-3-yl)-1-ethyl-1H-imidazo[4,5-c]pyridin-6-yl]oxy}phenyl)-N'-(phenylmethyl)urea;

3-{[2-(4-Amino-furazan-3-yl)-1-phenyl-1H-imidazo[4,5-c]pyridin-6-yl]oxy}-N-[2-(1-methyl-1H-pyrrol-2-yl)ethyl]benzamide;

N-(3-{[2-(4-Amino-furazan-3-yl)-1-phenyl-1H-imidazo[4,5-c]pyridin-6-yl]oxy}phenyl)-4-(2-oxo-1-pyrrolidinyl)butanamide;

N-(3-{[2-(4-Amino-furazan-3-yl)-1-(4-{[2-(4-morpholinyl)ethyl]oxy}phenyl)-1H-imidazo[4,5-c]pyridin-6-yl]oxy}phenyl)acetamide;

3-{[2-(4-Amino-furazan-3-yl)-1-phenyl-1H-imidazo[4,5-c]pyridin-6-yl]oxy}-N-[4-(dimethylamino)phenyl]benzamide;

3-{[2-(4-Amino-furazan-3-yl)-1-(4-piperidinyl)-1H-imidazo[4,5-c]pyridin-6-yl]oxy}-N-[3-(2-oxo-1-pyrrolidinyl)propyl]benzamide;

4-[6-(1H-Benzimidazol-4-yloxy)-1-phenyl-1H-imidazo[4,5-c]pyridin-2-yl]-furazan-3-amine;

N-(3-{[2-(4-Amino-furazan-3-yl)-1-ethyl-1H-imidazo[4,5-c]pyridin-6-yl]oxy}phenyl)-2-methylpropanamide;

3-({2-(4-Amino-furazan-3-yl)-1-[3-(methyloxy)propyl]-1H-imidazo[4,5-c]pyridin-6-yl}oxy)-N-[2-(4-morpholinyl)ethyl]benzamide;

N-(3-{[2-(4-Amino-furazan-3-yl)-1-ethyl-1H-imidazo[4,5-c]pyridin-6-yl]oxy}phenyl)methanesulfonamide;

3-({2-(4-Amino-furazan-3-yl)-1-[2-(methyloxy)ethyl]-1H-imidazo[4,5-c]pyridin-6-yl}oxy)-N-[2-(4-morpholinyl)ethyl]benzamide;

N-(3-{[2-(4-Amino-furazan-3-yl)-1-ethyl-1H-imidazo[4,5-c]pyridin-6-yl]oxy}phenyl)-2-(methyloxy)-3-pyridinecarboxamide;

N-(3-{[2-(4-Amino-furazan-3-yl)-1-ethyl-1H-imidazo[4,5-c]pyridin-6-yl]oxy}phenyl)-4-morpholinecarboxamide;

N'-(3-{[2-(4-Amino-furazan-3-yl)-1-ethyl-1H-imidazo[4,5-c]pyridin-6-yl]oxy}phenyl)-N,N-dimethylsulfamide;

N-[2-(Acetylamino)ethyl]-3-{[2-(4-amino-furazan-3-yl)-1-phenyl-1H-imidazo[4,5-c]pyridin-6-yl]oxy}benzamide;

3-{[2-(4-Amino-furazan-3-yl)-1-phenyl-1H-imidazo[4,5-c]pyridin-6-yl]oxy}-N-[2-(methyloxy)ethyl]benzamide;

3-{[2-(4-Amino-furazan-3-yl)-1-phenyl-1H-imidazo[4,5-c]pyridin-6-yl]oxy}-N-(2-cyanoethyl)benzamide;

3-({2-(4-Amino-furazan-3-yl)-1-[2-(methyloxy)ethyl]-1H-imidazo[4,5-c]pyridin-6-yl}oxy)-N-[3-(4-methyl-1-piperazinyl)-3-oxopropyl]benzamide;

4-(1-Ethyl-6-{[3-(methylsulfonyl)phenyl]oxy}-1H-imidazo[4,5-c]pyridin-2-yl)-furazan-3-amine;

N-(3-{[2-(4-Amino-furazan-3-yl)-1-ethyl-1H-imidazo[4,5-c]pyridin-6-yl]oxy}phenyl)-4-chloro-2-pyridinecarboxamide;

N-(3-{[2-(4-Amino-furazan-3-yl)-1-ethyl-1H-imidazo[4,5-c]pyridin-6-yl]oxy}phenyl)-4-(trifluoromethyl)-3-pyridinecarboxamide;

N'-(3-{[2-(4-Amino-furazan-3-yl)-1-(4-{[2-(dimethylamino)ethyl]oxy}phenyl)-1H-imidazo[4,5-c]pyridin-6-yl]oxy}phenyl)-N,N-dimethylsulfamide;

4-{6-[(3-Aminophenyl)oxy]-1-ethyl-1H-imidazo[4,5-c]pyridin-2-yl}-furazan-3-amine;

Methyl 3-{[2-(4-amino-furazan-3-yl)-1-ethyl-1H-imidazo[4,5-c]pyridin-6-yl]oxy}benzoate;

3-{[2-(4-Amino-furazan-3-yl)-1-phenyl-1H-imidazo[4,5-c]pyridin-6-yl]oxy}-N-[(1,5-dimethyl-1H-pyrazol-4-yl)methyl]benzamide;

N-(3-{[2-(4-Amino-furazan-3-yl)-1-(4-{[2-(dimethylamino)ethyl]oxy}phenyl)-1H-imidazo[4,5-c]pyridin-6-yl]oxy}phenyl)-2-methylpropanamide;

4-{1-Ethyl-6-[(phenylmethyl)oxy]-1H-imidazo[4,5-c]pyridin-2-yl}-furazan-3-amine;

N-(3-{[2-(4-Amino-furazan-3-yl)-1-phenyl-1H-imidazo[4,5-c]pyridin-6-yl]oxy}phenyl)-3-(4-morpholinyl)propanamide;

4-[1-Ethyl-6-({3-[(1E)-3-(4-methyl-1-piperazinyl)-3-oxo-1-propen-1-yl]phenyl}oxy)-1H-imidazo[4,5-c]pyridin-2-yl]-furazan-3-amine;

N-(3-{[2-(4-Amino-furazan-3-yl)-1-ethyl-1H-imidazo[4,5-c]pyridin-6-yl]oxy}phenyl)-N'-phenylurea;

3-{[2-(4-Amino-furazan-3-yl)-1-(1,3-benzodioxol-5-yl)-1H-imidazo[4,5-c]pyridin-6-yl]oxy}-N-[3-(2-oxo-1-pyrrolidinyl)propyl]benzamide;

4-{1-[4-(Aminomethyl)phenyl]-6-[(4-fluorophenyl)oxy]-1H-imidazo[4,5-c]pyridin-2-yl}-furazan-3-amine;

3-{[2-(4-Amino-furazan-3-yl)-1-ethyl-1H-imidazo[4,5-c]pyridin-6-yl]oxy}benzoic acid;

N-(5-{[2-(4-Amino-furazan-3-yl)-1-ethyl-1H-imidazo[4,5-c]pyridin-6-yl]oxy}-2-chlorophenyl)acetamide;

4-{1-(2,3-Dihydro-1H-isoindol-5-yl)-6-[(4-fluorophenyl)oxy]-1H-imidazo[4,5-c]pyridin-2-yl}-furazan-3-amine;

3-{[2-(4-Amino-furazan-3-yl)-1-phenyl-1H-imidazo[4,5-c]pyridin-6-yl]oxy}-N-methylbenzamide;

3-{[2-(4-Amino-furazan-3-yl)-1-phenyl-1H-imidazo[4,5-c]pyridin-6-yl]oxy}benzamide;

3-{[2-(4-Amino-furazan-3-yl)-1-(4-bromophenyl)-1H-imidazo[4,5-c]pyridin-6-yl]oxy}-N-[3-(2-oxo-1-pyrrolidinyl)propyl]benzamide;

4-{6-[(3-{[3-(4-Acetyl-1-piperazinyl)propyl]oxy}phenyl)oxy]-1-ethyl-1H-imidazo[4,5-c]pyridin-2-yl}-furazan-3-amine;

N-(3-{[2-(4-Amino-furazan-3-yl)-1-ethyl-1H-imidazo[4,5-c]pyridin-6-yl]oxy}phenyl)-1-methyl-1H-imidazole-2-carboxamide;

3-({2-(4-Amino-furazan-3-yl)-1-[2-(methyloxy)ethyl]-1H-imidazo[4,5-c]pyridin-6-yl}oxy)-N-[3-(2-oxo-1-pyrrolidinyl)propyl]benzamide trifluoroacetate;

3-{[2-(4-Amino-furazan-3-yl)-1-phenyl-1H-imidazo[4,5-c]pyridin-6-yl]oxy}-N-methylbenzamide;

N-(4-{[2-(4-Amino-furazan-3-yl)-1-(4-{[2-(dimethylamino)ethyl]oxy}phenyl)-1H-imidazo[4,5-c]pyridin-6-yl]oxy}phenyl)acetamide;

N-[3-({2-(4-Amino-furazan-3-yl)-1-[2-(methyloxy)ethyl]-1H-imidazo[4,5-c]pyridin-6-yl}oxy)phenyl]acetamide;

N-(4-{[2-(4-Amino-furazan-3-yl)-1-(4-hydroxyphenyl)-1H-imidazo[4,5-c]pyridin-6-yl]oxy}phenyl)acetamide;

4-(1-(1,2,3,4-Tetrahydro-7-isoquinolinyl)-6-{[4-(trifluoromethyl)phenyl]oxy}-1H-imidazo[4,5-c]pyridin-2-yl)-furazan-3-amine;

4-[6-[(4-Fluorophenyl)oxy]-1-(4-{[2-(methylamino)ethyl]oxy}phenyl)-1H-imidazo[4,5-c]pyridin-2-yl]-furazan-3-amine;

N-[3-({2-(4-Amino-furazan-3-yl)-1-[3-(methyloxy)propyl]-1H-imidazo[4,5-c]pyridin-6-yl}oxy)phenyl]acetamide;

3-{[2-(4-Amino-furazan-3-yl)-1-phenyl-1H-imidazo[4,5-c]pyridin-6-yl]oxy}-N-[(4-methyl-1,3-thiazol-2-yl)methyl]benzamide;

1-(3-{[2-(4-Amino-furazan-3-yl)-1-ethyl-1H-imidazo[4,5-c]pyridin-6-yl]oxy}phenyl)-4-(4-morpholinyl)-1-butanol;

methyl 3-{[2-(4-Amino-furazan-3-yl)-1-(1H-indazol-5-yl)-1H-imidazo[4,5-c]pyridin-6-yl]oxy}benzoate;

N-(3-{[2-(4-Amino-furazan-3-yl)-1-phenyl-1H-imidazo[4,5-c]pyridin-6-yl]oxy}phenyl)-3-(2-oxo-1-pyrrolidinyl)propanamide;

4-{1-Ethyl-6-[(3-{[(1-methyl-3-piperidinyl)methyl]oxy}phenyl)oxy]-1H-imidazo[4,5-c]pyridin-2-yl}-furazan-3-amine;

3-({2-(4-Amino-furazan-3-yl)-1-[3-(methyloxy)propyl]-1H-imidazo[4,5-c]pyridin-6-yl}oxy)-N-[3-(2-oxo-1-pyrrolidinyl)propyl]benzamide;

N-(3-{[2-(4-Amino-furazan-3-yl)-1-ethyl-1H-imidazo[4,5-c]pyridin-6-yl]oxy}phenyl)-4-(methyloxy)benzenesulfonamide;

N-(3-{[2-(4-Amino-furazan-3-yl)-1-ethyl-1H-imidazo[4,5-c]pyridin-6-yl]oxy}phenyl)cyclohexanecarboxamide;

3-{[2-(4-Amino-furazan-3-yl)-1-phenyl-1H-imidazo[4,5-c]pyridin-6-yl]oxy}-N-{[4-(methyloxy)phenyl]methyl}benzamide;

3-{[2-(4-Amino-furazan-3-yl)-1-phenyl-1H-imidazo[4,5-c]pyridin-6-yl]oxy}-N-(cyclopropylmethyl)benzamide;

3-{[2-(4-Amino-furazan-3-yl)-1-phenyl-1H-imidazo[4,5-c]pyridin-6-yl]oxy}-N-(1,3-benzodioxol-5-ylmethyl)benzamide;

N-(3-{[2-(4-Amino-furazan-3-yl)-1-ethyl-1H-imidazo[4,5-c]pyridin-6-yl]oxy}phenyl)-1-butanesulfonamide;

N-[(3-{[2-(4-Amino-furazan-3-yl)-1-phenyl-1H-imidazo[4,5-c]pyridin-6-yl]oxy}phenyl)carbonyl]-beta-alanine;

4-{1-Ethyl-6-[(3-{[3-(4-morpholinyl)propyl]oxy}phenyl)oxy]-1H-imidazo[4,5-c]pyridin-2-yl}-furazan-3-amine;

1,1-Dimethylethyl (3-{[2-(4-amino-furazan-3-yl)-1-ethyl-1H-imidazo[4,5-c]pyridin-6-yl]oxy}phenyl)carbamate;

3-({2-(4-Amino-furazan-3-yl)-1-[4-(trifluoromethyl)phenyl]-1H-imidazo[4,5-c]pyridin-6-yl}oxy)-N-[2-(4-morpholinyl)ethyl]benzamide;

3-{[2-(4-Amino-furazan-3-yl)-1-phenyl-1H-imidazo[4,5-c]pyridin-6-yl]oxy}-N-[3-(dimethylamino)phenyl]benzamide;

1-(3-{[2-(4-Amino-furazan-3-yl)-1-ethyl-1H-imidazo[4,5-c]pyridin-6-yl]oxy}phenyl)-2-methyl-4-(4-morpholinyl)-1-butanone;

1-(3-{[2-(4-Amino-furazan-3-yl)-1-ethyl-1H-imidazo[4,5-c]pyridin-6-yl]oxy}phenyl)-1-propanone;

1-(3-{[2-(4-Amino-furazan-3-yl)-1-ethyl-1H-imidazo[4,5-c]pyridin-6-yl]oxy}phenyl)ethanol;

4-[6-[(4-Fluorophenyl)oxy]-1-(2-methyl-1,2,3,4-tetrahydro-7-isoquinolinyl)-1H-imidazo[4,5-c]pyridin-2-yl]-furazan-3-amine;

2-(3-{[2-(4-Amino-furazan-3-yl)-1-ethyl-1H-imidazo[4,5-c]pyridin-6-yl]oxy}phenyl)-2-butanol;

3-{[2-(4-Amino-furazan-3-yl)-1-(6-methyl-2-pyridinyl)-1H-imidazo[4,5-c]pyridin-6-yl]oxy}-N-[3-(2-oxo-1-pyrrolidinyl)propyl]benzamide;

4-{6-[(3-Aminophenyl)oxy]-1-phenyl-1H-imidazo[4,5-c]pyridin-2-yl}-furazan-3-amine;

3-{[2-(4-Amino-furazan-3-yl)-1-ethyl-1H-imidazo[4,5-c]pyridin-6-yl]oxy}-N-methyl-N-[3-(1-methyl-4-piperidinyl)propyl]benzamide;

3-{[2-(4-Amino-furazan-3-yl)-1-phenyl-1H-imidazo[4,5-c]pyridin-6-yl]oxy}-N-{2-[3,5-bis(methyloxy)phenyl]ethyl}benzamide;

N-(3-{[2-(4-Amino-furazan-3-yl)-1-phenyl-1H-imidazo[4,5-c]pyridin-6-yl]oxy}phenyl)-4-(dimethylamino)benzamide;

4-(1-(4-{[2-(Dimethylamino)ethyl]oxy}phenyl)-6-{[3-(methylsulfonyl)phenyl]oxy}-1H-imidazo[4,5-c]pyridin-2-yl)-furazan-3-amine;

4-(1-Ethyl-6-{[3-(methyloxy)phenyl]oxy}-1H-imidazo[4,5-c]pyridin-2-yl)-furazan-3-amine;

3-{[2-(4-Amino-furazan-3-yl)-1-(6-methyl-2-pyridinyl)-1H-imidazo[4,5-c]pyridin-6-yl]oxy}-N-[2-(4-morpholinyl)ethyl]benzamide;

4-[1-Ethyl-6-({3-[3-(4-methyl-1-piperazinyl)-3-oxopropyl]phenyl}oxy)-1H-imidazo[4,5-c]pyridin-2-yl]-furazan-3-amine, N-(3-{[2-(4-Amino-furazan-3-yl)-1-ethyl-1H-imidazo[4,5-c]pyridin-6-yl]oxy}phenyl)-4-(methyloxy)-3-(trifluoromethyl)benzamide;

N-(3-{[2-(4-Amino-furazan-3-yl)-1-phenyl-1H-imidazo[4,5-c]pyridin-6-yl]oxy}phenyl)-4-(methyloxy)benzamide;

N-(3-{[2-(4-Amino-furazan-3-yl)-1-ethyl-1H-imidazo[4,5-c]pyridin-6-yl]oxy}phenyl)-4-methylbenzenesulfonamide;

Methyl (3-{[2-(4-amino-furazan-3-yl)-1-ethyl-1H-imidazo[4,5-c]pyridin-6-yl]oxy}phenyl)acetate;

N-(5-{[2-(4-Amino-furazan-3-yl)-1-ethyl-1H-imidazo[4,5-c]pyridin-6-yl]oxy}-2-methylphenyl)acetamide;

1-{3-[(3-{[2-(4-Amino-furazan-3-yl)-1-ethyl-1H-imidazo[4,5-c]pyridin-6-yl]oxy}phenyl)oxy]propyl}-2-pyrrolidinone;

(3-{[2-(4-Amino-furazan-3-yl)-1-ethyl-1H-imidazo[4,5-c]pyridin-6-yl]oxy}phenyl)acetic acid;

N-(4-{[2-(4-Amino-furazan-3-yl)-1-ethyl-1H-imidazo[4,5-c]pyridin-6-yl]thio}phenyl)acetamide;

N-(3-{[2-(4-Amino-furazan-3-yl)-1-ethyl-1H-imidazo[4,5-c]pyridin-6-yl]oxy}phenyl)-4-fluorobenzenesulfonamide;

1-(3-{[2-(4-Amino-furazan-3-yl)-1-phenyl-1H-imidazo[4,5-c]pyridin-6-yl]oxy}phenyl)ethanone;

4-{2-(4-Amino-furazan-3-yl)-6-[(3-aminophenyl)oxy]-1H-imidazo[4,5-c]pyridin-1-yl}phenyl 2-methylpropanoate;

3-{[2-(4-Amino-furazan-3-yl)-1-ethyl-1H-imidazo[4,5-c]pyridin-6-yl]oxy}benzonitrile;

N-(3-{[2-(4-Amino-furazan-3-yl)-1-ethyl-1H-imidazo[4,5-c]pyridin-6-yl]oxy}phenyl)-3-methylbutanamide;

4-({[(3-{[2-(4-Amino-furazan-3-yl)-1-ethyl-1H-imidazo[4,5-c]pyridin-6-yl]oxy}phenyl)amino]carbonyl}amino)benzoic acid;

4-{6-[(4-Aminophenyl)oxy]-1-phenyl-1H-imidazo[4,5-c]pyridin-2-yl}-furazan-3-amine;

4-{1-Ethyl-6-[(3-{[2-(4-morpholinyl)ethyl]oxy}phenyl)oxy]-1H-imidazo[4,5-c]pyridin-2-yl}-furazan-3-amine;

3-({2-(4-Amino-furazan-3-yl)-1-[2-(4-morpholinyl)ethyl]-1H-imidazo[4,5-c]pyridin-6-yl}oxy)-N-[3-(4-methyl-1-piperazinyl)propyl]benzamide;

3-{[2-(4-Amino-furazan-3-yl)-1-(2-methyl-4-pyridinyl)-1H-imidazo[4,5-c]pyridin-6-yl]oxy}-N-[2-(4-morpholinyl)ethyl]benzamide;

3-({2-(4-Amino-furazan-3-yl)-1-[4-(trifluoromethyl)phenyl]-1H-imidazo[4,5-c]pyridin-6-yl}oxy)-N-[3-(2-oxo-1-pyrrolidinyl)propyl]benzamide;

Methyl 3-{[2-(4-amino-furazan-3-yl)-1-(4-piperidinyl)-1H-imidazo[4,5-c]pyridin-6-yl]oxy}benzoate;

N-(3-{[2-(4-Amino-furazan-3-yl)-1-ethyl-1H-imidazo[4,5-c]pyridin-6-yl]oxy}phenyl)-N-methylacetamide;

N-(4-{2-(4-Amino-furazan-3-yl)-6-[(4-fluorophenyl)oxy]-1H-imidazo[4,5-c]pyridin-1-yl}phenyl)methanesulfonamide;

Methyl 3-{[2-(4-amino-furazan-3-yl)-1-phenyl-1H-imidazo[4,5-c]pyridin-6-yl]oxy}benzoate;

3-{[2-(4-Amino-furazan-3-yl)-1-phenyl-1H-imidazo[4,5-c]pyridin-6-yl]oxy}-N-[2-(phenyloxy)ethyl]benzamide;

N-(3-{[2-(4-Amino-furazan-3-yl)-1-ethyl-1H-imidazo[4,5-c]pyridin-6-yl]oxy}-2-methylphenyl)acetamide;

3-{[2-(4-Amino-furazan-3-yl)-1-phenyl-1H-imidazo[4,5-c]pyridin-6-yl]oxy}-N-[3-(dimethylamino)propyl]-N-methylbenzamide;

3-{[2-(4-Amino-furazan-3-yl)-1-(phenylmethyl)-1H-imidazo[4,5-c]pyridin-6-yl]oxy}-N-[2-(4-morpholinyl)ethyl]benzamide;

3-{[2-(4-Amino-furazan-3-yl)-1-phenyl-1H-imidazo[4,5-e]pyridin-6-yl]oxy}-N-[2-(4-morpholinyl)ethyl]benzenesulfonamide;

4-{2-(4-Amino-furazan-3-yl)-6-[(4-fluorophenyl)oxy]-1H-imidazo[4,5-c]pyridin-1-yl}-2-chlorophenol;

4-{[2-(4-Amino-furazan-3-yl)-1-ethyl-1H-imidazo[4,5-c]pyridin-6-yl]oxy}benzonitrile;

4-(1-Ethyl-7-{[3-(methyloxy)phenyl]oxy}-1H-imidazo[4,5-c]pyridin-2-yl)-furazan-3-amine;

3-{[2-(4-Amino-furazan-3-yl)-1-phenyl-1H-imidazo[4,5-c]pyridin-6-yl]oxy}benzoic acid;

4-{6-[(3,4-Dimethylphenyl)oxy]-1-ethyl-1H-imidazo[4,5-c]pyridin-2-yl}-furazan-3-amine;

4-{1-[2-(Aminoacetyl)-1,2,3,4-tetrahydro-7-isoquinolinyl]-6-[(4-fluorophenyl)oxy]-1H-imidazo[4,5-c]pyridin-2-yl}-furazan-3-amine;

4-(1-Ethyl-6-{[3-(1,3-thiazol-5-yl)phenyl]oxy}-1H-imidazo[4,5-c]pyridin-2-yl)-furazan-3-amine;

4-(1-Ethyl-6-{[3-(1H-imidazol-1-yl)phenyl]oxy}-1H-imidazo[4,5-c]pyridin-2-yl)-furazan-3-amine;

4-(1-Ethyl-6-{[3-(1,3-oxazol-5-yl)phenyl]oxy}-1H-imidazo[4,5-c]pyridin-2-yl)-furazan-3-amine;

4-(1-Ethyl-6-{[3-(4-morpholinyl)phenyl]oxy}-1H-imidazo[4,5-c]pyridin-2-yl)-furazan-3-amine;

4-(1-Phenyl-6-{[3-(1-piperidinylcarbonyl)phenyl]oxy}-1H-imidazo[4,5-c]pyridin-2-yl)-furazan-3-amine;

4-(6-{[3-(Dimethylamino)phenyl]oxy}-1-ethyl-1H-imidazo[4,5-c]pyridin-2-yl)-furazan-3-amine;

3-{[2-(4-Amino-furazan-3-yl)-1-phenyl-1H-imidazo[4,5-c]pyridin-6-yl]oxy}-N,N-dimethylbenzamide;

N-(4-{[2-(4-Amino-furazan-3-yl)-1-phenyl-1H-imidazo[4,5-c]pyridin-6-yl]oxy}phenyl)acetamide;

Methyl 3-{[2-(4-amino-furazan-3-yl)-1-(1,3-benzodioxol-5-yl)-1H-imidazo[4,5-c]pyridin-6-yl]oxy}benzoate;

5-{[2-(4-Amino-furazan-3-yl)-1-ethyl-1H-imidazo[4,5-c]pyridin-6-yl]oxy}-1,3-dimethyl-1,3-dihydro-2H-benzimidazol-2-one;

3-{[2-(4-Amino-furazan-3-yl)-1-phenyl-1H-imidazo[4,5-c]pyridin-6-yl]oxy}-N-[3-(ethyloxy)propyl]benzamide;

2-[7-{2-(4-Amino-furazan-3-yl)-6-[(4-fluorophenyl)oxy]-1H-imidazo[4,5-c]pyridin-1-yl}-3,4-dihydro-2(1H)-isoquinolinyl]acetamide;

Methyl 3-{[2-(4-amino-furazan-3-yl)-1-(4-bromophenyl)-1H-imidazo[4,5-c]pyridin-6-yl]oxy}benzoate;

6-{[2-(4-Amino-furazan-3-yl)-1-ethyl-1H-imidazo[4,5-c]pyridin-6-yl]oxy}-3,4-dihydro-1(2H)-naphthalenone;

4-[6-(1H-Benzimidazol-5-yloxy)-1-ethyl-1H-imidazo[4,5-c]pyridin-2-yl]-furazan-3-amine;

4-(1-Ethyl-6-{[3-(1-methylethyl)phenyl]oxy}-1H-imidazo[4,5-c]pyridin-2-yl)-furazan-3-amine;

4-{1-(3-Chloro-4-{[2-(dimethylamino)ethyl]oxy}phenyl)-6-[(4-fluorophenyl)oxy]-1H-imidazo[4,5-c]pyridin-2-yl}-furazan-3-amine;

4-{6-[(4-Fluorophenyl)oxy]-1-phenyl-1H-imidazo[4,5-c]pyridin-2-yl}-furazan-3-amine;

Methyl 4-{[2-(4-amino-furazan-3-yl)-1-ethyl-1H-imidazo[4,5-c]pyridin-6-yl]oxy}benzoate;

4-{6-[(3-Nitrophenyl)oxy]-1-phenyl-1H-imidazo[4,5-c]pyridin-2-yl}-furazan-3-amine;

3-({2-(4-Amino-furazan-3-yl)-1-[2-(4-morpholinyl)ethyl]-1H-imidazo[4,5-c]pyridin-6-yl}oxy)-N-[3-(2-oxo-1-pyrrolidinyl)propyl]benzamide;

3-({2-(4-Amino-furazan-3-yl)-1-[2-(dimethylamino)ethyl]-1H-imidazo[4,5-c]pyridin-6-yl}oxy)-N-[3-(2-oxo-1-pyrrolidinyl)propyl]benzamide;

3-{[2-(4-Amino-furazan-3-yl)-1-(phenylmethyl)-1H-imidazo[4,5-c]pyridin-6-yl]oxy}benzoic acid;

Methyl 3-{[2-(4-amino-furazan-3-yl)-1-(phenylmethyl)-1H-imidazo[4,5-c]pyridin-6-yl]oxy}benzoate;

7-{[2-(4-Amino-furazan-3-yl)-1-ethyl-1H-imidazo[4,5-c]pyridin-6-yl]oxy}-4-methyl-2(1H)-quinolinone;

4-{2-(4-Amino-furazan-3-yl)-6-[(3-aminophenyl)oxy]-1H-imidazo[4,5-c]pyridin-1-yl}phenyl 4-(methyloxy)benzoate;

3-({2-(4-Amino-furazan-3-yl)-1-[2-(4-morpholinyl)ethyl]-1H-imidazo[4,5-c]pyridin-6-yl}oxy)benzoic acid;

Methyl 3-{[2-(4-amino-furazan-3-yl)-1-(2-methyl-1,3-benzoxazol-5-yl)-1H-imidazo[4,5-c]pyridin-6-yl]oxy}benzoate;

3-{[2-(4-Amino-furazan-3-yl)-1-phenyl-1H-imidazo[4,5-c]pyridin-6-yl]oxy}-N-[2-(4-morpholinyl)ethyl]benzamide;

3-{[2-(4-Amino-furazan-3'-yl)-1-phenyl-1H-imidazo[4,5-c]pyridin-6-yl]oxy}-N-[2-(4-morpholinyl)ethyl]benzamide;

4-{1-Ethyl-6-[(3-{[2-(1-methyl-3-piperidinyl)ethyl]oxy}phenyl)oxy]-1H-imidazo[4,5-c]pyridin-2-yl}-furazan-3-amine;

4-[1-Ethyl-6-({3-[4-(1-methyl-4-piperidinyl)butyl]phenyl}oxy)-1H-imidazo[4,5-c]pyridin-2-yl]-furazan-3-amine;

1-(3-{[2-(4-Amino-furazan-3-yl)-1-(1,2,3,4-tetrahydro-7-isoquinolinyl)-1H-imidazo[4,5-c]pyridin-6-yl]oxy}phenyl)ethanone;

More preferred compounds:

3-{[2-(4-Amino-furazan-3-yl)-1-ethyl-1H-imidazo[4,5-c]pyridin-6-yl]oxy}-N-(4-{[3-(dimethylamino)propyl]oxy}phenyl)benzamide;

3-{[2-(4-Amino-furazan-3-yl)-1-ethyl-1H-imidazo[4,5-c]pyridin-6-yl]oxy}-N-{4-[2-(1-pyrrolidinyl)ethyl]phenyl}benzamide;

3-{[2-(4-Amino-furazan-3-yl)-1-ethyl-1H-imidazo[4,5-c]pyridin-6-yl]oxy}-N-{4-[(dimethylamino)methyl]phenyl}benzamide;

3-{([2-(4-Amino-furazan-3-yl)-1-ethyl-1H-imidazo[4,5-c]pyridin-6-yl]oxy}-N-{4-[2-(dimethylamino)ethyl]phenyl}benzamide;

N-(3-{[2-(4-Amino-furazan-3-yl)-1-ethyl-1H-imidazo[4,5-c]pyridin-6-yl]oxy}phenyl)-4-{[2-(dimethylamino)ethyl]oxy}benzamide;

3-{[2-(4-Amino-furazan-3-yl)-1-ethyl-1H-imidazo[4,5-c]pyridin-6-yl]oxy}-N-[3-(1-methyl-4-piperidinyl)propyl]benzamide;

3-{[2-(4-Amino-furazan-3-yl)-1-ethyl-1H-imidazo[4,5-c]pyridin-6-yl]oxy}-N-(4-{[2-(dimethylamino)ethyl]oxy}phenyl)benzamide;

N-(3-{[2-(4-Amino-furazan-3-yl)-1-ethyl-1H-imidazo[4,5-]pyridin-6-yl]oxy}phenyl)-4-[(dimethylamino)methyl]benzamide;

N-(3-{[2-(4-Amino-furazan-3-yl)-1-ethyl-1H-imidazo[4,5-c]pyridin-6-yl]oxy}phenyl)-4-{[2-(diethylamino)ethyl]oxy}benzamide;

N-(3-{[2-(4-Amino-furazan-3-yl)-1-ethyl-1H-imidazo[4,5-c]pyridin-6-yl]oxy}phenyl)-4-({2-[bis(1-methylethyl)amino]ethyl}oxy)benzamide;

N-(3-{[2-(4-Amino-furazan-3-yl)-1-ethyl-1H-imidazo[4,5-c]pyridin-6-yl]oxy}phenyl)-4-{[2-(1-piperidinyl)ethyl]oxy}benzamide;

3-{[2-(4-Amino-furazan-3-yl)-1-ethyl-1H-imidazo[4,5-c]pyridin-6-yl]oxy}-N-[2-(4-methyl-1-piperazinyl)ethyl]benzamide;

3-{[2-(4-Amino-furazan-3-yl)-1-ethyl-1H-imidazo[4,5-c]pyridin-6-yl]oxy}-N-[3-(4-methyl-1-piperazinyl)propyl]benzamide;

3-{[2-(4-Amino-furazan-3-yl)-1-ethyl-1H-imidazo[4,5-c]pyridin-6-yl]oxy}-N-(4-{[2-(4-morpholinyl)ethyl]oxy}phenyl)benzamide;

N-(3-{[2-(4-Amino-furazan-3-yl)-1-ethyl-1H-imidazo[4,5-c]pyridin-6-yl]oxy}phenyl)-4-{[2-(1-pyrrolidinyl)ethyl]oxy}benzamide;

4-(Aminomethyl)-N-(3-{[2-(4-amino-furazan-3-yl)-1-ethyl-1H-imidazo[4,5-c]pyridin-6-yl]oxy}phenyl)benzamide;

N-(3-{[2-(4-Amino-furazan-3-yl)-1-ethyl-1H-imidazo[4,5-c]pyridin-6-yl]oxy}phenyl)-3-(3-pyridinyl)propanamide;

3-{[2-(4-Amino-furazan-3-yl)-1-ethyl-1H-imidazo[4,5-c]pyridin-6-yl]oxy}-N-[2-(4-piperidinyl)ethyl]benzamide;

3-{[2-(4-Amino-furazan-3-yl)-1-ethyl-1H-imidazo[4,5-c]pyridin-6-yl]oxy}-N-{2-[4-hydroxy-3-(methyloxy)phenyl]ethyl}benzamide;

3-{[2-(4-Amino-furazan-3-yl)-1-ethyl-1H-imidazo[4,5-c]pyridin-6-yl]oxy}-N-[4-(4-morpholinyl)phenyl]benzamide;

N-(3-{[2-(4-Amino-furazan-3-yl)-1-ethyl-1H-imidazo[4,5-c]pyridin-6-yl]oxy}phenyl)-3-(4-piperidinyl)propanamide;

3-{[2-(4-Amino-furazan-3-yl)-1-(4-fluorophenyl)-1H-imidazo[4,5-c]pyridin-6-yl]oxy}-N-[3-(1-methyl-4-piperidinyl)propyl]benzamide;

N-(3-{[2-(4-Amino-furazan-3-yl)-1-ethyl-1H-imidazo[4,5-c]pyridin-6-yl]oxy}phenyl)-1-methyl-1H-1,2,3-benzotriazole-5-carboxamide;

N-(3-{[2-(4-Amino-furazan-3-yl)-1-ethyl-1H-imidazo[4,5-c]pyridin-6-yl]oxy}phenyl)-3-(4-hydroxyphenyl)propanamide;

3-{[2-(4-Amino-furazan-3-yl)-1-ethyl-1H-imidazo[4,5-c]pyridin-6-yl]oxy}-N-(2-oxo-2-phenylethyl)benzamide;

1-(3-{[2-(4-Amino-furazan-3-yl)-1-ethyl-1H-imidazo[4,5-c]pyridin-6-yl]oxy}phenyl)-4-(4-methyl-1-piperazinyl)-4-oxo-1-butanone;

N-(3-{[2-(4-Amino-furazan-3-yl)-1-ethyl-1H-imidazo[4,5-c]pyridin-6-yl]oxy}phenyl)-4-(4-morpholinylmethyl)benzamide;

N-(3-{[2-(4-Amino-furazan-3-yl)-1-ethyl-1H-imidazo[4,5-c]pyridin-6-yl]oxy}phenyl)-4-{[2-(4-morpholinyl)ethyl]oxy}benzamide;

3-{[2-(4-Amino-furazan-3-yl)-1-ethyl-1H-imidazo[4,5-c]pyridin-6-yl]oxy}-N-[3-(4-methyl-1-piperazinyl)-3-oxopropyl]benzamide;

N-[4-(Acetylamino)phenyl]-3-{[2-(4-amino-furazan-3-yl)-1-ethyl-1H-imidazo[4,5-c]pyridin-6-yl]oxy}benzamide;

3-{[2-(4-Amino-furazan-3-yl)-1-ethyl-1H-imidazo[4,5-c]pyridin-6-yl]oxy}-N-[4-(dimethylamino)phenyl]benzamide;

N-(3-{[2-(4-Amino-furazan-3-yl)-1-ethyl-1H-imidazo[4,5-c]pyridin-6-yl]oxy}phenyl)-3-pyridinecarboxamide;

N-(3-{[2-(4-Amino-furazan-3-yl)-1-(4-hydroxyphenyl)-1H-imidazo[4,5-c]pyridin-6-yl]oxy}phenyl)-4-(dimethylamino)butanamide;

N-(3-{[2-(4-Amino-furazan-3-yl)-1-ethyl-1H-imidazo[4,5-c]pyridin-6-yl]oxy}phenyl)-4-(diethylamino)butanamide;

3-{[2-(4-Amino-furazan-3-yl)-1-phenyl-1H-imidazo[4,5-c]pyridin-6-yl]oxy}-N-[3-(4-methyl-1-piperazinyl)propyl]benzamide;

3-{[2-(4-Amino-furazan-3-yl)-1-ethyl-1H-imidazo[4,5-c]pyridin-6-yl]oxy}-N-[2-hydroxy-2-(4-hydroxyphenyl)ethyl]benzamide;

3-{[2-(4-Amino-furazan-3-yl)-1-ethyl-1H-imidazo[4,5-c]pyridin-6-yl]oxy}-N-[2-(tetrahydro-2H-pyran-4-yl)ethyl]benzamide;

N-(3-{[2-(4-Amino-furazan-3-yl)-1-ethyl-1H-imidazo[4,5-c]pyridin-6-yl]oxy}phenyl)-4-{[3-(1-piperidinyl)propyl]oxy}benzamide;

N-[4-(Aminocarbonyl)phenyl]-3-{[2-(4-amino-furazan-3-yl)-1-ethyl-1H-imidazo[4,5-c]pyridin-6-yl]oxy}benzamide;

N-(3-{[2-(4-Amino-furazan-3-yl)-1-ethyl-1H-imidazo[4,5-c]pyridin-6-yl]oxy}phenyl)-4-{[2-(4-morpholinyl)ethyl]oxy}benzamide;

3-{[2-(4-Amino-furazan-3-yl)-1-ethyl-1H-imidazo[4,5-c]pyridin-6-yl]oxy}-N-(4-piperidinylmethyl)benzamide;

N-(3-{[2-(4-Amino-furazan-3-yl)-1-ethyl-1H-imidazo[4,5-c]pyridin-6-yl]oxy}phenyl)-4-(methylamino)butanamide;

3-{[2-(4-Amino-furazan-3-yl)-1-phenyl-1H-imidazo[4,5-c]pyridin-6-yl]oxy}-N-[2-(4-hydroxyphenyl)ethyl]benzamide;

3-{[2-(4-Amino-furazan-3-yl)-1-ethyl-1H-imidazo[4,5-c]pyridin-6-yl]oxy}-N-{4-[(1,1-dioxido-4-thiomorpholinyl)methyl]phenyl}benzamide;

3-{[2-(4-Amino-furazan-3-yl)-1-ethyl-1H-imidazo[4,5-c]pyridin-6-yl]oxy}-N-[3-(1-piperidinyl)propyl]benzamide;

N-(3-{[2-(4-Amino-furazan-3-yl)-1-(1,2,3,4-tetrahydro-7-isoquinolinyl)-1H-imidazo[4,5-c]pyridin-6-yl]oxy}phenyl)acetamide;

4-{1-Ethyl-6-[(3-{[4-(1-methyl-4-piperidinyl)butyl]oxy}phenyl)oxy]-1H-imidazo[4,5-c]pyridin-2-yl}-furazan-3-amine;

N-(3-{[2-(4-Amino-furazan-3-yl)-1-ethyl-1H-imidazo[4,5-c]pyridin-6-yl]oxy}phenyl)-4-(1H-imidazol-1-yl)benzamide;

N-(3-{[2-(4-Amino-furazan-3-yl)-1-ethyl-1H-imidazo[4,5-c]pyridin-6-yl]oxy}phenyl)-4-(4-morpholinyl)butanamide;

3-{[2-(4-Amino-furazan-3-yl)-1-(4-hydroxyphenyl)-1H-imidazo[4,5-c]pyridin-6-yl]oxy}-N-[2-(4-morpholinyl)ethyl]benzamide;

3-{[2-(4-Amino-furazan-3-yl)-1-ethyl-1H-imidazo[4,5-c] pyridin-6-yl]oxy}-N-[4-(methyloxy)phenyl]benzamide;
1-(3-{[2-(4-Amino-furazan-3-yl)-1-ethyl-1H-imidazo[4,5-c]pyridin-6-yl]oxy}phenyl)-4-(4-morpholinyl)-1-butanone;
N-(3-{[2-(4-Amino-furazan-3-yl)-1-ethyl-1H-imidazo[4,5-c]pyridin-6-yl]oxy}phenyl)-3,4-bis(methyloxy)benzamide;
N-(3-{[2-(4-Amino-furazan-3-yl)-1-(4-{[2-(dimethylamino)ethyl]oxy}phenyl)-1H-imidazo[4,5-c]pyridin-6-yl]oxy}phenyl)-6-methyl-3-pyridinecarboxamide;
3-{[2-(4-Amino-furazan-3-yl)-1-ethyl-1H-imidazo[4,5-c]pyridin-6-yl]oxy}-N-[2-(4-thiomorpholinyl)ethyl]benzamide;
N-[4-(Aminomethyl)phenyl]-3-{[2-(4-amino-furazan-3-yl)-1-phenyl-1H-imidazo[4,5-c]pyridin-6-yl]oxy}benzamide;
N-(3-{[2-(4-Amino-furazan-3-yl)-1-ethyl-1H-imidazo[4,5-c]pyridin-6-yl]oxy}phenyl)-2,3-dihydro-1-benzofuran-5-carboxamide;
N-[2-(4-Acetyl-1-piperazinyl)ethyl]-3-{[2-(4-amino-furazan-3-yl)-1-ethyl-1H-imidazo[4,5-c]pyridin-6-yl]oxy}benzamide;
3-{[2-(4-Amino-furazan-3-yl)-1-(4-fluorophenyl)-1H-imidazo[4,5-c]pyridin-6-yl]oxy}-N-[3-(4-methyl-1-piperazinyl)propyl]benzamide;
N-[3-{[2-(4-Amino-furazan-3-yl)-1-ethyl-1H-imidazo[4,5-c]pyridin-6-yl]oxy}-5-(trifluoromethyl)phenyl]acetamide;
N-(3-{[2-(4-Amino-furazan-3-yl)-1-ethyl-1H-imidazo[4,5-c]pyridin-6-yl]oxy}phenyl)urea;
3-{[2-(4-Amino-furazan-3-yl)-1-ethyl-1H-imidazo[4,5-c]pyridin-6-yl]oxy}-N-[2-(4-morpholinyl)ethyl]benzamide;
N-(3-{[2-(4-Amino-furazan-3-yl)-1-ethyl-1H-imidazo[4,5-c]pyridin-6-yl]oxy}phenyl)-4-hydroxybenzamide;
3-{[2-(4-Amino-furazan-3-yl)-1-(4-fluorophenyl)-1H-imidazo[4,5-c]pyridin-6-yl]oxy}-N-[3-(4-methyl-1-piperazinyl)-3-oxopropyl]benzamide;
N-(3-{[2-(4-Amino-furazan-3-yl)-1-ethyl-1H-imidazo[4,5-c]pyridin-6-yl]oxy}phenyl)-4-(4-morpholinyl)benzamide;
N-(3-{[2-(4-Amino-furazan-3-yl)-1-(4-{[2-(dimethylamino)ethyl]oxy}phenyl)-1H-imidazo[4,5-c]pyridin-6-yl]oxy}phenyl)-4-(methyloxy)benzamide;
N-(3-{[1-{4-[(2-Aminoethyl)oxy]phenyl}-2-(4-amino-furazan-3-yl)-1H-imidazo[4,5-c]pyridin-6-yl]oxy}phenyl)acetamide;
N-(3-{[2-(4-Amino-furazan-3-yl)-1-ethyl-1H-imidazo[4,5-c]pyridin-6-yl]oxy}phenyl)-6-methyl-3-pyridinecarboxamide;
N-(3-{[2-(4-Amino-furazan-3-yl)-1-ethyl-1H-imidazo[4,5-c]pyridin-6-yl]oxy}phenyl)-2-methyl-1,3-thiazole-5-carboxamide;
N-(3-{[2-(4-Amino-furazan-3-yl)-1-ethyl-1H-imidazo[4,5-c]pyridin-6-yl]oxy}phenyl)-4-(dimethylamino)butanamide;
N-(3-{[2-(4-Amino-furazan-3-yl)-1-ethyl-1H-imidazo[4,5-c]pyridin-6-yl]oxy}phenyl)-4-{[3-(1-piperazinyl)propyl]oxy}benzamide;
N-(3-{[2-(4-Amino-furazan-3-yl)-1-ethyl-1H-imidazo[4,5-c]pyridin-6-yl]oxy}phenyl)-2-(dimethylamino)-5-pyrimidinecarboxamide;
3-({2-(4-Amino-furazan-3-yl)-1-[2-(methyloxy)phenyl]-1H-imidazo[4,5-c]pyridin-6-yl}oxy)-N-[3-(4-methyl-1-piperazinyl)propyl]benzamide;

4-{1-Ethyl-6-[(3-{[2-(1-methyl-4-piperidinyl)ethyl]oxy}phenyl)oxy]-1H-imidazo[4,5-c]pyridin-2-yl}-furazan-3-amine;
3-{[2-(4-Amino-furazan-3-yl)-1-ethyl-1H-imidazo[4,5-c]pyridin-6-yl]oxy}-N-[3-(2-oxo-1-pyrrolidinyl)propyl]benzamide;
N-(3-{[2-(4-Amino-furazan-3-yl)-1-ethyl-1H-imidazo[4,5-c]pyridin-6-yl]oxy}phenyl)-2-furancarboxamide;
3-{[2-(4-Amino-furazan-3-yl)-1-phenyl-1H-imidazo[4,5-c]pyridin-6-yl]oxy}-N-[2-(3-pyridinyl)ethyl]benzamide;
N-(3-{[2-(4-Amino-furazan-3-yl)-1-ethyl-1H-imidazo[4,5-c]pyridin-6-yl]oxy}phenyl)-4-[(1-methyl-4-piperidinyl)oxy]benzamide;
N-(3-{[2-(4-Amino-furazan-3-yl)-1-(4-{[2-(methylamino)ethyl]oxy}phenyl)-1H-imidazo[4,5-c]pyridin-6-yl]oxy}phenyl)acetamide;
N-[3-({2-(4-Amino-furazan-3-yl)-1-[4-({[(2S)-1-methyl-2-pyrrolidinyl]methyl}oxy)phenyl]-1H-imidazo[4,5-c]pyridin-6-yl}oxy)phenyl]acetamide;
N-(3-{[2-(4-Amino-furazan-3-yl)-1-ethyl-1H-imidazo[4,5-c]pyridin-6-yl]oxy}phenyl)-4-(dimethylamino)benzamide;
N-(3-{[2-(4-Amino-furazan-3-yl)-1-ethyl-1H-imidazo[4,5-c]pyridin-6-yl]oxy}phenyl)-4-(2-oxo-1-pyrrolidinyl)butanamide;
N~1~-(3-{[2-(4-Amino-furazan-3-yl)-1-ethyl-1H-imidazo[4,5-c]pyridin-6-yl]oxy}phenyl)-N~3~,N~3~-dimethyl-beta-alaninamide
N-(3-{[2-(4-Amino-furazan-3-yl)-1-ethyl-1H-imidazo[4,5-c]pyridin-6-yl]oxy}phenyl)-2-(methyloxy)acetamide;
3-{[2-(4-Amino-furazan-3-yl)-1-phenyl-1H-imidazo[4,5-c]pyridin-6-yl]oxy}-N-[3-(1H-imidazol-1-yl)propyl]benzamide;
3-{[2-(4-Amino-furazan-3-yl)-1-phenyl-1H-imidazo[4,5-c]pyridin-6-yl]oxy}-N-[2-(4-pyridinyl)ethyl]benzamide;
N-(3-{[2-(4-Amino-furazan-3-yl)-1-ethyl-1H-imidazo[4,5-c]pyridin-6-yl]oxy}phenyl)-6-(1H-pyrazol-1-yl)-3-pyridinecarboxamide;
N-(3-{[2-(4-Amino-furazan-3-yl)-1-(4-{[2-(1-pyrrolidinyl)ethyl]oxy}phenyl)-1H-imidazo[4,5-c]pyridin-6-yl]oxy}phenyl)acetamide;
3-{[2-(4-Amino-furazan-3-yl)-1-ethyl-1H-imidazo[4,5-c]pyridin-6-yl]oxy}-N-[2-(1-oxido-4-thiomorpholinyl)ethyl]benzamide;
N-(3-{[2-(4-Amino-furazan-3-yl)-1-ethyl-1H-imidazo[4,5-c]pyridin-6-yl]oxy}phenyl)-4-{[2-(1-piperazinyl)ethyl]oxy}benzamide;
N-(3-{[2-(4-Amino-furazan-3-yl)-1-ethyl-1H-imidazo[4,5-c]pyridin-6-yl]oxy}phenyl)-4-(1-piperidinyl)benzamide;
N-(3-{[2-(4-Amino-furazan-3-yl)-1-ethyl-1H-imidazo[4,5-c]pyridin-6-yl]oxy}phenyl)-4-(methyloxy)benzamide;
N-(3-{[2-(4-Amino-furazan-3-yl)-1-ethyl-1H-imidazo[4,5-c]pyridin-6-yl]oxy}phenyl)benzamide;
N-(3-{[2-(4-Amino-furazan-3-yl)-1-(4-{[2-(diethylamino)ethyl]oxy}phenyl)-1H-imidazo[4,5-c]pyridin-6-yl]oxy}phenyl)acetamide;
4-{1-Ethyl-6-[(3-{[3-(1-methyl-4-piperidinyl)propyl]oxy}phenyl)oxy]-1H-imidazo[4,5-c]pyridin-2-yl}-furazan-3-amine;
3-{[2-(4-Amino-furazan-3-yl)-1-ethyl-1H-imidazo[4,5-c]pyridin-6-yl]oxy}phenol;
N-(3-{[2-(4-Amino-furazan-3-yl)-1-ethyl-1H-imidazo[4,5-c]pyridin-6-yl]oxy}phenyl)-4-(ethyloxy)benzamide;
3-{[2-(4-Amino-furazan-3-yl)-1-phenyl-1H-imidazo[4,5-c]pyridin-6-yl]oxy}-N-(1,4-dioxan-2-ylmethyl)benzamide;

N-(3-{[2-(4-Amino-furazan-3-yl)-1-ethyl-1H-imidazo[4,5-c]pyridin-6-yl]oxy}phenyl)-2-methyl-3-pyridinecarboxamide;

N-(3-{[2-(4-Amino-furazan-3-yl)-1-ethyl-1H-imidazo[4,5-c]pyridin-6-yl]oxy}phenyl)butanamide;

N-(3-{[2-(4-Amino-furazan-3-yl)-1-ethyl-1H-imidazo[4,5-c]pyridin-6-yl]oxy}phenyl)-4-methyl-3,4-dihydro-2H-1,4-benzoxazine-7-carboxamide;

4-{2-(4-Amino-furazan-3-yl)-6-[(4-fluorophenyl)oxy]-1H-imidazo[4,5-c]pyridin-1-yl}phenol;

3-{[2-(4-Amino-furazan-3-yl)-1-(1H-benzimidazol-5-yl)-1H-imidazo[4,5-c]pyridin-6-yl]oxy}-N-[3-(2-oxo-1-pyrrolidinyl)propyl]benzamide;

3-{[2-(4-Amino-furazan-3-yl)-1-phenyl-1H-imidazo[4,5-c]pyridin-6-yl]oxy}-N-(tetrahydro-2-furanylmethyl)benzamide;

3-{[2-(4-Amino-furazan-3-yl)-1-phenyl-1H-imidazo[4,5-c]pyridin-6-yl]oxy}-N-[3-(dimethylamino)propyl]benzamide;

3-{[2-(4-Amino-furazan-3-yl)-1-(4-bromophenyl)-1H-imidazo[4,5-c]pyridin-6-yl]oxy}-N-[3-(4-methyl-1-piperazinyl)-3-oxopropyl]benzamide;

N-(3-{[2-(4-Amino-furazan-3-yl)-1-ethyl-1H-imidazo[4,5-c]pyridin-6-yl]oxy}phenyl)-4-(dimethylamino)butanamide;

N-(3-{[2-(4-Amino-furazan-3-yl)-1-ethyl-1H-imidazo[4,5-c]pyridin-6-yl]oxy}phenyl)-4-fluorobenzamide;

4-(Aminomethyl)-N-(3-{[2-(4-amino-furazan-3-yl)-1-phenyl-1H-imidazo[4,5-c]pyridin-6-yl]oxy}phenyl)benzamide;

N-(3-{[2-(4-Amino-furazan-3-yl)-1-ethyl-1H-imidazo[4,5-c]pyridin-6-yl]oxy}phenyl)-6-{[2-(4-morpholinyl)ethyl]oxy}-3-pyridinecarboxamide;

N-(3-{[2-(4-Amino-furazan-3-yl)-1-(4-{[2-(1-piperidinyl)ethyl]oxy}phenyl)-1H-imidazo[4,5-c]pyridin-6-yl]oxy}phenyl)acetamide;

3-{[2-(4-Amino-furazan-3-yl)-1-phenyl-1H-imidazo[4,5-c]pyridin-6-yl]oxy}-N-[2-(4-morpholinyl)ethyl]benzamide;

N-(3-{[2-(4-Amino-furazan-3-yl)-1-ethyl-1H-imidazo[4,5-c]pyridin-6-yl]oxy}phenyl)-3-chloro-4-(methyloxy)benzamide;

3-{[2-(4-Amino-furazan-3-yl)-1-(4-piperidinyl)-1H-imidazo[4,5-c]pyridin-6-yl]oxy}-N-[3-(4-methyl-1-piperazinyl)-3-oxopropyl]benzamide;

3-{[2-(4-Amino-furazan-3-yl)-1-phenyl-1H-imidazo[4,5-c]pyridin-6-yl]oxy}-N-[3-(1-pyrrolidinyl)propyl]benzamide;

N-(3-{[2-(4-Amino-furazan-3-yl)-1-(cyclopropylmethyl)-1H-imidazo[4,5-c]pyridin-6-yl]oxy}phenyl)-4-{[2-(4-morpholinyl)ethyl]oxy}benzamide;

N-(3-{[2-(4-Amino-furazan-3-yl)-1-ethyl-1H-imidazo[4,5-c]pyridin-6-yl]oxy}phenyl)-3-fluoro-4-(methyloxy)benzamide;

3-{[2-(4-Amino-furazan-3-yl)-1-(cyclopropylmethyl)-1H-imidazo[4,5-c]pyridin-6-yl]oxy}-N-[2-(4-morpholinyl)ethyl]benzamide;

N-(3-{[2-(4-Amino-furazan-3-yl)-1-ethyl-1H-imidazo[4,5-c]pyridin-6-yl]oxy}phenyl)-3-(methyloxy)benzamide;

3-({2-(4-Amino-furazan-3-yl)-1-[2-(methyloxy)phenyl]-1H-imidazo[4,5-c]pyridin-6-yl}oxy)-N-[2-(4-morpholinyl)ethyl]benzamide;

N-(3-{[2-(4-Amino-furazan-3-yl)-1-ethyl-1H-imidazo[4,5-c]pyridin-6-yl]oxy}phenyl)-3-(3-hydroxyphenyl)propanamide;

N-(3-{[2-(4-Amino-furazan-3-yl)-1-(4-{[2-(dimethylamino)ethyl]oxy}phenyl)-1H-imidazo[4,5-c]pyridin-6-yl]oxy}phenyl)acetamide;

4-[6-[(4-Fluorophenyl)oxy]-1-(1,2,3,4-tetrahydro-7-isoquinolinyl)-1H-imidazo[4,5-c]pyridin-2-yl]-furazan-3-amine;

3-{[2-(4-Amino-furazan-3-yl)-1-(1,2,3,4-tetrahydro-7-isoquinolinyl)-1H-imidazo[4,5-c]pyridin-6-yl]oxy}-N-[3-(2-oxo-1-pyrrolidinyl)propyl]benzamide;

3-{[2-(4-Amino-furazan-3-yl)-1-(4-fluorophenyl)-1H-imidazo[4,5-c]pyridin-6-yl]oxy}-N-[2-(4-morpholinyl)ethyl]benzamide;

N-(3-{[2-(4-Amino-furazan-3-yl)-1-ethyl-1H-imidazo[4,5-c]pyridin-6-yl]oxy}phenyl)-6-[(2,2,2-trifluoroethyl)oxy]-3-pyridinecarboxamide;

N-(3-{[2-(4-Amino-furazan-3-yl)-1-ethyl-1H-imidazo[4,5-c]pyridin-6-yl]oxy}phenyl)-N'-methylurea;

3-{[2-(4-Amino-furazan-3-yl)-1-phenyl-1H-imidazo[4,5-c]pyridin-6-yl]oxy}-N-[3-(4-morpholinyl)propyl]benzamide;

N-(3-{[2-(4-Amino-furazan-3-yl)-1-phenyl-1H-imidazo[4,5-c]pyridin-6-yl]oxy}phenyl)-4-{[2-(4-morpholinyl)ethyl]oxy}benzamide;

3-{[2-(4-Amino-furazan-3-yl)-1-phenyl-1H-imidazo[4,5-c]pyridin-6-yl]oxy}-N-[4-(methyloxy)phenyl]benzamide;

4-(6-{[3-Amino-5-(trifluoromethyl)phenyl]oxy}-1-ethyl-1H-imidazo[4,5-c]pyridin-2-yl)-furazan-3-amine;

N-(3-{[2-(4-Amino-furazan-3-yl)-1-ethyl-1H-imidazo[4,5c]pyridin-6-yl]oxy}phenyl)-1-methyl-4-piperidinecarboxamide;

3-{[2-(4-Amino-furazan-3-yl)-1-phenyl-1H-imidazo[4,5-c]pyridin-6-yl]oxy}-N-[2-(1-pyrrolidinyl)ethyl]benzamide;

3-({2-(4-Amino-furazan-3-yl)-1-[2-(methyloxy)phenyl]-1H-imidazo[4,5-c]pyridin-6-yl}oxy)-N-[3-(2-oxo-1-pyrrolidinyl)propyl]benzamide;

3-{[2-(4-Amino-furazan-3-yl)-1-phenyl-1H-imidazo[4,5-c]pyridin-6-yl]oxy}-N-(3-amino-3-oxopropyl)benzamide;

N-(3-{[2-(4-Amino-furazan-3-yl)-1-(4-hydroxyphenyl)-1H-imidazo[4,5-c]pyridin-6-yl]oxy}phenyl)methanesulfonamide;

3-{[2-(4-Amino-furazan-3-yl)-1-phenyl-1H-imidazo[4,5-c]pyridin-6-yl]oxy}-N-(4-pyridinylmethyl)benzamide;

N'-(3-{[2-(4-Amino-furazan-3-yl)-1-(4-hydroxyphenyl)-1H-imidazo[4,5-c]pyridin-6-yl]oxy}phenyl)-N,N-dimethylsulfamide;

Methyl 3-{[2-(4-amino-furazan-3-yl)-1-(1H-benzimidazol-5-yl)-1H-imidazo[4,5-c]pyridin-6-yl]oxy}benzoate;

N-{3-[(2-(4-Amino-furazan-3-yl)-1-{4-[(cyanomethyl)oxy]phenyl}-1H-imidazo[4,5-c]pyridin-6-yl)oxy]phenyl}acetamide;

3-{[2-(4-Amino-furazan-3-yl)-1-phenyl-1H-imidazo[4,5-c]pyridin-6-yl]oxy}-N-[2-(2-pyridinyl)ethyl]benzamide;

N-(3-{[2-(4-Amino-furazan-3-yl)-1-(4-{[2-(dimethylamino)ethyl]oxy}phenyl)-1H-imidazo[4,5-c]pyridin-6-yl]oxy}phenyl)-N'-methylurea;

3-{[2-(4-Amino-furazan-3-yl)-1-ethyl-1H-imidazo[4,5-c]pyridin-6-yl]oxy}-N-[2-(1,1-dioxido-4-thiomorpholinyl)ethyl]benzamide;

N-(3-{[2-(4-Amino-furazan-3-yl)-1-phenyl-1H-imidazo[4,5-c]pyridin-6-yl]oxy}phenyl)acetamide;

3-{[2-(4-Amino-furazan-3-yl)-1-phenyl-1H-imidazo[4,5-c]pyridin-6-yl]oxy}-N-[3-(2-oxo-1-pyrrolidinyl)propyl]benzamide;

4-{1-Ethyl-6-[(3-{[(1-methyl-4-piperidinyl)methyl]oxy}phenyl)oxy]-1H-imidazo[4,5-c]pyridin-2-yl}-furazan-3-amine;

N-(3-{[2-(4-Amino-furazan-3-yl)-1-ethyl-1H-imidazo[4,5-c]pyridin-6-yl]oxy}phenyl)pyrazolo[1,5-a]pyridine-3-carboxamide;

N-(3-{[2-(4-Amino-furazan-3-yl)-1-(4-hydroxyphenyl)-1H-imidazo[4,5-c]pyridin-6-yl]oxy}phenyl)acetamide;

3-{[2-(4-Amino-furazan-3-yl)-1-phenyl-1H-imidazo[4,5-c]pyridin-6-yl]oxy}-N-[2-(dimethylamino)ethyl]benzamide;

N-(3-{[2-(4-Amino-furazan-3-yl)-1-ethyl-1H-imidazo[4,5-c]pyridin-6-yl]oxy}phenyl)-4-(3,5-dimethyl-1H-pyrazol-1-yl)benzamide;

3-({2-(4-Amino-furazan-3-yl)-1-[4-(trifluoromethyl)phenyl]-1H-imidazo[4,5-c]pyridin-6-yl}oxy)-N-[3-(4-methyl-1-piperazinyl)propyl]benzamide;

N-(3-{[2-(4-Amino-furazan-3-yl)-1-(4-{[2-(dimethylamino)ethyl]oxy}phenyl)-1H-imidazo[4,5-c]pyridin-6-yl]oxy}phenyl)methanesulfonamide;

3-{[2-(4-Amino-furazan-3-yl)-1-(4-fluorophenyl)-1H-imidazo[4,5-c]pyridin-6-yl]oxy}-N-[3-(2-oxo-1-pyrrolidinyl)propyl]benzamide;

N-(3-{[2-(4-Amino-furazan-3-yl)-1-ethyl-1H-imidazo[4,5-c]pyridin-6-yl]oxy}phenyl)-1-methyl-4-piperidinecarboxamide;

1-(3-{[2-(4-Amino-furazan-3-yl)-1-ethyl-1H-imidazo[4,5-c]pyridin-6-yl]oxy}phenyl)ethanone;

N-(3-{[2-(4-Amino-furazan-3-yl)-1-ethyl-1H-imidazo[4,5-c]pyridin-6-yl]oxy}phenyl)-4-cyanobenzamide;

3-{[2-(4-Amino-furazan-3-yl)-1-(1H-indazol-5-yl)-1H-imidazo[4,5-c]pyridin-6-yl]oxy}-N-[3-(2-oxo-1-pyrrolidinyl)propyl]benzamide;

N-(3-{[2-(4-Amino-furazan-3-yl)-1-ethyl-1H-imidazo[4,5-c]pyridin-6-yl]oxy}phenyl)-N'-(phenylmethyl)urea;

3-{[2-(4-Amino-furazan-3-yl)-1-phenyl-1H-imidazo[4,5-c]pyridin-6-yl]oxy}-N-[2-(1-methyl-1H-pyrrol-2-yl)ethyl]benzamide;

N-(3-{[2-(4-Amino-furazan-3-yl)-1-phenyl-1H-imidazo[4,5-c]pyridin-6-yl]oxy}phenyl)-4-(2-oxo-1-pyrrolidinyl)butanamide;

N-(3-{[2-(4-Amino-furazan-3-yl)-1-(4-{[2-(4-morpholinyl)ethyl]oxy}phenyl)-1H-imidazo[4,5-c]pyridin-6-yl]oxy}phenyl)acetamide;

3-{[2-(4-Amino-furazan-3-yl)-1-phenyl-1H-imidazo[4,5-c]pyridin-6-yl]oxy}-N-[4-(dimethylamino)phenyl]benzamide;

3-{[2-(4-Amino-furazan-3-yl)-1-(4-piperidinyl)-1H-imidazo[4,5-c]pyridin-6-yl]oxy}-N-[3-(2-oxo-1-pyrrolidinyl)propyl]benzamide;

4-[6-(1H-Benzimidazol-4-yloxy)-1-phenyl-1H-imidazo[4,5-c]pyridin-2-yl]-furazan-3-amine;

N-(3-{[2-(4-Amino-furazan-3-yl)-1-ethyl-1H-imidazo[4,5-c]pyridin-6-yl]oxy}phenyl)-2-methylpropanamide;

3-({2-(4-Amino-furazan-3-yl)-1-[3-(methyloxy)propyl]-1H-imidazo[4,5-c]pyridin-6-yl}oxy)-N-[2-(4-morpholinyl)ethyl]benzamide;

N-(3-{[2-(4-Amino-furazan-3-yl)-1-ethyl-1H-imidazo[4,5-c]pyridin-6-yl]oxy}phenyl)methanesulfonamide;

3-({2-(4-Amino-furazan-3-yl)-1-[2-(methyloxy)ethyl]-1H-imidazo[4,5-c]pyridin-6-yl}oxy)-N-[2-(4-morpholinyl)ethyl]benzamide;

N-(3-{[2-(4-Amino-furazan-3-yl)-1-ethyl-1H-imidazo[4,5-c]pyridin-6-yl]oxy}phenyl)-2-(methyloxy)-3-pyridinecarboxamide;

N-(3-{[2-(4-Amino-furazan-3-yl)-1-ethyl-1H-imidazo[4,5-c]pyridin-6-yl]oxy}phenyl)-4-morpholinecarboxamide;

N'-(3-{[2-(4-Amino-furazan-3-yl)-1-ethyl-1H-imidazo[4,5-c]pyridin-6-yl]oxy}phenyl)-N,N-dimethylsulfamide;

N-[2-(Acetylamino)ethyl]-3-{[2-(4-amino-furazan-3-yl)-1-phenyl-1H-imidazo[4,5-c]pyridin-6-yl]oxy}benzamide;

3-{[2-(4-Amino-furazan-3-yl)-1-phenyl-1H-imidazo[4,5-c]pyridin-6-yl]oxy}-N-[2-(methyloxy)ethyl]benzamide;

3-{[2-(4-Amino-furazan-3-yl)-1-phenyl-1H-imidazo[4,5-c]pyridin-6-yl]oxy}-N-(2-cyanoethyl)benzamide;

3-({2-(4-Amino-furazan-3-yl)-1-[2-(methyloxy)ethyl]-1H-imidazo[4,5-c]pyridin-6-yl}oxy)-N-[3-(4-methyl-1-piperazinyl)-3-oxopropyl]benzamide;

4-(1-Ethyl-6-{[3-(methylsulfonyl)phenyl]oxy}-1H-imidazo[4,5-c]pyridin-2-yl)-furazan-3-amine;

N-(3-{[2-(4-Amino-furazan-3-yl)-1-ethyl-1H-imidazo[4,5-c]pyridin-6-yl]oxy}phenyl)-4-chloro-2-pyridinecarboxamide;

N-(3-{[2-(4-Amino-furazan-3-yl)-1-ethyl-1H-imidazo[4,5-c]pyridin-6-yl]oxy}phenyl)-4-(trifluoromethyl)-3-pyridinecarboxamide;

N'-(3-{[2-(4-Amino-furazan-3-yl)-1-(4-{[2-(dimethylamino)ethyl]oxy}phenyl)-1H-imidazo[4,5-c]pyridin-6-yl]oxy}phenyl)-N,N-dimethylsulfamide;

4-{6-[(3-Aminophenyl)oxy]-1-ethyl-1H-imidazo[4,5-c]pyridin-2-yl}-furazan-3-amine;

Methyl 3-{[2-(4-amino-furazan-3-yl)-1-ethyl-1H-imidazo[4,5-c]pyridin-6-yl]oxy}benzoate;

3-{[2-(4-Amino-furazan-3-yl)-1-phenyl-1H-imidazo[4,5-c]pyridin-6-yl]oxy}-N-[(1,5-dimethyl-1H-pyrazol-4-yl)methyl]benzamide;

N-(3-{[2-(4-Amino-furazan-3-yl)-1-(4-{[2-(dimethylamino)ethyl]oxy}phenyl)-1H-imidazo[4,5-c]pyridin-6-yl]oxy}phenyl)-2-methylpropanamide;

N-(3-{[2-(4-Amino-furazan-3-yl)-1-phenyl-1H-imidazo[4,5-c]pyridin-6-yl]oxy}phenyl)-3-(4-morpholinyl)propanamide;

4-[1-Ethyl-6-({3-[(1E)-3-(4-methyl-1-piperazinyl)-3-oxo-1-propen-1-yl]phenyl}oxy)-1H-imidazo[4,5-c]pyridin-2-yl]-furazan-3-amine;

N-(3-{[2-(4-Amino-furazan-3-yl)-1-ethyl-1H-imidazo[4,5-c]pyridin-6-yl]oxy}phenyl)-N'-phenylurea;

3-{[2-(4-Amino-furazan-3-yl)-1-(1,3-benzodioxol-5-yl)-1H-imidazo[4,5-c]pyridin-6-yl]oxy}-N-[3-(2-oxo-1-pyrrolidinyl)propyl]benzamide;

4-{1-[4-(Aminomethyl)phenyl]-6-[(4-fluorophenyl)oxy]-1H-imidazo[4,5-c]pyridin-2-yl}-furazan-3-amine;

3-{[2-(4-Amino-furazan-3-yl)-1-ethyl-1H-imidazo[4,5-c]pyridin-6-yl]oxy}benzoic acid;

N-(5-{[2-(4-Amino-furazan-3-yl)-1-ethyl-1H-imidazo[4,5-c]pyridin-6-yl]oxy}-2-chlorophenyl)acetamide;

4-{1-(2,3-Dihydro-1H-isoindol-5-yl)-6-[(4-fluorophenyl)oxy]-1H-imidazo[4,5-c]pyridin-2-yl}-furazan-3-amine;

3-{[2-(4-Amino-furazan-3-yl)-1-phenyl-1H-imidazo[4,5-c]pyridin-6-yl]oxy}-N-methylbenzamide;

3-{[2-(4-Amino-furazan-3-yl)-1-phenyl-1H-imidazo[4,5-c]pyridin-6-yl]oxy}benzamide;

3-{[2-(4-Amino-furazan-3-yl)-1-(4-bromophenyl)-1H-imidazo[4,5-c]pyridin-6-yl]oxy}-N-[3-(2-oxo-1-pyrrolidinyl)propyl]benzamide;

4-{6-[(3-{[3-(4-Acetyl-1-piperazinyl)propyl]oxy}phenyl)oxy]-1-ethyl-1H-imidazo[4,5-c]pyridin-2-yl}-furazan-3-amine;

N-(3-{[2-(4-Amino-furazan-3-yl)-1-ethyl-1H-imidazo[4,5-c]pyridin-6-yl]oxy}phenyl)-1-methyl-1H-imidazole-2-carboxamide;

3-({2-(4-Amino-furazan-3-yl)-1-[2-(methyloxy)ethyl]-1H-imidazo[4,5-c]pyridin-6-yl}oxy)-N-[3-(2-oxo-1-pyrrolidinyl)propyl]benzamide trifluoroacetate;

3-{[2-(4-Amino-furazan-3-yl)-1-phenyl-1H-imidazo[4,5-c]pyridin-6-yl]oxy}-N-ethylbenzamide;

N-(4-{[2-(4-Amino-furazan-3-yl)-1-(4-{[2-(dimethylamino)ethyl]oxy}phenyl)-1H-imidazo[4,5-c]pyridin-6-yl]oxy}phenyl)acetamide;

N-[3-({2-(4-Amino-furazan-3-yl)-1-[2-(methyloxy)ethyl]-1H-imidazo[4,5-c]pyridin-6-yl}oxy)phenyl]acetamide;

N-(4-{[2-(4-Amino-furazan-3-yl)-1-(4-hydroxyphenyl)-1H-imidazo[4,5-c]pyridin-6-yl]oxy}phenyl)acetamide;

4-(1-(1,2,3,4-Tetrahydro-7-isoquinolinyl)-6-{[4-(trifluoromethyl)phenyl]oxy}-1H-imidazo[4,5-c]pyridin-2-yl)-furazan-3-amine;

4-[6-[(4-Fluorophenyl)oxy]-1-(4-{[2-(methylamino)ethyl]oxy}phenyl)-1H-imidazo[4,5-c]pyridin-2-yl]-furazan-3-amine;

N-[3-({2-(4-Amino-furazan-3-yl)-1-[3-(methyloxy)propyl]-1H-imidazo[4,5-c]pyridin-6-yl}oxy)phenyl]acetamide;

3-{[2-(4-Amino-furazan-3-yl)-1-phenyl-1H-imidazo[4,5-c]pyridin-6-yl]oxy}-N-[(4-methyl-1,3-thiazol-2-yl)methyl]benzamide;

1-(3-{[2-(4-Amino-furazan-3-yl)-1-ethyl-1H-imidazo[4,5-c]pyridin-6-yl]oxy}phenyl)-4-(4-morpholinyl)-1-butanol;

methyl 3-{[2-(4-Amino-furazan-3-yl)-1-(1H-indazol-5-yl)-1H-imidazo[4,5-c]pyridin-6-yl]oxy}benzoate;

N-(3-{[2-(4-Amino-furazan-3-yl)-1-phenyl-1H-imidazo[4,5-c]pyridin-6-yl]oxy}phenyl)-3-(2-oxo-1-pyrrolidinyl)propanamide;

4-{1-Ethyl-6-[(3-{[(1-methyl-3-piperidinyl)methyl]oxy}phenyl)oxy]-1H-imidazo[4,5-c]pyridin-2-yl}-furazan-3-amine;

3-({2-(4-Amino-furazan-3-yl)-1-[3-(methyloxy)propyl]-1H-imidazo[4,5-c]pyridin-6-yl}oxy)-N-[3-(2-oxo-1-pyrrolidinyl)propyl]benzamide;

N-(3-{[2-(4-Amino-furazan-3-yl)-1-ethyl-1H-imidazo[4,5-c]pyridin-6-yl]oxy}phenyl)-4-(methyloxy)benzenesulfonamide;

N-(3-{[2-(4-Amino-furazan-3-yl)-1-ethyl-1H-imidazo[4,5-c]pyridin-6-yl]oxy}phenyl)cyclohexanecarboxamide;

3-{[2-(4-Amino-furazan-3-yl)-1-phenyl-1H-imidazo[4,5-c]pyridin-6-yl]oxy}-N-{[4-(methyloxy)phenyl]methyl}benzamide;

3-{[2-(4-Amino-furazan-3-yl)-1-phenyl-1H-imidazo[4,5-c]pyridin-6-yl]oxy}-N-(cyclopropylmethyl)benzamide;

3-{[2-(4-Amino-furazan-3-yl)-1-phenyl-1H-imidazo[4,5-c]pyridin-6-yl]oxy}-N-(1,3-benzodioxol-5-ylmethyl)benzamide, N-(3-{[2-(4-Amino-furazan-3-yl)-1-ethyl-1H-imidazo[4,5-c]pyridin-6-yl]oxy}phenyl)-1-butanesulfonamide;

N-[(3-{[2-(4-Amino-furazan-3-yl)-1-phenyl-1H-imidazo[4,5-c]pyridin-6-yl]oxy}phenyl)carbonyl]-beta-alanine;

4-{1-Ethyl-6-[(3-{[3-(4-morpholinyl)propyl]oxy}phenyl)oxy]-1H-imidazo[4,5-c]pyridin-2-yl}-furazan-3-amine;

1,1-Dimethylethyl (3-{[2-(4-amino-furazan-3-yl)-1-ethyl-1H-imidazo[4,5-c]pyridin-6-yl]oxy}phenyl)carbamate;

3-({2-(4-Amino-furazan-3-yl)-1-[4-(trifluoromethyl)phenyl]-1H-imidazo[4,5-c]pyridin-6-yl}oxy)-N-[2-(4-morpholinyl)ethyl]benzamide;

3-{[2-(4-Amino-furazan-3-yl)-1-phenyl-1H-imidazo[4,5-c]pyridin-6-yl]oxy}-N-[3-(dimethylamino)phenyl]benzamide;

1-(3-{[2-(4-Amino-furazan-3-yl)-1-ethyl-1H-imidazo[4,5-c]pyridin-6-yl]oxy}phenyl)-2-methyl-4-(4-morpholinyl)-1-butanone;

1-(3-{[2-(4-Amino-furazan-3-yl)-1-ethyl-1H-imidazo[4,5-c]pyridin-6-yl]oxy}phenyl)-1-propanone;

1-(3-{[2-(4-Amino-furazan-3-yl)-1-ethyl-1H-imidazo[4,5-c]pyridin-6-yl]oxy}phenyl)ethanol;

4-[6-[(4-Fluorophenyl)oxy]-1-(2-methyl-1,2,3,4-tetrahydro-7-isoquinolinyl)-1H-imidazo[4,5-c]pyridin-2-yl]-furazan-3-amine;

2-(3-{[2-(4-Amino-furazan-3-yl)-1-ethyl-1H-imidazo[4,5-c]pyridin-6-yl]oxy}phenyl)-2-butanol;

3-{[2-(4-Amino-furazan-3-yl)-1-(6-methyl-2-pyridinyl)-1H-imidazo[4,5-c]pyridin-6-yl]oxy}-N-[3-(2-oxo-1-pyrrolidinyl)propyl]benzamide;

4-{6-[(3-Aminophenyl)oxy]-1-phenyl-1H-imidazo[4,5-c]pyridin-2-yl}-furazan-3-amine;

3-{[2-(4-Amino-furazan-3-yl)-1-ethyl-1H-imidazo[4,5-c]pyridin-6-yl]oxy}-N-methyl-N-[3-(1-methyl-4-piperidinyl)propyl]benzamide;

3-{[2-(4-Amino-furazan-3-yl)-1-phenyl-1H-imidazo[4,5-c]pyridin-6-yl]oxy}-N-{2-[3,5-bis(methyloxy)phenyl]ethyl}benzamide;

N-(3-{[2-(4-Amino-furazan-3-yl)-1-phenyl-1H-imidazo[4,5-c]pyridin-6-yl]oxy}phenyl)-4-(dimethylamino)benzamide;

4-(1-(4-{[2-(Dimethylamino)ethyl]oxy}phenyl)-6-{[3-(methylsulfonyl)phenyl]oxy}-1H-imidazo[4,5-c]pyridin-2-yl)-furazan-3-amine;

4-(1-Ethyl-6-{[3-(methyloxy)phenyl]oxy}-1H-imidazo[4,5-c]pyridin-2-yl)-furazan-3-amine;

3-{[2-(4-Amino-furazan-3-yl)-1-(6-methyl-2-pyridinyl)-1H-imidazo[4,5-c]pyridin-6-yl]oxy}-N-[2-(4-morpholinyl)ethyl]benzamide;

4-[1-Ethyl-6-({3-[3-(4-methyl-1-piperazinyl)-3-oxopropyl]phenyl}oxy)-1H-imidazo[4,5-c]pyridin-2-yl]-furazan-3-amine;

N-(3-{[2-(4-Amino-furazan-3-yl)-1-ethyl-1H-imidazo[4,5-c]pyridin-6-yl]oxy}phenyl)-4-(methyloxy)-3-(trifluoromethyl)benzamide;

N-(3-{[2-(4-Amino-furazan-3-yl)-1-phenyl-1H-imidazo[4,5-c]pyridin-6-yl]oxy}phenyl)-4-(methyloxy)benzamide;

N-(3-{[2-(4-Amino-furazan-3-yl)-1-ethyl-1H-imidazo[4,5-c]pyridin-6-yl]oxy}phenyl)-4-methylbenzenesulfonamide;

Methyl (3-{[2-(4-amino-furazan-3-yl)-1-ethyl-1H-imidazo[4,5-c]pyridin-6-yl]oxy}phenyl)acetate;

N-(5-{[2-(4-Amino-furazan-3-yl)-1-ethyl-1H-imidazo[4,5-c]pyridin-6-yl]oxy}-2-methylphenyl)acetamide;

1-{3-[(3-{[2-(4-Amino-furazan-3-yl)-1-ethyl-1H-imidazo[4,5-c]pyridin-6-yl]oxy}phenyl)oxy]propyl}-2-pyrrolidinone;

(3-{[2-(4-Amino-furazan-3-yl)-1-ethyl-1H-imidazo[4,5-c]pyridin-6-yl]oxy}phenyl)acetic acid;

N-(4-{[2-(4-Amino-furazan-3-yl)-1-ethyl-1H-imidazo[4,5-c]pyridin-6-yl]thio}phenyl)acetamide;

N-(3-{[2-(4-Amino-furazan-3-yl)-1-ethyl-1H-imidazo[4,5-c]pyridin-6-yl]oxy}phenyl)-4-fluorobenzenesulfonamide;

1-(3-{[2-(4-Amino-furazan-3-yl)-1-phenyl-1H-imidazo[4,5-c]pyridin-6-yl]oxy}phenyl)ethanone;

4-{2-(4-Amino-furazan-3-yl)-6-[(3-aminophenyl)oxy]-1H-imidazo[4,5-c]pyridin 1-yl}phenyl 2-methylpropanoate;

3-{[2-(4-Amino-furazan-3-yl)-1-ethyl-1H-imidazo[4,5-c]pyridin-6-yl]oxy}benzonitrile;

N-(3-{[2-(4-Amino-furazan-3-yl)-1-ethyl-1H-imidazo[4,5-c]pyridin-6-yl]oxy}phenyl)-3-methylbutanamide;

4-({[(3-{[2-(4-Amino-furazan-3-yl)-1-ethyl-1H-imidazo[4,5-c]pyridin-6-yl]oxy}phenyl)amino]carbonyl}amino)benzoic acid;

4-{6-[(4-Aminophenyl)oxy]-1-phenyl-1H-imidazo[4,5-c]pyridin-2-yl}-furazan-3-amine;

4-{1-Ethyl-6-[(3-{[2-(4-morpholinyl)ethyl]oxy}phenyl)oxy]-1H-imidazo[4,5-c]pyridin-2-yl}-furazan-3-amine;

3-({2-(4-Amino-furazan-3-yl)-1-[2-(4-morpholinyl)ethyl]-1H-imidazo[4,5-c]pyridin-6-yl}oxy)-N-[3-(4-methyl-1-piperazinyl)propyl]benzamide;

3-{[2-(4-Amino-furazan-3-yl)-1-(2-methyl-4-pyridinyl)-1H-imidazo[4,5-c]pyridin-6-yl]oxy}-N-[2-(4-morpholinyl)ethyl]benzamide;

3-({2-(4-Amino-furazan-3-yl)-1-[4-(trifluoromethyl)phenyl]-1H-imidazo[4,5-c]pyridin-6-yl}oxy)-N-[3-(2-oxo-1-pyrrolidinyl)propyl]benzamide;

Methyl 3-{[2-(4-amino-furazan-3-yl)-1-(4-piperidinyl)-1H-imidazo[4,5-c]pyridin-6-yl]oxy}benzoate;

N-(3-{[2-(4-Amino-furazan-3-yl)-1-ethyl-1H-imidazo[4,5-c]pyridin-6-yl]oxy}phenyl)-N-methylacetamide;

N-(4-{2-(4-Amino-furazan-3-yl)-6-[(4-fluorophenyl)oxy]-1H-imidazo[4,5-c]pyridin-1-yl}phenyl)methanesulfonamide;

Methyl 3-{[2-(4-amino-furazan-3-yl)-1-phenyl-1H-imidazo[4,5-c]pyridin-6-yl]oxy}benzoate;

3-{[2-(4-Amino-furazan-3-yl)-1-phenyl-1H-imidazo[4,5-c]pyridin-6-yl]oxy}-N-[2-(phenyloxy)ethyl]benzamide;

N-(3-{[2-(4-Amino-furazan-3-yl)-1-ethyl-1H-imidazo[4,5-c]pyridin-6-yl]oxy}-2-methylphenyl)acetamide;

3-{[2-(4-Amino-furazan-3-yl)-1-phenyl-1H-imidazo[4,5-c]pyridin-6-yl]oxy}-N-[3-(dimethylamino)propyl]-N-methylbenzamide;

3-{[2-(4-Amino-furazan-3-yl)-1-(phenylmethyl)-1H-imidazo[4,5-c]pyridin-6-yl]oxy}-N-[2-(4-morpholinyl)ethyl]benzamide;

3-{[2-(4-Amino-furazan-3-yl)-1-phenyl-1H-imidazo[4,5-c]pyridin-6-yl]oxy}-N-[2-(4-morpholinyl)ethyl]benzenesulfonamide;

4-{2-(4-Amino-furazan-3-yl)-6-[(4-fluorophenyl)oxy]-1H-imidazo[4,5-c]pyridin-1-yl}-2-chlorophenol;

4-{[2-(4-Amino-furazan-3-yl)-1-ethyl-1H-imidazo[4,5-c]pyridin-6-yl]oxy}benzonitrile;

4-(1-Ethyl-7-{[3-(methyloxy)phenyl]oxy}-1H-imidazo[4,5-c]pyridin-2-yl)-furazan-3-amine;

3-{[2-(4-Amino-furazan-3-yl)-1-phenyl-1H-imidazo[4,5-c]pyridin-6-yl]oxy}benzoic acid;

4-{6-[(3,4-Dimethylphenyl)oxy]-1-ethyl-1H-imidazo[4,5-c]pyridin-2-yl}-furazan-3-amine;

4-{1-[2-(Aminoacetyl)-1,2,3,4-tetrahydro-7-isoquinolinyl]-6-[(4-fluorophenyl)oxy]-1H-imidazo[4,5-c]pyridin-2-yl}-furazan-3-amine;

4-(1-Ethyl-6-{[3-(1,3-thiazol-5-yl)phenyl]oxy}-1H-imidazo[4,5-c]pyridin-2-yl)-furazan-3-amine;

4-(1-Ethyl-6-{[3-(1H-imidazol-1-yl)phenyl]oxy}-1H-imidazo[4,5-c]pyridin-2-yl)-furazan-3-amine;

4-(1-Ethyl-6-{[3-(1,3-oxazol-5-yl)phenyl]oxy}-1H-imidazo[4,5-c]pyridin-2-yl)-furazan-3-amine;

4-(1-Ethyl-6-{[3-(4-morpholinyl)phenyl]oxy}-1H-imidazo[4,5-c]pyridin-2-yl)-furazan-3-amine;

4-(1-Phenyl-6-{[3-(1-piperidinylcarbonyl)phenyl]oxy}-1H-imidazo[4,5-c]pyridin-2-yl)-furazan-3-amine;

4-(6-{[3-(Dimethylamino)phenyl]oxy}-1-ethyl-1H-imidazo[4,5-c]pyridin-2-yl)-furazan-3-amine;

3-{[2-(4-Amino-furazan-3-yl)-1-phenyl-1H-imidazo[4,5-c]pyridin-6-yl]oxy}-N,N-dimethylbenzamide;

N-(4-{[2-(4-Amino-furazan-3-yl)-1-phenyl-1H-imidazo[4,5-c]pyridin-6-yl]oxy}phenyl)acetamide;

Methyl 3-{[2-(4-amino-furazan-3-yl)-1-(1,3-benzodioxol-5-yl)-1H-imidazo[4,5-c]pyridin-6-yl]oxy}benzoate;

5-{[2-(4-Amino-furazan-3-yl)-1-ethyl-1H-imidazo[4,5-c]pyridin-6-yl]oxy}-1,3-dimethyl-1,3-dihydro-2H-benzimidazol-2-one;

3-{[2-(4-Amino-furazan-3-yl)-1-phenyl-1H-imidazo[4,5-c]pyridin-6-yl]oxy}-N-[3-(ethyloxy)propyl]benzamide;

2-[7-{2-(4-Amino-furazan-3-yl)-6-[(4-fluorophenyl)oxy]-1H-imidazo[4,5-c]pyridin-1-yl}-3,4-dihydro-2(1H)-isoquinolinyl]acetamide;

Methyl 3-{[2-(4-amino-furazan-3-yl)-1-(4-bromophenyl)-1H-imidazo[4,5-c]pyridin-6-yl]oxy}benzoate;

6-{[2-(4-Amino-furazan-3-yl)-1-ethyl-1H-imidazo[4,5-c]pyridin-6-yl]oxy}-3,4-dihydro-1(2H)-naphthalenone;

4-[6-(1H-Benzimidazol-5-yloxy)-1-ethyl-1H-imidazo[4,5-c]pyridin-2-yl]-furazan-3-amine;

4-(1-Ethyl-6-{[3-(1-methylethyl)phenyl]oxy}-1H-imidazo[4,5-c]pyridin-2-yl)-furazan-3-anine;

4-{1-(3-Chloro-4-{[2-(dimethylamino)ethyl]oxy}phenyl)-6-[(4-fluorophenyl)oxy]-1H-imidazo[4,5-c]pyridin-2-yl}-furazan-3-amine;

4-{6-[(4-Fluorophenyl)oxy]-1-phenyl-1H-imidazo[4,5-c]pyridin-2-yl}-furazan-3-amine;

Methyl 4-{[2-(4-amino-furazan-3-yl)-1-ethyl-1H-imidazo[4,5-c]pyridin-6-yl]oxy}benzoate;

4-{6-[(3-Nitrophenyl)oxy]-1-phenyl-1H-imidazo[4,5-c]pyridin-2-yl}-furazan-3-amine;

3-({2-(4-Amino-furazan-3-yl)-1-[2-(4-morpholinyl)ethyl]-1H-imidazo[4,5-c]pyridin-6-yl}oxy)-N-[3-(2-oxo-1-pyrrolidinyl)propyl]benzamide;

3-({2-(4-Amino-furazan-3-yl)-1-[2-(dimethylamino)ethyl]-1H-imidazo[4,5-c]pyridin-6-yl}oxy)-N-[3-(2-oxo-1-pyrrolidinyl)propyl]benzamide;

3-{[2-(4-Amino-furazan-3-yl)-1-(phenylmethyl)-1H-imidazo[4,5-c]pyridin-6-yl]oxy}benzoic acid;

Methyl 3-{[2-(4-amino-furazan-3-yl)-1-(phenylmethyl)-1H-imidazo[4,5-c]pyridin-6-yl]oxy}benzoate;

7-{[2-(4-Amino-furazan-3-yl)-1-ethyl-1H-imidazo[4,5-c]pyridin-6-yl]oxy}-4-methyl-2(1H)-quinolinone;

4-{2-(4-Amino-furazan-3-yl)-6-[(3-aminophenyl)oxy]-1H-imidazo[4,5-c]pyridin-1-yl}phenyl 4-(methyloxy)benzoate;

3-({2-(4-Amino-furazan-3-yl)-1-[2-(4-morpholinyl)ethyl]-1H-imidazo[4,5-c]pyridin-6-yl}oxy)benzoic acid;

Methyl 3-{[2-(4-amino-furazan-3-yl)-1-(2-methyl-1,3-benzoxazol-5-yl)-1H-imidazo[4,5-c]pyridin-6-yl]oxy}benzoate;

3-{[2-(4-Amino-furazan-3-yl)-1-phenyl-1H-imidazo[4,5-c]pyridin-6-yl]oxy}-N-[2-(4-morpholinyl)ethyl]benzamide;

3-{[2-(4-Amino-furazan-3-yl)-1-phenyl-1H-imidazo[4,5-c]pyridin-6-yl]oxy}-N-[2-(4-morpholinyl)ethyl]benzamide;

4-{1-Ethyl-6-[(3-{[2-(1-methyl-3-piperidinyl)ethyl]oxy}phenyl)oxy]-1H-imidazo[4,5-c]pyridin-2-yl}-furazan-3-amine;

4-[1-Ethyl-6-({3-[4-(1-methyl-4-piperidinyl)butyl]phenyl}oxy)-1H-imidazo[4,5-c]pyridin-2-yl]-furazan-3-amine;

1-(3-{[2-(4-Amino-furazan-3-yl)-1-(1,2,3,4-tetrahydro-7-isoquinolinyl)-1H-imidazo[4,5-c]pyridin-6-yl]oxy}phenyl)ethanone;

Inhibitors of ROCKs have been suggested for use in the treatments of a variety of diseases. They include cardiovascular diseases such as hypertension, chronic and congestive heart failure, ischemic angina, cardiac hypertrophy and fibrosis, restenosis, chronic renal failure and atherosclerosis. In addition, because of its muscle relaxing properties, it is also suitable for asthma, male erectile dysfunctions, female sexual dysfunction and over-active bladder syndrome. ROCK inhibitors have been shown to possess anti-inflammatory properties. Thus they can be used as treatment for neuroinflammatory diseases such as stroke, multiple sclerosis, Alzheimer's disease, Parkinson's disease, amyotrophic lateral sclerosis and inflammatory pain, as well as other inflammatory diseases such as rheumatoid arthritis, irritable bowel syndrome, inflammatory bowel disease, and Crohn's diseases. In addition, based on their neurite outgrowth inducing effects, ROCK inhibitors could be useful drugs for neuronal regeneration, inducing new axonal growth and axonal rewiring across lesions within the CNS. ROCK inhibitors are therefore likely to be useful for regenerative (recovery) treatment of CNS disorders such as spinal cord injury, acute neuronal injury (stroke, traumatic brain injury), Parkinsons disease, Alzheimers disease and other neurodegenerative disorders. Since ROCK inhibitors reduce cell proliferation and cell migration, they could be useful in treating cancer and tumor metastasis. Further more, there is evidence suggesting that ROCK inhibitors suppress cytoskeletal rearrangement upon virus invasion, thus they also have potential therapeutic value in anti-viral and anti-bacterial applications. ROCK inhibitors are also useful for the treatment of insulin resistance and diabetes.

Preferably ROCK inhibitors are useful for the treatment of hypertension, chronic and congestive heart failure, ischemic angina, asthma, male erectile dysfunction, female sexual dysfunction, stroke, inflammatory bowel diseases, spinal cord injury, glaucoma and tumor metastasis.

More preferably ROCK inhibitors are useful for the treatment of hypertension, chronic and congestive heart failure and ischemic angina.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the term "optionally" means that the subsequently described event(s) may or may not occur, and includes both event(s), which occur, and events that do not occur.

As used herein, the term "physiologically functional derivative" refers to any pharmaceutically acceptable derivative of a compound of the present invention, for example, an ester or an amide, which upon administration to a mammal is capable of providing (directly or indirectly) a compound of the present invention or an active metabolite thereof. Such derivatives are clear to those skilled in the art, without undue experimentation, and with reference to the teaching of Burger's Medicinal Chemistry And Drug Discovery, 5$^{th}$ Edition, Vol 1: Principles and Practice, which is incorporated herein by reference to the extent that it teaches physiologically functional derivatives.

As used herein, the term "solvate" refers to a complex of variable stoichiometry formed by a solute (in this invention, a compound of formula (I) or a salt or physiologically functional derivative thereof) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water.

As used herein, the term "substituted" refers to substitution with the named substituent or substituents, multiple degrees of substitution being allowed unless otherwise stated.

Certain of the compounds described herein may contain one or more chiral atoms, or may otherwise be capable of existing as two enantiomers. The compounds of this invention include mixtures of enantiomers as well as purified enantiomers or enantiomerically enriched mixtures. Also included within the scope of the invention are the individual isomers of the compounds represented by formula (I) above as well as any wholly or partially equilibrated mixtures thereof. The present invention also covers the individual isomers of the compounds represented by the formulas above as mixtures with isomers thereof in which one or more chiral centers are inverted. Also, it is understood that any tautomers and mixtures of tautomers of the compounds of formula (I) are included within the scope of the compounds of formula (I).

Typically, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts derived from a nitrogen on a substituent in the compound of formula (I). Representative salts include the following salts: acetate, benzenesulfonate, benzoate, bicarbonate, bisulfate, bitartrate, borate, bromide, calcium edetate, camsylate, carbonate, chloride, clavalanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate, triethiodide, trimethylammonium and valerate. Other salts, which are not pharmaceutically acceptable, may be useful in the preparation of compounds of this invention and these form a further aspect of the invention.

While it is possible that, for use in therapy, therapeutically effective amounts of a compound of formula (I), as well as salts, solvates and physiological functional derivatives thereof, may be administered as the raw chemical, it is possible to present the active ingredient as a pharmaceutical composition. Accordingly, the invention further provides pharmaceutical compositions, which include therapeutically effective amounts of compounds of the formula (I) and salts, solvates and physiological functional derivatives thereof, and one or more pharmaceutically acceptable carriers, diluents, or excipients. The compounds of the formula (I) and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula (I), or salts, solvates and physiological functional derivatives thereof, with one or more pharmaceutically acceptable carriers, diluents or excipients.

Pharmaceutical formulations may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the formula (I), depending on the condition being treated, the route of administration and the age, weight and condition of the patient, or pharmaceutical formulations may be presented in unit dose forms containing a predetermined amount of active ingredient per unit dose. Preferred unit dosage formulations are those containing a daily dose or sub-dose, as herein above recited, or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of formula (I), and salts, solvates and physiological functional derivatives thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of formula (I) and salts, solvates and physiological functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered, dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the formulations may include other agents conventional in the art having regard to the type of formulation in question, for example those suitable for oral administration may include flavouring agents.

A therapeutically effective amount of a compound of the present invention will depend upon a number of factors including, for example, the age and weight of the human or other animal, the precise condition requiring treatment and its severity, the nature of the formulation, and the route of administration, and will ultimately be at the discretion of the attendant physician or veterinarian. However, an effective amount of a compound of formula (I) for the treatment of neoplastic growth, for example colon or breast carcinoma, will generally be in the range of 0.1 to 100 mg/kg body weight of recipient (mammal) per day and more usually in the range of 1 to 10 mg/kg body weight per day. Thus, for a 70 kg adult mammal, the actual amount per day would usually be from 70 to 700 mg and this amount may be given in a single dose per day or more usually in a number (such as two, three, four, five or six) of sub-doses per day such that the total daily dose is the same. An effective amount of a salt or solvate, or physiologically functional derivative thereof, may be determined as a proportion of the effective amount of the compound of formula (I) per se. It is envisaged that similar dosages would be appropriate for treatment of the other conditions referred to above.

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the Working Examples.

Compounds of general formula (I) may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) *Protecting Groups in Organic Synthesis*, John Wiley & Sons). These groups are removed at a convenient stage of the compound synthesis using methods that are readily apparent to those skilled in the art. The selection of processes as well as the reaction conditions and order of their execution shall be consistent with the preparation of compounds of Formula (I).

Compounds with the general structure 8 can be prepared according to the procedure described in Scheme 1. Treatment of an appropriately substituted pyridine derivative 1 with potassium t-butoxide and t-butyl hydroperoxide provides the pyridone 2 which can be chlorinated and the resulting dichloride treated with an amine to give the aminopyridine 3. Displacement of the second chloride with a sodium salt of an alcohol (or phenol) or thiol (or thiophenol), followed by reduction provides structure 5, which can then be coupled to cyanoacetic acid with a variety of coupling agents to provide the corresponding cyanoacetamide 5a. This amide can then be dehydrated with glacial acetic acid to give the azabenzimidazole 6. Alternatively, the diamine 5 can be heated with ethyl cyanoacetate to provide 6 directly. The nitrile 6 can be transformed into the oxime 7 by treatment with nitrous acid and then further elaborated to the aminofurazan structure 8 by treatment with hydroxylamine and base either in one step or in a two step process where the intermediate 7a is isolated.

Scheme 1.

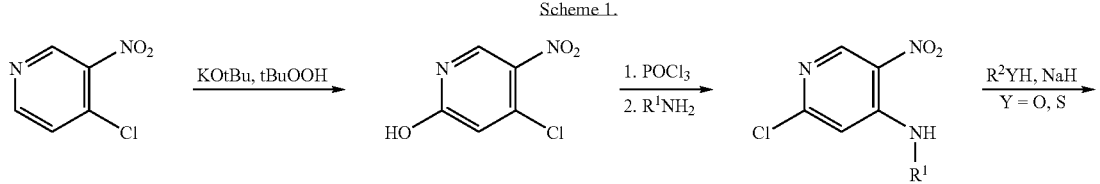

-continued
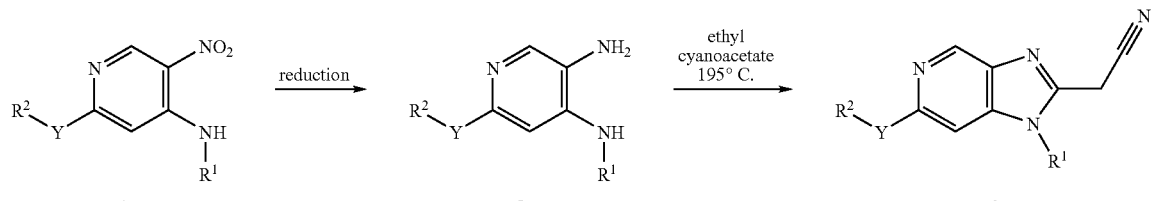
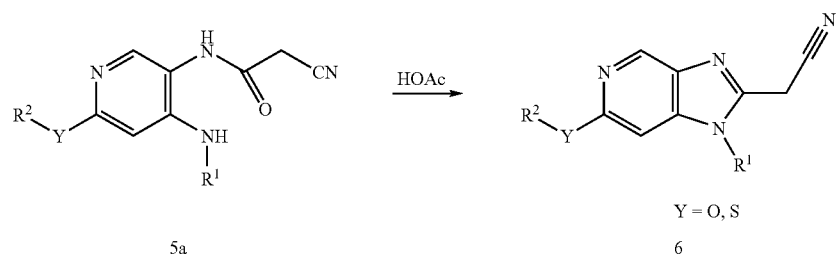
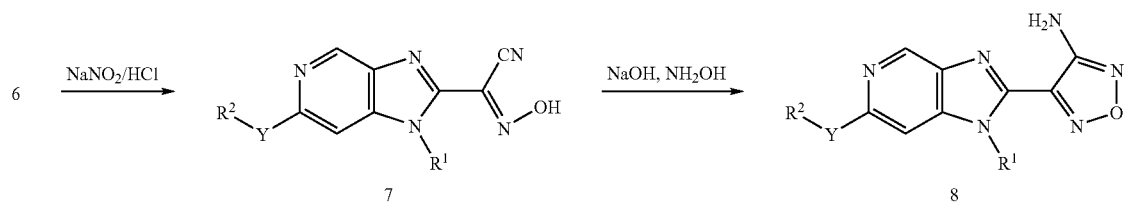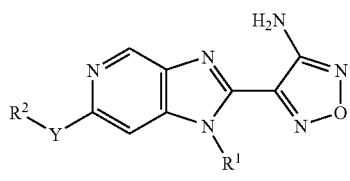
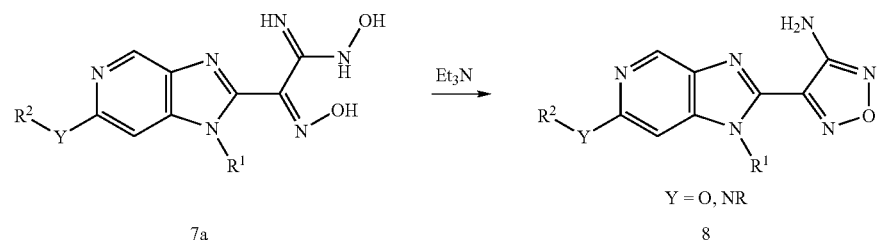

One can further manipulate appropriately substituted compounds 8, an example of which is shown in Scheme 2. The methyl ether 6b is cleaved with boron tribromide to provide the phenol 9, which may be alkylated under a variety of conditions to provide the ethers 10.

Scheme 2.

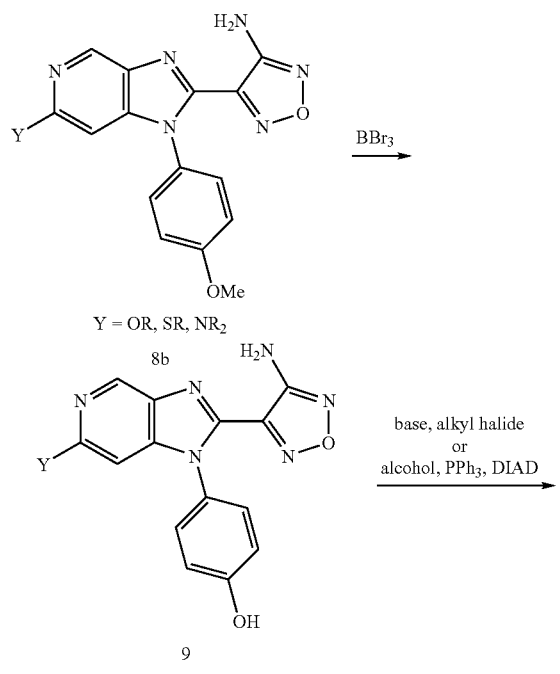

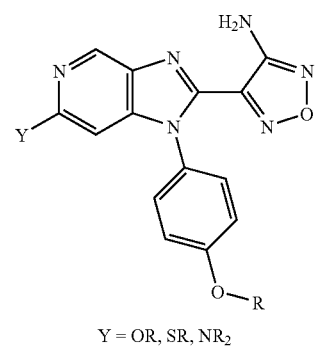

Y = OR, SR, NR$_2$

10

Compounds of the general structure 17 can be formed according to Scheme 3. Oxidation of 4-methoxy-3-nitro pyridine (11) with t-butyl hydroperoxide and potassium t-butoxide followed by bromination provides 2,4-dibromo-5-nitropyridine (12) which can be reacted with an amine to provide structure 13. Reduction, followed by imidazole formation and aminofurazan formation, analogous to Scheme 1 above, provides the bromides 17.

Scheme 3.

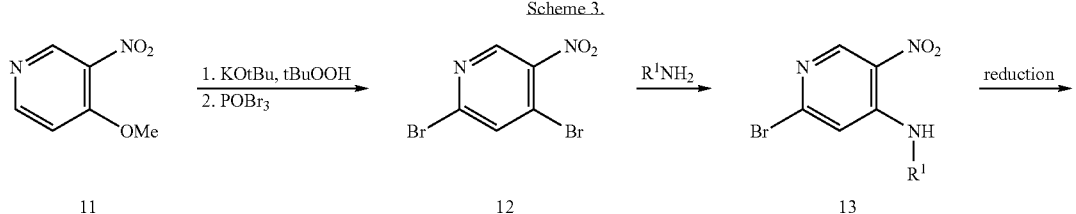

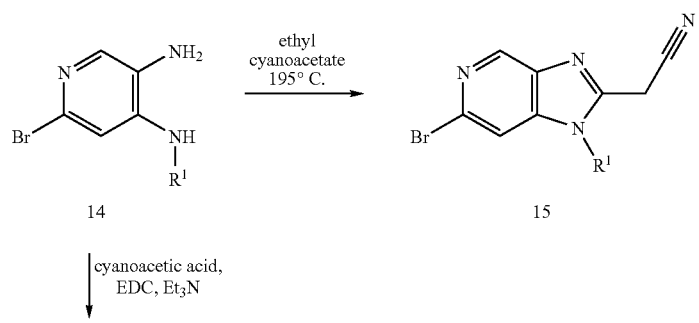

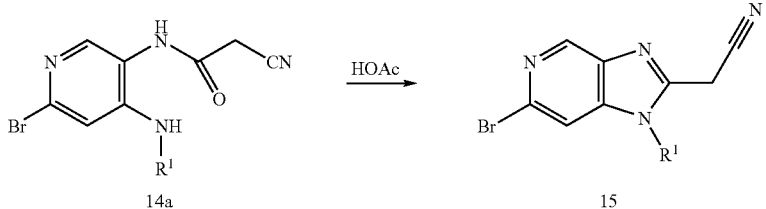

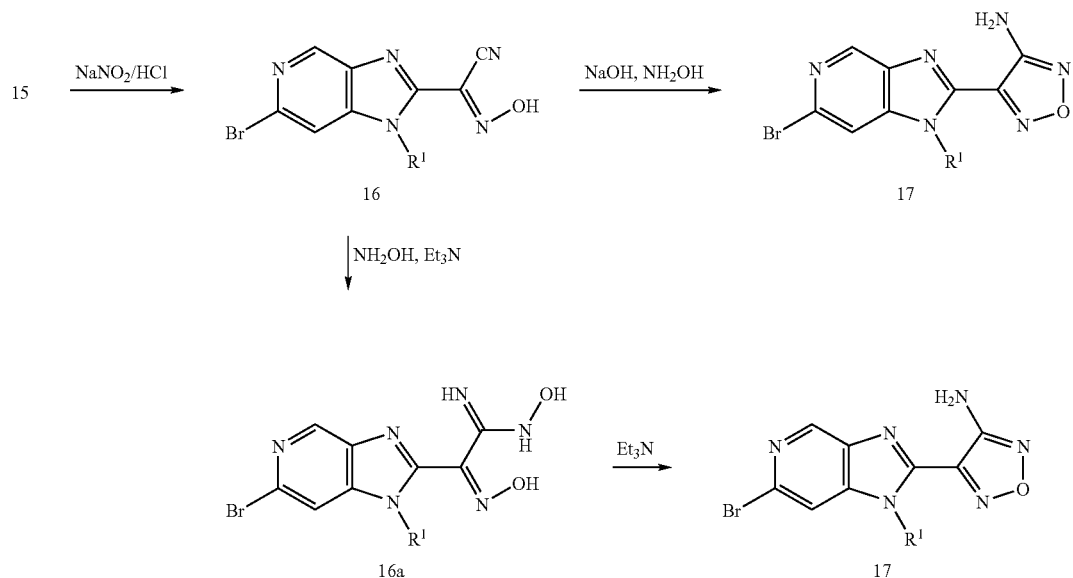

The bromide 17 can then be transformed into a number of groups as shown in Scheme 4. Alkylamines such as 18 can be formed by treatment with a copper salt and base, whereas aliphatic amines such as 19 can be formed by a palladium-catalyzed amination. Aliphatic and aromatic thiols such as 20 can also be formed under palladium catalysis. Phenolic compounds such as 21 can be formed by treating structures 17 and a phenol with a copper salt, base and a ligand. Related analogs with a carbon tether can be prepared from bromide 17 and the appropriate organozinc reagent in the presence of a palladium catalyst.

Scheme 4.

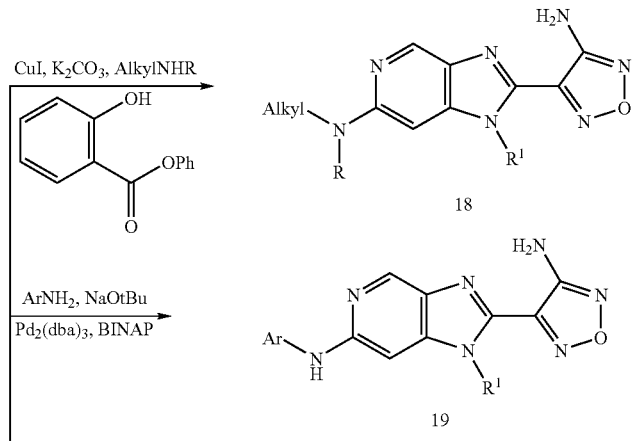

-continued

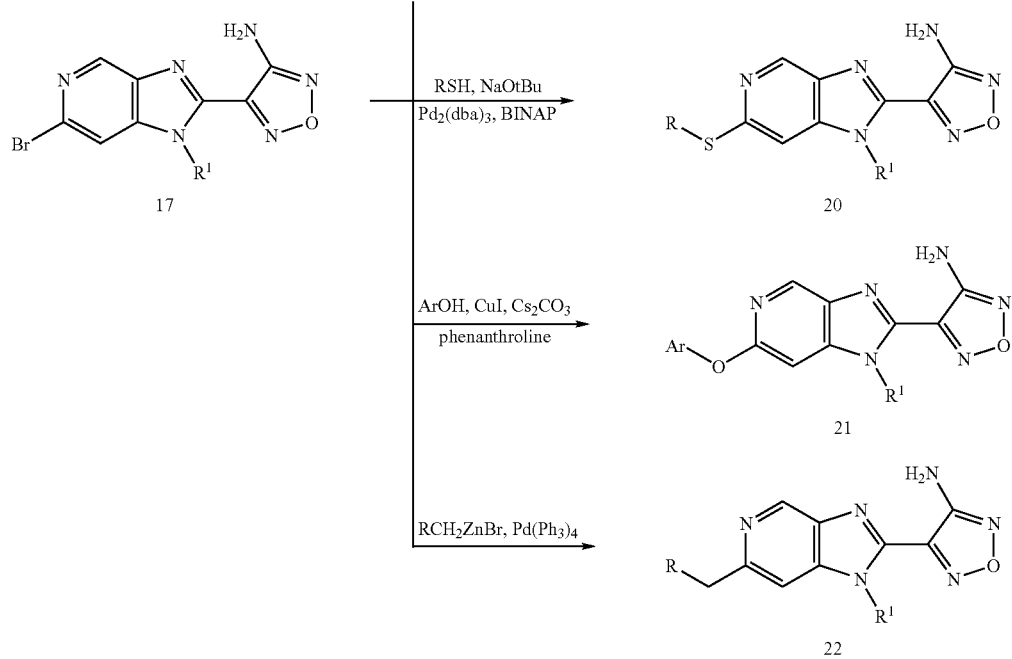

EXAMPLES

The following examples are intended to be illustrative only and not limiting in any way:

Example 1

N-(3-{[2-(4-amino-furazan-3-yl)-1-phenyl-1H-imidazo[4,5-c]pyridin-6-yl]oxy}phenyl)acetamide

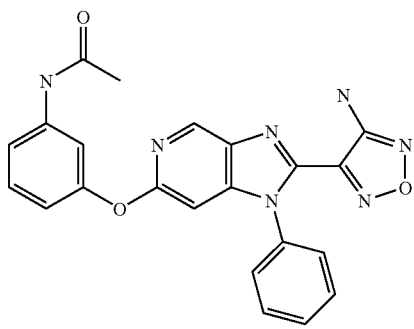

Step 1. 4-Chloro-3-nitropyridine

To a suspension of 3-nitro-4-pyridinol (20 g, 143 mmol) in toluene (300 mL) was added phosphorous oxychloride (65.7 g, 429 mmol) at 0° C. The resulting mixture was warmed to room temperature, then heated to reflux (110° C.) for 16 hours. After cooling to rt, the solvent was removed in vacuo and the residue was poured on ice, then basified with $K_2CO_3$ to pH≈10. The mixture was extracted with ethyl acetate and the organic phase was washed twice with water, followed by once with brine before concentrating to a brown oil which solidified on standing (22.5 g, 99%). MS (ES+) m/e 159 [M+H]$^+$.

Step 2. 4-Chloro-2-hydroxy-5-nitropyridine

THF (500 mL) was cooled to −78° C. and anhydrous $NH_3$ (~200 mL) was condensed into the THF. Potassium t-butoxide (71.0 g, 630 mmol) was added and the mixture was allowed to warm to ~−35° C. The product from Step 1 (40.0 g, 250 mmol) was cooled to 0° C. in THF (200 mL) and a solution of t-BuOOH (5 M in decane, 50 mL, 250 mmol) was added over 5 min. This solution was then added dropwise to the KOt-Bu solution prepared above over 1 h, then stirred for 2 h at −35° C. and then carefully quenched with ~50 mL of sat. $NH_4Cl$ solution. The mixture was allowed to vent and warm to rt overnight, then the organics were concentrated and the residue made acidic with $NH_4Cl$ solution and filtered. The solid was washed with cold $H_2O$ and dried to give the title compound as a dark brown solid (35 g, 80%).

Step 3. 2,4-Dichloro-5-nitropyridine

The product from Step 2 (40.0 g, 229 mmol) was suspended in toluene (300 mL) and $POCl_3$ (65 mL, 697 mmol) was added over 10 min, then the mixture was heated to relux for 6 h then cooled to 60° C. and allowed to stir overnight at that temperature. The heterogeneous mixture was cooled and concentrated, the residue was carefully made basic with aq. $K_2CO_3$ solution and extracted with EtOAc. The organic layers were combined, washed with $H_2O$ and brine, dried ($Na_2SO_4$), filtered and the filtrate was concentrated to give an oil. The crude oil was passed through a plug of silica gel (50%

EtOAc in hexanes) to give the title compound (32.5 g, 74%) as an orange oil which solidified on standing. MS (ES+) m/e 194 [M+H]+.

Step 4. 2-Chloro-5-nitro-N-phenyl-4-pyridineamine

The product of Step 3 (66.5 g, 345 mmol) in THF (400 mL) and triethylamine (50.3 mL, 361 mmol) was added, followed by aniline (31.4 mL, 345 mmol) and the reaction mixture was allowed to stir at rt for 18 hours. Water (1.2 L) was added dropwise to the yellow solution and the precipitate formed was filtered, washed with H2O and Et2O to give the title compounds as yellow crystals (42.8 g). The filtrate was concentrated to roughly ½ volume and the resulting solid was filtered and washed with H2O and Et2O to give addition title compound (18.1 g, 60.9 g total, 71%). $^1$H NMR (400 MHz, CDCl3) δ ppm 9.68 (s, 1H), 9.13 (s, 1H), 7.54 (t, 2H, 7.3 Hz), 7.42 (t, 1H, 7.3 Hz), 7.31 (d, 2H, 7.3 Hz), 6.94 (s, 1H). MS (ES+) m/e 250 [M+H]+.

Step 5. N-(3-{[5-Nitro-4-(phenylamino)-2-pyridinyl]oxy}phenyl)acetamide

Sodium hydride (60% dispersion in oil, 16.24 g, 406 mmol) was suspended in DMF (800 mL) and solid N-(3-hydroxyphenyl)acetamide (61.0 g, 406 mol) was added portionwise over 1 h (warming and frothing occurs). After the final addition the product from Step 4 (101.2 g, 406 mmol) was added as a solid, portionwise, over 10 min and the resulting mixture was heated to 60° C. overnight. Water (800 mL) was carefully added dropwise to the still warm reaction mixture over 1 h to give a fine yellow precipitate. The mixture was then cooled to 0° C., filtered and the resulting solid was washed with cold H2O and hexane to give the title compound (143.3 g, 97%) as a yellow solid. $^1$H NMR (400 MHz, DMSO-D6) δ ppm 10.06 (s, 1H), 9.80 (s, 1H), 8.91 (s, 1H), 7.44-7.49 (m, 3H), 7.37 (dd, 2H, 1.26 Hz, 8.6 Hz), 7.29-7.33 (m, 3H), 6.76-6.80 (m, 1H), 6.22 (s, 1H), 2.04 (s, 3H). MS (ES+) m/e 365 [M+H]+.

Step 6. N-(3-{[5-Amino-4-(phenylamino)-2-pyridinyl]oxy}phenyl)acetamide

The product of Step 5 (37.7 g, 103.5 mmol) in MeOH (350 mL) and dichloromethane (350 mL) was hydrogenated for overnight with a balloon of hydrogen gas in the presence of 10% palladium on carbon (3.5 g). After filtration of the catalyst through a pad of Celite, the filtrate was concentrated in vacuo to afford the title compound as a crude foam (~35 g, quantitative). $^1$H NMR (400 MHz, MeOD) δ ppm 7.56 (s, 1H), 7.39-7.40 (m, 1H), 7.19-7.34 (m, 5H), 7.07-7.11 (m, 1H), 6.73 (dt, 1H, 1.8 Hz, 7.1 Hz), 6.48 (s, 1H), 3.32-3.34 (m, 3H), 2.12 (s, 3H). MS (ES+) m/e 335 [M+H]+.

Step 7. N-(3-{[2-(Cyanomethyl)-1-phenyl-1H-imidazo[4,5-c]pyridin-6-yl]oxy}phenyl)acetamide The product from Step 6 (29.4 g, 88 mmol), cyanoacetic acid (14.9 g, 176 mmol) and EDCI (33.7 g, 176 mmol) were suspended in CH2Cl2 (500 mL), Et3N (49 mL, 352 mmol) was added and the resulting solution was allowed to stir at rt overnight. The reaction mixture was poured into H2O and extracted with EtOAc. The organic extracts were combined, washed with H2O and brine, dried (MgSO4), filtered and the filtrate was concentrated to give a crude oil (~35 g) which was used without purification.

The crude amide from above (35 g, ~88 mmol) was heated to 100° C. for 2 h, then concentrated. The residue was made basic with sat. aq. K2CO3 and extracted with EtOAc. The organic extracts were combined, washed with H2O and brine, dried (MgSO4), filtered and the filtrate was concentrated to give a foam. The foam was triturated with MeOH to give the title compound as a light yellow solid (19.5 g). The mother liquors were combined, concentrate and purified by column chromatography (20%-100% EtOAc in hexane) to give an additional portion of the title compound (2.3 g, 21.8 g total, 65% over two steps). $^1$H NMR (400 MHz, MeOD) δ ppm 8.65 (d, 1H, 0.76 Hz), 7.65-7.69 (m, 31), 7.54-7.57 (m, 2H), 7.45-7.45 (m, 1H), 7.25-7.33 (m, 2H), 6.78-6.81 (m, 1H), 6.70 (d, 1H, 0.76 Hz), 2.11 (s, 3H), 1.31 (s, 2H). MS (ES+) m/e 384 [M+H]+.

Step 8. N-(3-{[2-(4-Amino-furazan-3-yl)-1-phenyl-1H-imidazo[4,5-c]pyridin-6-yl]oxy}phenyl)acetamide Sodium nitrite (1.9 g, 27.6 mmol) was added portionwise to a solution of the product from Step 7 (10.6 g, 27.6 mmol) in MeOH (150 mL) and 1.2 M aq. HCl (125 mL). After ~10 min a thick slurry formed and the mixture was allowed to stir for an additional 1 h, then the precipitate was filtered, washed with H2O and dried in vacuo to give the desired oxime (10.8 g, 95%) which was used directly in the next step.

The product from above (10.8 g, 26.2 mmol) was suspended in dioxane (100 mL) and Et3N (20 mL) and hydroxylamine (50% aq. soln., 1.7 mL, 26.2 mmol) was added and the mixture was heated to 110° C. for 48 h. The reaction mixture was cooled, concentrated, partitioned between 1M HCl and EtOAc and extracted with EtOAc. The organic extracts were combined, washed with H2O and brine, dried (MgSO4), filtered and the filtrate was concentrated to give a solid which was triturated with MeOH to give the title compound as a tan solid (4.5 g, 40%). $^1$H NMR (400 MHz, MeOD) δ ppm 8.84 (s, 1H), 7.65-7.67 (m, 3H), 7.54-7.56 (m, 2H), 7.49-7.50 (m, 1H), 7.30-7.36 (m, 2H), 6.83 (dt, 1H, 2.3 Hz, 7.8 Hz), 6.70 (d, 1H, 0.8 Hz), 2.64-2.65 (m, 3H), 2.12 (s, 3H). MS (ES+) m/e 428 [M+H]+.

Example 2

N-(3-{[1-{4-[(2-Aminoethyl)oxy]phenyl}-2-(4-amino-furazan-3-yl)-1H-imidazo[4,5-c]pyridin-6-yl]oxy}phenyl)acetamide

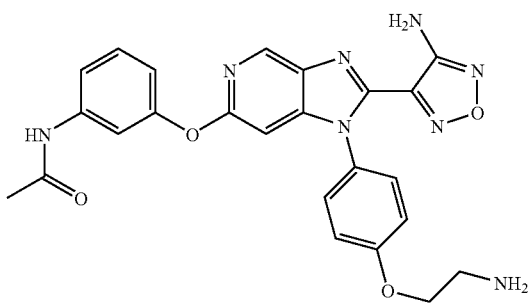

Step 1. 2-Chloro-N-(4-{[(1,1-dimethylethyl)(dimethyl)silyl]oxy}phenyl)-5-nitro-4-pyridineamine The product from Example 1, Step 3 (20.0 g, 104 mmol) and triethylamine (17.4 mL, 125 mmol) were dissolved in THF (200 mL) and a solution of 4-{[(1,1-dimethylethyl)(dimethyl)silyl]oxy}aniline (25.0 g, 113 mmol) in THF (50 mL) was added and the mixture was allowed to stir at rt overnight. The reaction mixture was poured into water and extracted with EtOAc. The combined organic phases were washed with brine, dried (MgSO4), filtered and the filtrate was concentrated to give the title compound (37.5 g, 95%) as a yellow oil. MS (ES+) m/e 381 [M+H]$^+$.

Step 2. N-[3-({4-[(4-Hydroxyphenyl)amino]-5-nitro-2-pyridinyl}oxy)phenyl]acetamide A solution of 3-acetamidophenol (10.8 g, 72 mmol) in DMF (50 mL) was added dropwise to a slurry of NaH (60% in oil, 2.88 g, 72 mmol) over 1 h. A solution of the product from Step 1 (13.7 g, 36.0 mmol) in DMF (50 mL) was added and the resulting mixture was heated to 60° C. overnight. The reaction mixture was poured into water and extracted with EtOAc. The organic layers were combined, washed with brine, dried (MgSO$_4$), filtered and the filtrate was concentrated to give an oil which was purified by chromatography (10-100% EtOAc in hexanes) to give the title compound (4.6 g, 34%) as an orange solid. MS (ES+) m/e 381 [M+H]$^+$.

Step 3. N-[3-({5-Amino-4-[(4-hydroxyphenyl)amino]-2-pyridinyl}oxy)phenyl]acetamide The product of Step 2 (2.9 g, 7.6 mmol) was hydrogenated in methanol (50 mL) in the presense of 5% Pd/C (250 mg) with a balloon of hydrogen overnight. The reaction mixture was filtered through Celite and concentrated to give the title compound (2.1 g, 79%) as a dark orange solid. MS (ES+) m/e 351 [M+H]$^+$.

Step 4. N-(3-{[2-(cyanomethyl)-1-(4-hydroxyphenyl)-2,3-dihydro-1H-imidazo[4,5-c]pyridin-6-yl]oxy}phenyl)acetamide The product from Step 3 (2.9 g, 8.3 mmol) and ethyl cyanoacetate (6 mL) were combined and heated to 195° C. in a sealed tube. The reaction mixture was cooled and the crude material was purified by chromatography (0-10% methanol in EtOAc) to give the title compound (2.6 g, 78%). MS (ES+) m/e 400 [M+H]$^+$.

Step 5. N-(3-{[2-(4-amino-furazan-3-yl)-1-(4-hydroxyphenyl)-1H-imidazo[4,5-c]pyridin-6-yl]oxy}phenyl)acetamide A solution of the product from Step 4 (2.6 g, 6.5 mmol) in methanol (30 mL), water (20 mL) and 6M HCl (8 mL) was treated with NaNO$_2$ (670 mg, 9.75 mmol) portionwise over 10 min then allowed to stir at rt for 1 h. The reaction mixture was poured into water and extracted with EtOAc. The organic phases were combined, washed with brine, dried (MgSO$_4$), filtered and the filtrate concentrated to give a dark solid which was suspended in dioxane (20 mL) and treated with triethylamine (3 mL) and NH$_2$OH (50% aqueous solution, 650 uL) and then heated to 90° C. for 2 h, then cooled to rt. The reaction mixture was poured into aq. NH$_4$Cl and extracted with EtOAc. The organic phases were combined, washed with brine, dried (MgSO$_4$), filtered and the filtrate concentrated to give a brown solid which was resuspended in dioxane (15 mL) and triethylamine (3 mL) and heated to 140° C. in a sealed tube for 3 h, then cooled to rt. The reaction mixture was poured into aq. NH$_4$Cl and extracted with EtOAc. The organic phases were combined, washed with brine, dried (MgSO$_4$), filtered and the filtrate concentrated to give the title compound (1.66 g, 57%) as a tan solid. MS (ES+) m/e 444 [M+H]$^+$.

Step 6. N-(3-{[1-{4-[(2-Aminoethyl)oxy]phenyl}-2-(4-amino-furazan-3-yl)-1H-imidazo[4,5-c]pyridin-6-yl]oxy}phenyl)acetamide Triphenylphosphine (260 mg, 1.0 mmol) was added to a solution of the product from Step 5 (220 mg, 0.5 mmol) and N—BOC-ethanolamine (161 mg, 1.0 mmol) in dioxane (4 mL) followed by addition of di-isopropylazodicarboxylate (197 uL, 1.0 mmol) and the resulting solution was allowed to stir at rt overnight. The reaction mixture was poured into water and extracted with EtOAc. The organic phases were combined, washed with brine, dried (MgSO$_4$), filtered and the filtrate concentrated. The crude material was dissolved in dichloromethane (2 mL) and treated with TFA (1 mL) for 30 min, then concentrated and the residue was purified by reverse phase HPLC to give the title compound (38 mg, 16%). MS (ES+) m/e 487 [M+H]$^+$.

Example 3

4-{6-[(3-Aminophenyl)oxy]-1-ethyl-1H-imidazo[4,5-c]pyridin-2-yl}-furazan-3-amine

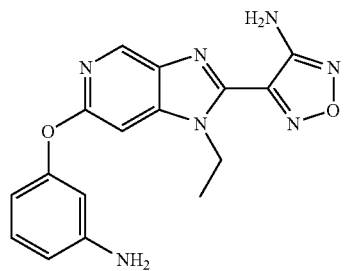

Step 1. 2-Chloro-N-ethyl-5-nitro-4-pyridineamine

The title compound was prepared by the method of Example 1, Step 4 starting from the product of Example 1, Step 3 and ethylamine. MS (ES+) m/e 202 [M+H]$^+$.

Step 2. 1,1-Dimethylethyl (3-{[4-(ethylamino)-5-nitro-2-pyridinyl]oxy}phenyl)carbamate The product of Step 1 (1.0 g, 5 mmol) in DMF (23 mL) was treated with 1,1-dimethylethyl (3-hydroxyphenyl) carbamate (1.3 g, 6 mmol) and potassium carbonate (6.9 g, 50 mmol). The resulting mixture was heated to 80° C. for 3 h., then partitioned between ethyl acetate and saturated aqueous ammonium chloride solution. The organic phase was washed with water and brine, then concentrated in vacuo. The residue was purified by column chromatography eluting with 20% ethyl acetate in hexane to afford the title compound (1.26 g, 68%). MS (ES+) m/e 375 [M+H]$^+$.

Step 3. 1,1-Dimethylethyl (3-{[5-amino-4-(ethylamino)-2-pyridinyl]oxy}phenyl)carbamate The product from Step 2 (1.26 g, 3.3 mmol) in ethanol (20 mL) was hydrogenated for 3 hours in the presence of 10% palladium on carbon under H₂ (50 psi). After filtration of the catalyst through Kieselguhr, the filtrate was concentrated in vacuo to afford the title compound (0.81 g, 70%). MS (ES+) m/e 345 [M+H]⁺.

Step 4. 4-{6-[(3-Aminophenyl)oxy]-1-ethyl-1H-imidazo[4,5-c]pyridin-2-yl}-furazan-3-amine The product from Step 3 (0.81 g, 2.3 mmol) and ethyl cyanoacetate (0.52 g, 4.6 mmol) were heated together at 195° C. for 25 minutes. After cooling the mixture to rt, the residue was dissolved in methanol (0.8 mL) and 5N hydrochloric acid (3 mL). The resulting mixture was treated portionwise with sodium nitrite (0.32 g, 4.6 mmol) and stirred at room temperature for 90 minutes. The pH of the mixture was adjusted to 11 by addition of 50% sodium hydroxide solution and a 50% solution of hydroxylamine in water (1.6 mL) was added. The mixture was heated at 110° C. for 16 h and the reaction allowed to cool to rt. The mixture was partitioned between ethyl acetate and water, then the organic phase was washed with brine and evaporated in vacuo. The residue was purified by HPLC to afford the title compound (0.12 g, 15%). MS (ES+) m/e 338 [M+H]⁺.

Example 4

N-(3-{[2-(4-Amino-furazan-3-yl)-1-ethyl-1H-imidazo[4,5-c]pyridin-6-yl]oxy}phenyl)-4-(methyloxy)benzamide

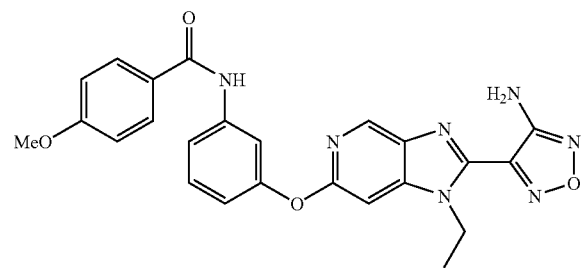

To a 0° C. solution of 0.10 g of the product of Example 3 (0.30 mmols) in DMF (1.0 mL) was added 0.041 mL of triethylamine (0.30 mmols) and 0.056 g of 4-methoxybenzoylchloride (0.33 mmols). The reaction mixture was allowed to warm to rt and stirred for 23 h. The reaction mixture was diluted with 1 mL of water and 5 mL of EtOAc. The layers were separated, and the aqueous layer was extracted with EtOAc. The combined organics were washed with water and concentrated to a partial volume. Methanol was added, and a solid precipitated from the solution. The precipitate was filtered off and dried and the crude product was purified by silica gel chromatography to provide the title compound as a white powder (0.029 g, 21%). MS (ES+) m/e 473 [M+H]⁺.

Example 5

N'-(3-{[2-(4-amino-furazan-3-yl)-1-ethyl-1H-imidazo[4,5-c]pyridin-6-yl]oxy}phenyl)-N,N-dimethylsulfamide

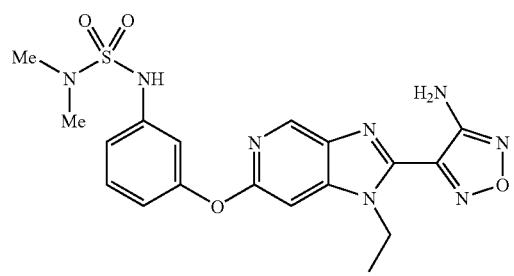

The title compound was prepared using N,N-dimethylsulfonyl chloride and the product from Example 3 via the same general procedure for example 4. MS (ES+) m/e 445 [M+H]⁺.

Example 6

N-(3-{[2-(4-amino-furazan-3-yl)-1-ethyl-1H-imidazo[4,5-c]pyridin-6-yl]oxy}phenyl)-3-pyridinecarboxamide

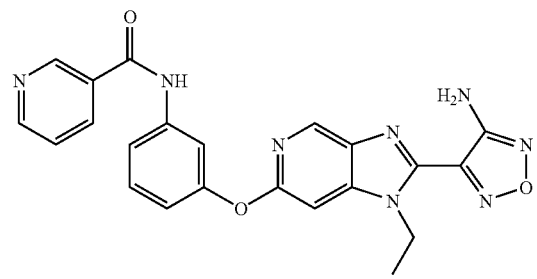

To a room temperature suspension of 0.036 g of nicotinic acid (0.30 mmols) and 0.061 g of EDCI (0.32 mmols) in dry DMF (2.0 mL) was added 0.043 g of HOBt (0.32 mmols). After stirring for 10 min., 0.10 g of the product of Example 3 (0.3 mmols) was added to the reaction mixture. After stirring for 1 h, the reaction was treated with an additional 0.061 g of EDCI (0.32 mmols). The mixture was allowed to stir for 27 h at rt. The reaction mixture was diluted with 2 mL of water and 10 mL of EtOAc. The layers were separated, and the organic layer was washed with water. The organics were dried over MgSO₄, filtered, and concentrated. The yellow residue was washed with methanol to yield an off-white solid (73 mg, 57%). MS (ES+) m/e 444 [M+H]⁺.

Example 7

N-{3-[2-(4-Amino-furazan-3-yl)-1-(1,2,3,4-tetrahydro-isoquinolin-7-yl)-1H-imidazo[4,5-c]pyridin-6-yloxy]-phenyl}-acetamide

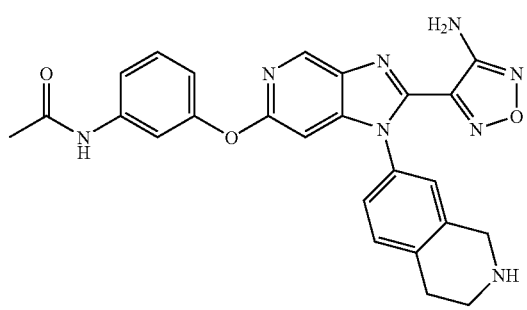

Step 1. 7-(2-Chloro-5-nitro-pyridin-4-ylamino)-3,4-dihydro-1H-isoquinoline-2-carboxylic acid tert-butyl ester To a solution of the 7-amino-3,4-dihydro-1H-isoquinoline-2-carboxylic acid tert-butyl ester (5.2 g, 21.0 mmol) in ethanol (60 mL) and THF (15 mL) was added NaHCO$_3$ (5.3 g, 63.0 mmol) followed by the product of Example 1, Step 3 (4.05 g, 21.0 mmol), and the reaction mixture was stirred overnight rt. The reaction mixture was concentrated then taken up in EtOAc and H$_2$O extracted with EtOAc, the organic layers were combined, dried over MgSO$_4$, filtered, and concentrated. The crude material was crystallized from EtOAc/hexane to give the title compound as a yellow solid. MS (ES+) m/e 406 [M+H]$^+$.

Step 2. 7-[2-(3-Acetylamino-phenoxy)-5-nitro-pyridin-4-ylamino]-3,4-dihydro-1H-isoquinoline-2-carboxylic acid tert-butyl ester A solution of 3-acetamidophenol (4.8 g, 32 mmol) in THF (200 mL) was cooled to 0° C. To the solution was added NaH (60% in oil, 1.3 g, 32 mol) and the mixture was warmed to rt and allowed to stir for 30 minutes. The product from Step 1 (~8.5 g, ~21 mmol) was added and the mixture was stirred at rt overnight then DMF (10 mL) was added and the solution was heated to 60° C. overnight. The reaction mixture was concentrated in-vacuo, then taken up in EtOAc and H$_2$O and extracted with EtOAc. The organic layers were combined, dried over MgSO$_4$, filtered, and concentrated. The crude oil was purified chromatography to give the title compound (4.3 g, 39%). MS (ES+) m/e 521 [M+H]$^+$.

Step 3. 7-[2-(3-Acetylamino-phenoxy)-5-amino-pyridin-4-ylamino]-3,4-dihydro-1H-isoquinoline-2-carboxylic acid tert-butyl ester The product from Step 2 (2.7 g, 5.2 mmol) was dissolved in MeOH (20 mL), Pd/C (5% on C, 100 mg) was added the mixture was hydrogenated with a balloon of hydrogen for 2 days, then filtered through celite. The filtrate was concentrated to give the title compound which was taken on without purification. MS (ES+) m/e 491 [M+H]$^+$.

Step 4. 7-[6-(3-Acetylamino-phenoxy)-2-cyanomethyl-imidazo[4,5-c]pyridin-1-yl]-3,4-dihydro-1H-isoquinoline-2-carboxylic acid tert-butyl ester The product from Step 3 (2.54 g crude) and cyanoacetic acid (0.88 g, 10.4 mmol) were dissolved in DMF (10 mL) and Et$_3$N (3.6 mL) was added. To the solution was added EDC (2.2 g, 11.4 mmol), and the mixture was allowed to stir at rt for 2 days. The reactin mixture was poured into water and extracted with ethyl acetate. The separated organic layer was dried over MgSO$_4$, filtered, and concentrated to give a dark oil. The oil was dissolved in AcOH (5 mL) and the solution was heated at 100° C. for 4 hours then cooled and concentrated in-vacuo to give the title compound as a dark foam that was taken on without further purification. MS (ES+) m/e 540 [M+H]$^+$.

Step 5. N-{3-[2-(4-Amino-furazan-3-yl)-1-(1,2,3,4-tetrahydro-isoquinolin-7-yl)-1H-imidazo[4,5-c]pyridin-6-yloxy]-phenyl}-acetamide The product from Step 4 (0.250 g, 0.46 mmol) was dissolved in MeOH (5 mL) and 2N HCl (3 mL). To the solution was added NaNO$_2$ (0.065 g, 0.92 mmol), and the mixture was allowed to stir at rt for 30 min. The reaction mixture was concentrated, then dissolved in THF (3 mL). Triethylamine (0.25 mL), and NH$_2$OH (50% aqueous solution, 0.07 mL) were added and the mixture was heated in a sealed tube to 90° C. for 1 hour. The reaction mixture was then cooled, poured into EtOAc and washed with H$_2$O. The organic layer was dried over MgSO$_4$, filtered, then concentrated in-vacuo to give a dark oil. The oil was dissolved in dioxane (3 mL) and Et$_3$N (0.5 mL) and the reaction mixture was heated in a sealed tube to 150° C. for 1 hour. The mixture was then cooled, and concentrated in-vacuo. The crude oil was dissolved in dichloromethane (2 mL) and to the solution was added 4N HCl in dioxane and the resulting solution was allowed to stir at rt for 30 min. The mixture was then concentrated in-vacuo, and the oil was dissolved in a minimal amount of MeOH then poured into Et$_2$O to afford the title compound as a tan solid (40 mg, 18%). MS (ES+) m/e 484 [M+H]$^+$.

Example 8

3-{[2-(4-Amino-furazan-3-yl)-1-phenyl-1H-imidazo[4,5-c]pyridin-6-yl]oxy}-N-[2-(4-morpholinyl)ethyl]benzamide

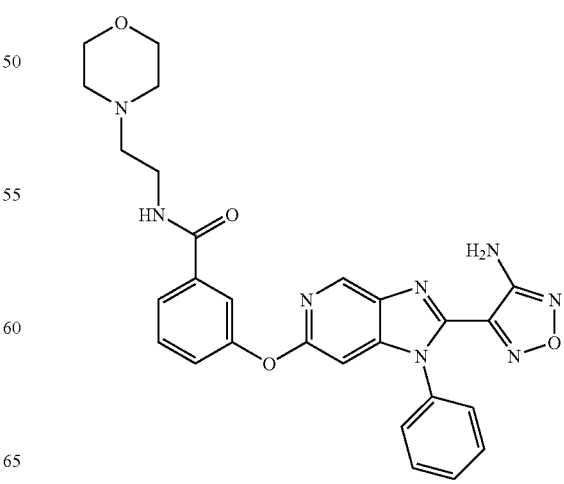

Step 1. 2-Hydroxy-4-methoxy-5-nitropyridine

THF (100 mL) was cooled to −78° C. and anhydrous NH₃ (~200 mL) was condensed into the THF. Potassium t-butoxide (45.5 g, 405 mmol) was added and the mixture was allowed to warm to ~−35° C. 4-Methoxy-3-nitropyridine (25.0 g, 162 mmol) was cooled to 0° C. in THF (200 mL) and a solution of t-BuOOH (5 M in decane, 34 mL, 170 mmol) was added over 10 min. This solution was then added dropwise to the KOt-Bu solution over 1 h, then stirred for 2 h at −35° C. and then carefully quenched with ~50 mL of sat. NH₄Cl solution. The mixture was allowed to vent and warm to rt overnight, then the organics were concentrated and the residue made acidic with NH₄Cl solution and filtered. The solid was washed with cold H₂O and dried to give the title compound as a tan solid (14.0 g, 51%).

Step 2. 2,4-Dibromo-5-nitropyridine

Phosphorous oxybromide (5.73 g, 20 mmol) was added to a suspension of the product from Step 1 (1.70 g, 10 mmol) in acetonitrile (20 mL) at rt then heated to reflux for 3 h. The reaction mixture was cooled and carefully poured onto ice and sat. aq. K₂CO₃ then extracted with EtOAc. The organic extracts were combined, washed with water and brine, dried (MgSO₄), filtered and concentrated to dive the title compound (2.1 g, 75%) as a dark solid. MS (ES+) m/e 279, 281, 285 [M+H]⁺.

Step 3. 2-Bromo-5-nitro-N-phenyl-4-pyridineamine

The product from Step 2 (7.55 g, 26.8 mmol) in THF (80 mL) and triethylamine (3.7 mL, 26.8 mmol) was treated with aniline (2.6 g, 27.9 mmol) and allowed to stir at rt until the reaction was judged complete by TLC. The solvent was removed in vacuo and the residue dissolved in ethyl acetate, washed (3×) with water and brinde, dried over Na₂SO₄ and concentrated in vacuo to afford the title compound (7.65 g, 97%). MS (ES+) m/e 294/296 [M+H]⁺.

Step 4. 6-Bromo-N⁴-phenyl-3,4-pyridinediamine

The product from Step 3 (7.42 g, 25.2 mmol) in acetic acid (80 mL) was treated with iron powder (5.65 g, 100.95 mmol) portionwise over 1 h while the temperature was maintained between 70-80° C. The hot reaction mixture was quickly filtered through a pad of celite and washed with methanol. The combined filtrates concentrated to give a dark red residue was treated with NaHCO₃ and extracted with ethyl acetate. The organic layers were washed brine, dried over Na₂SO₄ and concentrated to afford the title compound (6.1 g, 95%). MS (ES+) m/e 264/266 [M+H]⁺.

Step 5. (6-Bromo-1-phenyl-1H-imidazo[4,5-c]pyridin-2-yl)acetonitrile

The product from Step 4 (2.1 g, 7.95 mmol) and ethyl cyanoacetate (3.6 g, 31 mmol) were heated together at 195° C. in a sealed tube for 54 minutes. After cooling to room temperature, the product crystallized and the crystals were collected and washed with ethanol to give the title compound (0.87 g, 35%). MS (ES+) m/e 313/315 [M+H]⁺.

Step 6. (6-Bromo-1-phenyl-1H-imidazo[4,5-c]pyridin-2-yl)(hydroxyimino)acetonitrile The product from Step 5 (2.5 g, 7.99 mmol) in methanol (40 mL) and 2 N hydrochloric acid (16 mL) was treated portionwise with NaNO₂ (1.10 g, 16 mmol) and allowed to stir at rt for 1 h. The resulting tan precipitate was filtered and washed with methanol to give the title compound (2.7 g, 99%). MS (ES+) m/e 342/344 [M+H]⁺.

Step 7. 4-(6-Bromo-1-phenyl-1H-imidazo[4,5-c]pyridin-2-yl)-furazan-3-amine

The product from Step 6 (2.7 g, 7.93 mmol) in THF (5 mL) and triethylamine (1.1 mL, 7.93 mmol) was treated with a 50% solution of hydroxylamine in water (0.24 mL, 7.93 mmol). The mixture was heated at 120° C. in a sealed tube for 10 h and the reaction allowed to cool to room temperature. The resulting precipitate was filtered and dried in vacuo to afford the title compound (1.7 g, 60%). MS (ES+) m/e 357/359 [M+H]⁺.

Step 8. Methyl 3-{[2-(4-amino-furazan-3-yl)-1-phenyl-1H-imidazo[4,5-c]pyridin-6-yl]oxy}benzoate A heterogeneous mixture of the product from Step 7 (0.75 g, 2.1 mmol), methyl 3-hydroxybenzoate (1.5 equiv), 1,10-phenanthroline (1.5 equiv), copper (I) iodide (0.42 g, 2.2 mmol) and cesium carbonate (1.44 g, 3.78 mmol) in toluene (30 mL) and ethyl acetate (1.5 mL) was heated in a sealed tube at 125° C. for 2 days. The reaction mixture was cooled to rt triturated with ethyl acetate. The resulting crude solid was crystallized from ethanol to afford the title compound (0.30 g, 33%). MS (ES+) m/e 429 [M+H]⁺.

Step 9. 3-{[2-(4-Amino-furazan-3-yl)-1-phenyl-1H-imidazo[4,5-c]pyridin-6-yl]oxy}benzoic acid The product from Step 8 (0.22 g, 0.514 mmol) in THF (10 mL) was treated with a solution of 1N lithium hydroxide in water (1.5 mL) and heated to 65° C. for 10 h. The reaction mixture was cooled and concentrated and the residue was partitioned between water and ethyl acetate. The aqueous phase was extracted with ethyl acetate and the organic layers were combined, washed with brine and dried over Na₂SO₄ and concentrated to give the title compound (0.20 g, 94%). MS (ES+) m/e 415 [M+H]⁺.

Step 10. 3-{[2-(4-amino-furazan-3-yl)-1-phenyl-1H-imidazo[4,5-c]pyridin-6-yl]oxy}-N-[2-(4-morpholinyl)ethyl]benzamide The product from Step 9 (0.020 g, 0.048 mmol) in dichloromethane (2 mL) and N,N-diisopropylethylamine (0.02 mL, 0.11 mmol) was treated with N-(2-aminoethyl)morpholine and the PyBoP reagent (2 equiv) and stirred at rt for 2 h. The reaction mixture was concentrated and the residue was purified by reverse phase HPLC to give the compound (0.008 g, 31%). MS (ES+) m/e 527 [M+H]⁺.

Example 9

3-{[2-(4-Amino-furazan-3-yl)-1-ethyl-1H-imidazo[4,5-c]pyridin-6-yl]oxy}phenol

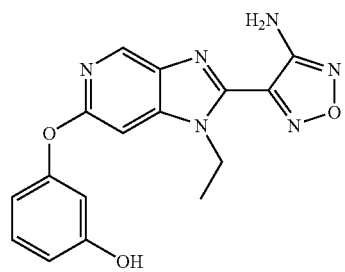

Step 1. 3-{[(t-Butyl)-(dimethyl)silyl]oxy}phenol 1,3-Benzenediol (5 g, 45 mmol) in dichloromethane (150 mL) was treated with chloro(t-butyl)dimethylsilane (7.5 g, 50 mmol) and triethylamine (5 g, 50 mmol). The resulting mixture was stirred at rt for 16 h then concentrated in vacuo and the residue was partitioned between ethyl acetate and water. The organic phase was washed with 6N NaOH, then concentrated in vacuo. The residue was purified by column chromatography eluting with 20% ethyl acetate in hexane to afford the title compound (4.3 g, 42%). MS (ES+) m/e 225 [M+H]+.

Step 2. 4-(6-Bromo-1-ethyl-1H-imidazo[4,5-c]pyridin-2-yl)-furazan-3-amine

The title compound was prepared from the product of Example 8, Step 2 and ethylamine by the general method of Example 8, Steps 3-6, followed by the general method of Example 2, Steps 4-5. MS (ES+) m/e 309, 311 [M+H]+.

Step 3. 3-{[2-(4-Amino-furazan-3-yl)-1-ethyl-1H-imidazo[4,5-c]pyridin-6-yl]oxy}phenol The product from Step 1 (46 mg, 0.20 mmol) in toluene (10 mL) was treated with the product from Step 2 (42 mg, 0.14 mmol), cuprous iodide (26 mg, 0.14 mmol), 1,10-phenanthroline (43 mg, 0.24 mmol), and cesium carbonate (88 mg, 0.27 mmol). The resulting mixture was heated to 120° C. for 48 hours in a sealed tube. After concentration the residue was purified by reverse phase HPLC to give the title compound (3.3 mg, 7%). MS (ES+) m/e 339 [M+H]+.

Example 10

2-(4-Amino-furazan-3-yl)-1-ethyl-N-(phenylmethyl)-1H-imidazo[4,5-c]pyridin-6-amine

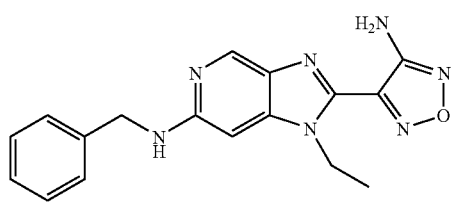

Under Ar, a suspension of the product from Example 9, Step 2 (18.9 mg, 61.1 μmol) in DMF (1 mL) was treated with benzylamine (12 μl, 110 μmol), copper iodide (2.3 mg, 12.2 μmol), phenyl 2-hydroxybenzoate (6.6 mg, 30.6 μmol), and potassium carbonate (16.9 mg, 122.2 μmol). This mixture was then heated to 170° C. by microwave for 40 min. After cooling rt, the reaction mixture was diluted with ethyl acetate and washed with water and brine. The organic layer was dried over Na2SO4, filtered and concentrated in vacuo. The residue was purified by reverse phase HPLC to give the title compound (2.6 mg, 10%). MS (ES+) m/e 336 [M+H]+.

Example 11

3-([2-(4-Amino-furazan-3-yl)-1-ethyl-1H-imidazo[4,5-c]pyridin-6-yl]thiophenol

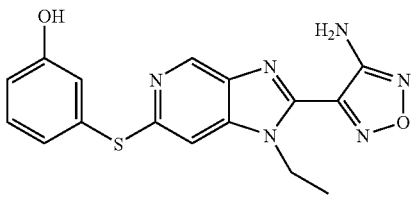

Under Ar, a suspension of the product from Example 9, Step 2 (15 mg, 48.5 μmol) in 1,4-dioxane (0.5 mL) and toluene (2.0 mL) was treated with tris(dibenzylidene-acetone)dipalladium (4.6 mg, 5 μmol), racemic-2,2'-bis(diphenylphosphino)-1,1'-binaphthyl (6.3 mg, 10 μmol), 3-{[(1,1-dimethylethyl)(dimethyl)silyl]oxy}benzenethiol (14 ml, 58.2 μmol), and sodium tert-butoxide (6.6 mg, 67.9 μmol). This mixture was then heated to 175° C. by microwave for 45 min. After cooling to rt, the reaction mixture was concentrated, redissolved in THF (3 mL) and treated with TBAF (0.5 mL, 1.0 M in THF) for 1 h. The reaction mixture was diluted with ethyl acetate (30 ml), washed with brine and the organic layer was dried over Na2SO4, filtered and concentrated in vacuo. The residue was purified by reverse phase HPLC to afford the title compound (4.4 mg, 16%). MS (ES+) m/e 355 [M+H]+.

Example 12

N-(3-{[2-(4-Amino-furazan-3-yl)-1-ethyl-1H-imidazo[4,5-c]pyridin-6-yl]thio}phenyl)ethanethioamide

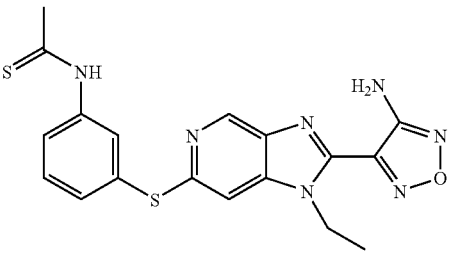

Step 1. N-(3-{[2-(4-Amino-furazan-3-yl)-1-ethyl-1H-imidazo[4,5-c]pyridin-6-yl]thio}phenyl)acetamide Under Ar, a suspension of the product from Example 9, Step 2 (50 mg, 162 μmol) in DME (1.4 mL) and toluene (2.8 mL) was treated with tris(dibenzylidene-acetone)dipalladium (15 mg, 16 μmol), racemic-2,2'-bis(diphenylphosphino)-1,1'-binaphthyl (20 mg, 32 μmol), N-(3-mercaptophenyl)acetamide (32.6 mg, 195 μmol), and sodium tert-butoxide (22 mg, 227 μmol). This mixture was then heated to 175° C. by microwave for 15 min. After cooling to rt, the reaction mixture was diluted with ethyl acetate (30 ml), filtered through a celite pad and the filtrate was concentrated in vacuo. The residue was purified by reverse phase HPLC to give the title compound (17 mg, 26%). MS (ES+) m/e 396 [M+H]$^+$.

Step 2. N-(3-{[2-(4-Amino-furazan-3-yl)-1-ethyl-1H-imidazo[4,5-c]pyridin-4-yl]thio}phenyl)ethanethioamide The product from Step 1 (15 mg, 37.9 μmol) in THF (3 mL) was treated with Lawesson's reagent (20 mg, 49.4 μmol) at 120° C. by microwave for 30 min. The reaction mixture was concentrated in vacuo and the residue was purified by reverse phase HPLC to give the title compound (4.2 mg, 21%). MS (ES+) m/e 412 [M+H]$^+$.

Example 13

1-(3-{[2-(4-Amino-furazan-3-yl)-1-ethyl-1H-imidazo[4,5-c]pyridin-6-yl]oxy}phenyl)ethanone

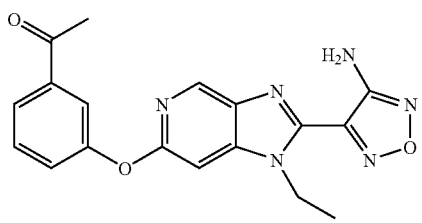

Under nitrogen, a suspension of the product from Example 9, Step 2 (42.7 mg, 138 μmol) in toluene (10 mL) was treated with copper iodide (26.3 mg, 138 μmol), 1,10-phenanthroline (45 mg, 245 μmol), 1-(3-hydroxyphenyl)ethanone (28.2 mg, 207 μmol), and cesium carbonate (90 mg, 276 μmol). This mixture was then heated to reflux for 36 h. After cooling to rt, the reaction mixture was diluted with ethyl acetate (50 ml), filtered through a celite pad and then the filtrate was concentrated in vacuo. The residue was purified by reverse phase HPLC to give the title compound (28.1 mg, 43%). MS (ES+) m/e 365 [M+H]$^+$.

Example 14

4-{2-(4-amino-furazan-3-yl)-6-[(3-aminophenyl)oxy]-1H-imidazo[4,5-c]pyridin-1-yl}phenyl 2-methylpropanoate

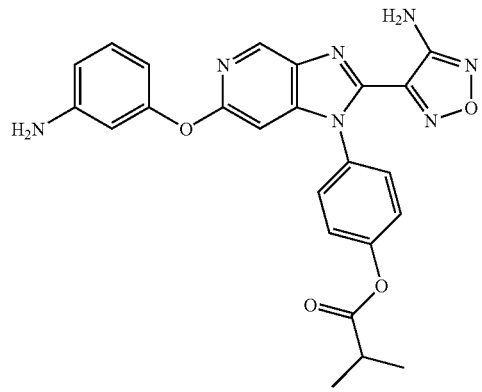

Step 1. 2-Chloro-5-nitro-N-{4-[(phenylmethyl)oxy]phenyl}-4-pyridineamine

The product of Example 1, Step 3 (15.2 g, 78.7 mmol), 4-benzyloxyaniline HCl (15.6 g, 78.7 mmol) and Et$_3$N (27 mL, 196.9 mmol) were combined in DMF (125 mL) and heated to 60° C. for 1 h. The reaction mixture was cooled and H2O (200 mL) was added dropwise over 1 h. The resulting yellow/orange precipitate was filtered and washed with Et2O to provide the title compound as a yellow powder (25.8 g, 92%). MS (ES+) m/e 356 [M+H]$^+$.

Step 2. 1,1-Dimethylethyl (3-{[5-nitro-4-({4-[(phenylmethyl)oxy]phenyl}amino)-2-pyridinyl]oxy}phenyl)carbamate A solution of 1,1-Dimethylethyl (3-hydroxyphenyl)carbamate (7.05 g, 33.7 mmol) in THF (20 mL) was added dropwise to a suspension of NaH (60% dispersion in oil, 1.34 g, 33.7 mmol) in THF (50 mL). The product of Step 1 (12.0 g, 33.7 mmol) in DMF (100 mL) was then added and the mixture was heated to 60° C. overnight. The reaction mixture was then cooled, poured into H$_2$O and extracted with EtOAc. The combined extracts were washed with brine, dried (MgSO$_4$), filtered and the filtrates were concentrated to give the title compound as a yellow solid (16.4 g, 92%) which was used without purification. MS (ES+) m/e 529 [M+H]$^+$.

Step 3. 1,1-Dimethylethyl [3-({5-amino-4-[(4-hydroxyphenyl)amino]-2-pyridinyl}oxy)phenyl]carbamate The product from Step 2 (16.4 g, 31.0 mmol) was hydrogenated with a balloon of H2 in the presence of 5% Pd/C (2 g) in MeOH (100 mL) over the weekend. The reaction mixture was then filtered through Celite and concentrated to give the title compound (13 g, quant.) which was used without purification. MS (ES+) m/e 409 [M+H]$^+$.

Step 4. 4-{2-(4-amino-furazan-3-yl)-6-[(3-aminophenyl)oxy]-1H-imidazo[4,5-c]pyridin-1-yl}phenol The title compound was prepared from the product of Step 3 by the general procedures of Example 1, Steps 7-8 followed by removal of the BOC group by treatment with trifluoroacetic acid to give the title compound. MS (ES+) m/e 402 [M+H]+.

Step 5. 4-{2-(4-Amino-furazan-3-yl)-6-[(3-aminophenyl)oxy]-1H-imidazo[4,5-c]pyridin-1-yl}phenyl 2-methylpropanoate A solution of the product of Step 4 (80 mg, 0.20 mmol) and 2-methylpropanoic acid (18.4 mg, 0.21 mmol) in 2 ml DMF was treated with 1-hydroxybenzotriazole hydrate (HOBT) (29.7 mg, 0.22 mmol). The resulting mixture was stirred for 10 minutes at room temperature before being treated with triethylamine (22 mg, 0.22 mmol) and 1-[3-(dimethylamino)propyl]-3-ethylcarbodiimide hydrochloride (EDC) (42 mg, 0.22 mmol). The reaction was kept at room temperature overnight. Purification of the crude mixture by reverse phase ($CH_3CN$ 30%-80% in $H_2O$ with 0.1% TFA) afforded 20 mg (31%) oil as title compound. $^1H$ NMR (400 MHz, DMSO-D6) δ ppm 8.89 (s, 1H), 7.68 (d, 2H, 8.8 Hz), 7.38 (d, 2H, 8.8 Hz), 7.32 (t, 1H, 8.0 Hz), 6.85 (d, 1H, 7.6 Hz), 6.79-6.91 (m, 3H), 5.5-6.8 (M, 6H), 2.88 (m, 1H), 1.28 (d, 6H, 6.8 Hz). MS (ES+) m/e 372.2 [M+H]+.

Example 15

Methyl 3-{[2-(4-amino-furazan-3-yl)-1H-imidazo[4,5-c]pyridin-6-yl]oxy}benzoate

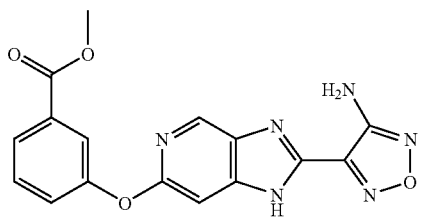

Step 1. 2-bromo-5-nitro-4-pyridineamine

Under nitrogen, to a solution of 2,4-dibromo-5-nitropyridine in THF (150 mL), was added ammonia (2.0M in MeOH), followed with triethylamine (5 mL). This mixture was then stirred at rt for 50 h. The reaction mixture was concentrated, taken up in EtOAC, filtered through a silica gel pad, and then concentrated in vacuo to afford the title compound (3.67 g, 95%). MS (ES+) m/e 218 [M+H]+.

Step 2. Methyl 3-[(4-amino-5-nitro-2-pyridinyl)oxy]benzoate

Under nitrogen, to a solution of 2-bromo-5-nitro-4-pyridineamine (3.67 g, 16.8 mmol) and methyl 3-hydroxybenzoate (2.82 g, 18.5 mmol) in DMF (100 mL), was added NaH (810 mg, 60% suspension, 20.2 mmol). 5 min later, the reaction mixture was heated to 65° C. The reaction mixture was concentrated, taken up in EtOAC, washed with NaOH solution (1.0N), saturated $NH_4Cl$ solution and brine, dried over $Na_2SO_4$, filtered and concentrated to afford the title compound, which was used directly to next step without further purification. MS (ES+) m/e 290 [+H]+.

Step 3. Methyl 3-[(4,5-diamino-2-pyridinyl)oxy]benzoate

To a solution of the product of Step 2 in MeOH (180 mL) and EtOAC (50 mL), was added 10% palladium on carbon (280 mg). This mixture was then stirred under hydrogen atmosphere for 36 h. The reaction mixture was filtered and then concentrated to afford the title compound, which was used directly to next step without further purification. MS (ES+) m/e 260 [M+H]+.

Step 4. Methyl 3-({4-amino-5-[(cyanoacetyl)amino]-2-pyridinyl}oxy)benzoate

To a solution of the product of Step 3 in THF (150 mL), was added cyanoacetic acid (870 mg, 10.2 mmol), EDC (4.32 g, 22.5 mmol) and triethylamine (8 ml, 51 mmol). This mixture was then stirred at rt for overnight. The reaction mixture was concentrated, taken up in EtOAC (300 mL), washed with saturated $NaHCO_3$ solution and brine, dried over $Na_2SO_4$, filtered and concentrated. The residue was dissolved in AcOH (100 ml), and then heated to 115° C. for 24 h. The reaction mixture was concentrated to afford the title compound, which was used directly to next step without further purification. MS (ES+) m/e 309 [M+H]+.

Step 5. Methyl 3-{[2-(4-amino-furazan-3-yl)-1H-imidazo[4,5-c]pyridin-6-yl]oxy}benzoate To a solution of the product of Step 4 in MeOH (200 mL), was added $NaNO_2$ (1.45 g, 20.4 mmol), followed by 2N HCl (50 ml, 100 mmol). After 2 h, this mixture was concentrated and filtered. The residue was taken up in THF (50 mL), $NH_2OH$ (50% aq. soln. 5 mL) and triethylamine (6 mL) were added and the mixture was then heated to 90° C. for 80 min in a sealed tube. The reaction mixture was diluted with EtOAC (100 mL), washed with saturated $NH_4Cl$ solution and brine, dried over $Na_2SO_4$, filtered and concentrated. The residue was then purified with flash chromatography (hexanes/ethyl acetate 3:1), to afford the title compound as a pale yellow solid (215 mg, 7% for 6 steps). $^1H$ NMR (400 MHz, DMSO) δ ppm 8.74 (s, 1H), 7.79 (d, 1H, 8.0 Hz), 7.51-7.56 (m, 3H), 7.44 (dd, 1H, 8.0 Hz, 2.0 Hz), 7.22 (bs, 1H), 6.81 (s, 1H), 3.85 (s, 3H). MS (ES+) m/e 353 [M+H]+.

Example 16

1-(3-{[2-(4-amino-furazan-3-yl)-1-ethyl-1H-imidazo[4,5-c]pyridin-6-yl]oxy}phenyl)-4-(4-morpholinyl)-1-butanol

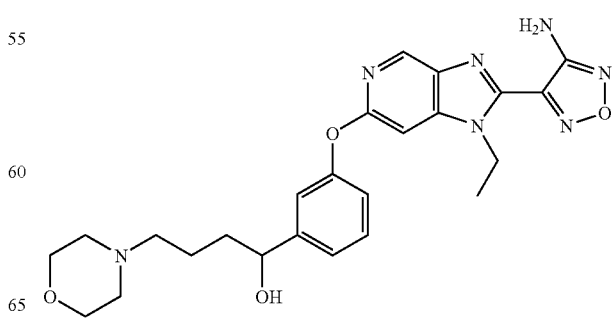

Step 1.
4-chloro-N-methyl-N-(methyloxy)butanamide

To a solution of 4-chlorobutanoyl chloride (5.64 g, 40.0 mmol) and a N,O-dimethylhydroxylamine hydrochloride (3.91 g, 40.0 mmol) in $CH_2Cl_2$ (80 mL) at 0° C., was added pyridine (7.2 ml, 88.0 mmol) in $CH_2Cl_2$ (30 mL). This mixture was kept stirring at 0° C. for 1 h, then warmed to rt. The reaction mixture then diluted with $Et_2O$ (200 mL), washed with saturated 1N HCl (2×), saturated $NaHCO_3$ solution and brine, dried over $Na_2SO_4$, filtered and concentrated to afford the title compound as a colorless oil (6.28 g, 95%). MS (ES+) m/e 166 [M+H]$^+$.

Step 2.
N-methyl-N-(methyloxy)-4-(4-morpholinyl)butanamide

To a solution of the product from Step 1 (3.01 g, 18.1 mmol) in MeCN (40 mL), was added $K_2CO_3$ (10 g, 72.4 mmol) and morpholine (1.58 mL, 18.1 mmol). This mixture was then heated to 105° C. in a sealed tube for overnight. The reaction mixture then diluted with MeCN (50 mL), then filtered and concentrated. Residue was taken up in $Et_2O$ (100 mL), washed with brine, dried over $Na_2SO_4$, filtered and concentrated to afford the title compound as a colorless oil (1.73 g, 44%), which was used directly to next step without further purification. MS (ES+) m/e 217 [M+H]$^+$.

Step 3. 4-(4-morpholinyl)-1-{3-[(phenylmethyl)oxy]phenyl}-1-butanone

Under argon, to a solution of 1-bromo-3-[(phenylmethyl)oxy]benzene (2.04 g, 7.76 mmol) in THF (30 mL) at −78° C., was added dropwise n-BuLi (5.1 mL, 1.6 M in Hexanes), 20 min after the addition, this solution was added to a solution the product from Step 3 (1.68 g, 7.76 mmol) in THF (30 mL) under argon at −78° C. 15 min later, the reaction mixture was slowly warmed to 0° C. The reaction mixture was poured into a mixture of EtOAC and $NH_4Cl$, then extracted with EtOAC (2×), organic layers were combined, washed with brine, dried over $Na_2SO_4$, filtered and concentrated. The residue was then purified with flash chromatography (hexanes/ethyl acetate 1:4), to afford the title compound as a colorless oil (932 mg, 35%). MS (ES+) m/e 340 [M+H]$^+$.

Step 4. 1-(3-hydroxyphenyl)-4-(4-morpholinyl)-1-butanone

To a solution of the product of Step 3 (352 mg, 1.04 mmol) in EtOH (15 mL), was added 10% palladium on carbon (50 mg), followed with 1-methyl-1,4-cyclohexadiene (1.5 mL). This suspension was then heated to reflux for 45 min. The reaction mixture was filtered and concentrate to afford the title compound as a white solid (255 mg, 99%). MS (ES+) m/e 250 [M+H]$^+$.

Step 5. 1-(3-{[2-(4-amino-furazan-3-yl)-1-ethyl-1H-imidazo[4,5-c]pyridin-6-yl]oxy}phenyl)-4-(4-morpholinyl)-1-butanone Under argon, to a suspension of 4-(6-bromo-1-ethyl-1H-imidazo[4,5-c]pyridin-2-yl)-furazan-3-amine (prepared by the method of Example 8, Steps 3-7, substituting ethylamine for aniline in Step 3) (80 mg, 0.26 mmol) in toluene (4 mL) and DME (4 mL), was added the product of Step 4 (78 mg, 0.31 mmol), CuI (50 mg, 0.26 mmol), 1,10-phenanthroline (94 mg, 0.52 mmol), and $Cs_2CO_3$ (170 mg, 0.52 mmol). This mixture was then heated to 170° C. by microwave for 15 min. The reaction mixture was added DMSO (1.5 mL), diluted with EtOAC/MeOH, sonicated for 10 min, then filtered and concentrated. The residue was purified with reverse phase HPLC (10% MeCN/$H_2O$→80% MeCN/$H_2O$, containing 0.1% TFA), to afford the title compound as a pale yellow solid (66 mg, 43%). MS (ES+) m/e 478 [M+H]$^+$.

Step 6. 1-(3-{[2-(4-amino-furazan-3-yl)-1-ethyl-1-imidazo[4,5-c]pyridin-6-yl]oxy}phenyl)-4-(4-morpholinyl)-1-butanol To a solution of the product of Step 5 (66 mg, 0.14 mmol) in wet THF, was added $NaBH_4$ (16 mg, 0.36 mmol). This mixture was stirred at rt for 1 h. DMSO (2 mL) was added and the reaction mixture was then concentrated. The residue was purified with reverse phase HPLC (10% MeCN/$H_2O$→80% MeCN/$H_2O$, containing 0.1% TFA), to afford the title compound as a pale yellow solid (6.5 mg, 10%). $^1$H NMR (400 MHz, DMSO) δ ppm 9.56 (bs, 1H), 8.76 (d, 1H, 0.8 Hz), 7.54 (s, 1H), 7.39 (t, 1H, 8.0 Hz), 7.16 (d, 1H, 7.6 Hz), 7.09 (d, 1H, 2.0 Hz), 6.96-6.99 (m, 2H), 5.44 (bs, 1H), 4.68 (q, 2H, 7.2 Hz), 4.60 (t, 1H, 7.0 Hz), 3.97 (d, 2H, 11.2 Hz), 3.62 (t, 2H, 12.0 Hz), 3.38 (d, 2H, 10.0 Hz), 2.99-3.13 (m, 4H), 1.58-1.75 (m, 4H), 1.41 (t, 3H, 7.2 Hz). MS (ES+) m/e 480 [M+H]$^+$.

Example 17

4-[1-ethyl-6-({3-[(1E)-3-(4-methyl-1-piperazinyl)-3-oxo-1-propen-1-yl]phenyl}oxy)-1H-imidazo[4,5-c]pyridin-2-yl]-furazan-3-amine

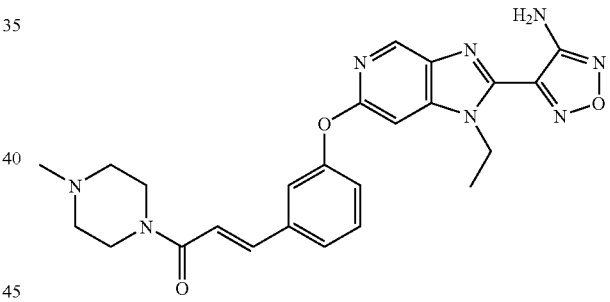

Step 1. 3-[(1E)-3-(4-methyl-1-piperazinyl)-3-oxo-1-propen-1-yl]phenol

Under nitrogen, to a solution of (2E)-3-(3-hydroxyphenyl)-2-propenoic acid (330 mg, 2.0 mmol) in THF (20 mL), was added 1-methylpiperazine (400 mg, 4.0 mmol), HOBT (810 mg, 6.0 mmol), HBTU (760 mg, 2 mmol), followed with 4-methylmorpholine (670 μL, 6.0 mmol). This mixture was then stirred at rt for overnight. The reaction mixture was concentrated and the residue was purified with reverse phase HPLC (5% MeCN/$H_2O$→60% MeCN/$H_2O$) to afford the title compound as a white solid (397 mg, 81%). MS (S$^+$) m/e 247 [M+H]$^+$.

Step 2. 4-[1-ethyl-4-({3-[(UE)-3-(4-methyl-1-piperazinyl)-3-oxo-1-propen-1-yl]phenyl}oxy)-1H-imidazo[4,5-c]pyridin-2-yl]-furazan-3-amine Under argon, to a suspension of 4-(6-bromo-1-ethyl-1H-imidazo[4,5-c]pyridin-2-yl)-furazan-3-amine (prepared by the method of Example 8, Steps 3-7, substituting ethylamine for aniline in Step 3) (80 mg, 0.26 mmol) in toluene (4 mL) and DME (4 mL), was added the product of Step 1 (100 mg, 0.41 mmol), CuI (50 mg, 0.26 mmol), 1,10-phenanthroline (94 mg, 0.52 mmol), and Cs$_2$CO$_3$ (170 mg, 0.52 mmol). This mixture was then heated to 170° C. by microwave for 20 min. The reaction mixture was added DMSO (2.0 mL), diluted with EtOAC/MeOH, sonicated for 10 min, then filtered and concentrated. Residue was purified with reverse phase HPLC (10% MeCN/H$_2$O→80% MeCN/H$_2$O, containing 0.1% TFA), to afford the title compound as a pale yellow solid (26.3 mg, 17%). $^1$H NMR (400 MHz, MeOD) δ ppm 8.72 (s, 1H), 7.65 (d, 1H, 15.6 Hz), 7.45-7.52 (m, 3H), 7.28 (s, 1H), 7.21 (d, 1H, 15.6 Hz), 7.16-7.18 (m, 1H), 4.72 (q, 2H, 7.2 Hz), 3.60 (bs, 4H), 3.16 (bs, 4H), 2.97 (s, 3H), 1.47 (t, 3H, 7.2 Hz). MS (ES+) m/e 475 [M+H]$^+$.

Example 18

4-[1-ethyl-6-({3-[3-(4-methyl-1-piperazinyl)-3-oxo-propyl]phenyl}oxy)-1H-imidazo[4,5-c]pyridin-2-yl]-furazan-3-amine

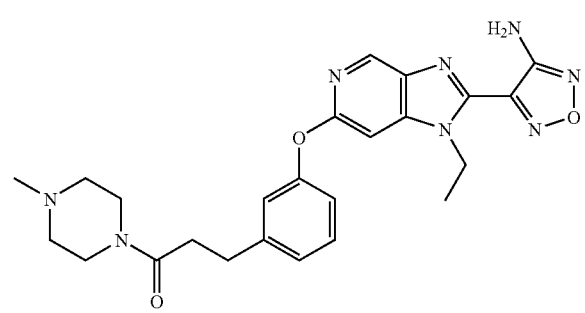

Step 1.
3-[3-(4-methyl-1-piperazinyl)-3-oxopropyl]phenol

To a solution the product of Example 17, Step 1 (300 mg, 1.22 mmol) in EtOH (15 mL), was added 10% palladium on carbon (50 mg), followed with 1-methyl-1,4-cyclohexadiene (1.5 mL). This suspension was then heated to reflux for 45 min. The reaction mixture was filtered and concentrated to afford the title compound, as a white solid (291 mg, 96%). MS (ES+) m/e 249 [M+H]$^+$.

Step 2. 4-[1-ethyl-6-({3-[3-(4-methyl-1-piperazinyl)-3-oxopropyl]phenyl}oxy)-1H-imidazo[4,5-c]pyridin-2-yl]-furazan-3-amine Under argon, to a suspension of 4-(6-bromo-1-ethyl-1H-imidazo[4,5-c]pyridin-2-yl)-furazan-3-amine (prepared by the method of Example 8, Steps 3-7, substituting ethylamine for aniline in Step 3) (100 mg, 0.32 mmol) in toluene (5 mL) and DME (5 mL), was added the product of Step 1 (128 mg, 0.52 mmol), CuI (62 mg, 0.32 mmol), 1,10-phenanthroline (116 mg, 0.65 mmol), and Cs$_2$CO$_3$ (210 mg, 0.65 mmol). This mixture was then heated to 170° C. by microwave for 40 min. To the reaction mixture was added DMSO (2.0 mL), diluted with EtOAC/MeOH, sonicated for 10 min, then filtered and concentrated. Residue was purified with reverse phase HPLC (10% MeCN/H$_2$O→80% MeCN/H$_2$O, containing 0.1% TFA), to afford the title compound as a pale yellow solid (12.0 mg, 8%). $^1$H NMR (400 MHz, MeOD) δ ppm 8.71 (d, 1H, 0.8 Hz), 7.35 (t, 1H, 8.0 Hz), 7.19 (d, 1H, 0.8 Hz), 7.10 (d, 1H, 7.6 Hz), 6.94-7.10 (m, 2H), 4.72 (q, 2H, 7.2 Hz), 3.42-3.61 (m, 4H), 2.96 (t, 2H, 7.6 Hz), 2.74 (t, 2H, 7.6 Hz), 2.40-2.48 (m, 4H), 2.35 (s, 3H), 1.46 (t, 3H, 7.2 Hz). MS (ES+) m/e 477 [M+H]$^+$.

Example 19

1-(3-{[2-(4-amino-furazan-3-yl)-1-ethyl-1H-imidazo[4,5-c]pyridin-6-yl]oxy}phenyl)-2-methyl-4-(4-morpholinyl)-1-butanone

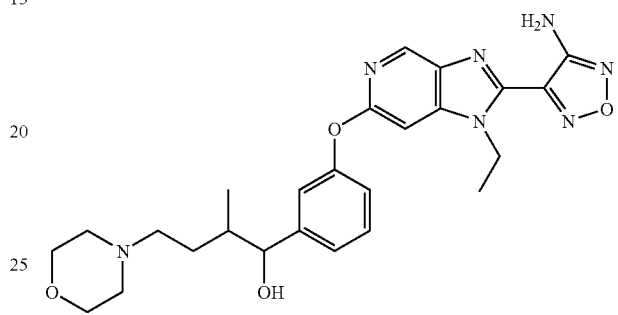

Step 1. 2-methyl-4-(4-morpholinyl)-1-{3-[(phenylmethyl)oxy]phenyl}-1-butanone

To a solution of 4-(4-morpholinyl)-1-{3-[(phenylmethyl)oxy]phenyl}-1-butanone (88 mg, 0.26 mmol) in THF (3 mL), was added NaH (23 mg, 60% suspension, 0.57 mmol). This suspension was stirred at rt for 30 min, then MeI (25 μl, 0.39 mmol) was added. The reaction mixture was stirred at rt for 3 h, then quenched with water. The reaction mixture was added EtOAC (100 ml), washed with brine, dried over Na$_2$SO$_4$, filtered and concentrated. The residue was then purified with flash chromatography (hexanes/ethyl acetate 1:2), to afford the title compound as a colorless oil (74 mg, 81%). MS (ES+) m/e 354 [M+H]$^+$.

Step 2. 1-(3-hydroxyphenyl)-2-methyl-4-(4-morpholinyl)-1-butanone

To a solution of the product of Step 1 (119 mg, 0.34 mmol) in EtOH (10 mL), was added 10% palladium on carbon (50 mg), followed with 1-methyl-1,4-cyclohexadiene (1 mL). This suspension was then heated to reflux for 15 min. The reaction mixture was filtered and concentrate to afford the title compound as a white solid (88 mg, 99%). MS (ES+) m/e 264 [M+H]$^+$.

Step 3. 1-(3-{[2-(4-amino-furazan-3-yl)-1-ethyl-1H-imidazo[4,5-c]pyridin-6-yl]oxy}phenyl)-2-methyl-4-(4-morpholinyl)-1-butanone Under argon, to a suspension of 4-(6-bromo-1-ethyl-1H-imidazo[4,5-c]pyridin-2-yl)-furazan-3-amine (prepared by the method of Example 8, Steps 3-7, substituting ethylamine for aniline in Step 3) (80 mg, 0.26 mmol) in toluene (4 mL) and DME (4 mL), was added the product of Step 2 (88 mg, 0.31 mmol), CuI (50 mg, 0.26 mmol), 1,10-phenanthroline (94 mg, 0.52 mmol), and Cs$_2$CO$_3$ (170 mg, 0.52 mmol). This mixture was then heated to 170° C. by microwave for 15 min.

To the reaction mixture was added DMSO (2.0 mL), diluted with EtOAC/MeOH, sonicated for 10 min, then filtered and concentrated. The residue was purified with reverse phase HPLC (10% MeCN/H$_2$O→80% MeCN/H$_2$O, containing 0.1% TFA), to afford the title compound as a pale yellow solid (72.0 mg, 46%). $^1$H NMR (400 MHz, DMSO) δ ppm 9.71 (bs, 1H), 8.77 (d, 1H, 0.8 Hz), 7.84 (d, 1H, 8.0 Hz), 7.69 (t, 1H, 2 Hz), 7.59-7.64 (m, 2H), 7.45 (dd, 1H, 8 Hz, 0.8 Hz), 6.96 (s, 2H), 4.70 (q, 2H, 7.2 Hz), 3.98 (d, 2H, 12.4 Hz), 3.60-3.81 (m, 2H), 3.42-3.47 (m, 2H), 3.01-3.19 (m, 4H), 1.96-2.01 (m, 1H), 1.41 (t, 3H, 7.2 Hz), 1.38 (d, 3H, 10.4 Hz). MS (ES+) m/e 492 [M+H]$^+$.

Example 20

1-(3-{[2-(4-amino-furazan-3-yl)-1-ethyl-1H-imidazo[4,5-c]pyridin-6-yl]oxy}phenyl)-4-(4-methyl-1-piperazinyl)-4-oxo-1-butanone

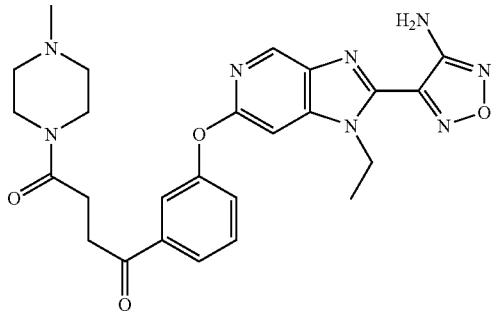

Step 1. 4-(3-{[(1,1-dimethylethyl)(dimethyl)silyl]oxy}phenyl)-4-oxobutanoic acid Under argon, to a solution of [(3-bromophenyl)oxy](1,1-dimethylethyl)-dimethylsilane (1.5 g, 5.22 mmol) in THF (60 mL) at −78° C., was added dropwise n-BuLi (3.6 mL, 1.6 M in hexanes), 20 min after the addition, this solution was added to a solution of dihydro-2,5-furandione (630 mg, 6.26 mmol) in THF (10 mL) under argon at −78° C. 15 min later, the reaction mixture was slowly warmed to rt overnight. The reaction mixture was diluted with EtOAc (50 mL), then extracted with NaOH (20 ml, 1.0 N). Aquaous layer was acidified with HCl (1.0N) until pH=2, then extracted with EtOAc (100 mL). The organic layer was washed with brine, dried over Na$_2$SO$_4$, filtered and concentrated to afford the title compound as a colorless crystal (546 mg, 54%). MS (ES+) m/e 195 [M+H]$^+$.

Step 2. 1-(3-hydroxyphenyl)-4-(4-methyl-1-piperazinyl)-4-oxo-1-butanone

Under nitrogen, to a solution of the product of Step 1 (490 mg, 2.52 mmol) in DMF (10 mL), was added 1-methylpiperazine (505 mg, 5.04 mmol), HOBT (1.02 g, 7.6 mmol), HBTU (950 mg, 2.5 mmol), followed with 4-methylmorpholine (770 µL, 7.6 mmol). This mixture was then stirred at rt overnight. The reaction mixture was concentrated and the residue was purified with reverse phase HPLC (5% MeCN/H$_2$O→50% MeCN/H$_2$O), to afford the title compound as white solid (572 mg, 82%). MS (ES+) m/e 277 [M+H]$^+$.

Step 3. 1-(3-{[2-(4-amino-furazan-3-yl)-1-ethyl-1H-imidazo[4,5-c]pyridin-6-yl]oxy}phenyl)-4-(4-methyl-1-piperazinyl)-4-oxo-1-butanone Under argon, to a suspension of 4-(6-bromo-1-ethyl-1H-imidazo[4,5-c]pyridin-2-yl)-furazan-3-amine (prepared by the method of Example 8, Steps 3-7, substituting ethylamine for aniline in Step 3) (80 mg, 0.26 mmol) in toluene (4 mL) and DME (4 mL), was added the product of Step 2 (145 mg, 0.52 mmol), CuI (50 mg, 0.26 mmol), 1,10-phenanthroline (94 mg, 0.52 mmol), and Cs2CO3 (210 mg, 0.65 mmol). This mixture was then heated to 170° C. by microwave for 25 min. The reaction mixture was added DMSO (2.0 mL), diluted with EtOAC/MeOH, sonicated for 10 min, then filtered and concentrated. The residue was purified with reverse phase HPLC (10% MeCN/H$_2$O→80% MeCN/H$_2$O, containing 0.1% TFA), to afford the title compound as a pale yellow solid (7.3 mg, 5%). $^1$H NMR (400 MHz, MeOD) δ ppm 8.75 (s, 1H), 7.91 (d, 1H, 7.6 Hz), 7.73-7.75 (m, 1H), 7.59 (td, 1H, 8.0 Hz, 2.0 Hz), 7.45 (dt, 1H, 8 Hz, 0.8 Hz), 7.36 (s, 1H), 4.77 (q, 2H, 7.2 Hz), 3.40-3.58 (m, 8H), 2.86-3.14 (m, 4H), 2.98 (s, 3H), 1.50 (t, 3H, 7.2 Hz). MS (ES+) m/e 505 [M+H]$^+$.

Example 21

3-{[2-(4-amino-furazan-3-yl)-1-ethyl-1H-imidazo[4,5-c]pyridin-6-yl]methyl}-N-[2-(4-morpholinyl)ethyl]benzamide

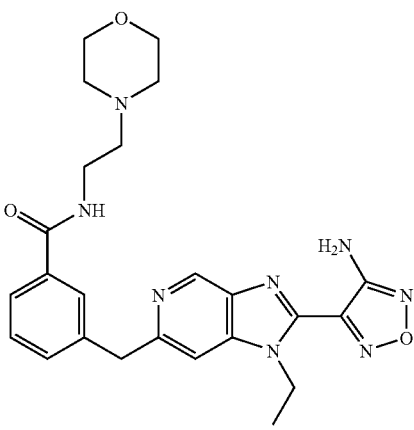

Step 1. Methyl 3-{[2-(4-amino-furazan-3-yl)-1-ethyl-1H-imidazo[4,5-c]pyridin-6-yl]methyl}benzoate Under argon, to a suspension of Rieke Zinc (650 µl, 5% suspension in THF), was added dropwise methyl 3-(bromomethyl)benzoate (118 mg, 0.50 mmol) in THF (5 mL). This mixture was heated briefly to reflux with a heat gun, then cooled to rt and stirred for 4 h. The above mixture was then filtered into a mixture of 4-(6-bromo-1-ethyl-1H-imidazo[4,5-c]pyridin-2-yl)-furazan-3-amine (prepared by the method of Example 8, Steps 3-7, substituting ethylamine for aniline in Step 3) (110 mg, 0.36 mmol) and tetrakis(triphenylphosphine)palladium (15 mg, 13 mmol), then heated to 110° C. by microwave for 20 min. The reaction mixture was added DMSO (2.0 mL) and concentrated. Residue was purified with reverse phase HPLC (10% MeCN/H$_2$O→80% MeCN/H$_2$O), to afford the title compound as a pale yellow solid (96.6 mg, 72%). MS (ES+) m/e 379 [+H]$^+$.

Step 2. 3-{[2-(4-amino-furazan-3-yl)-1-ethyl-1H-imidazo[4,5-c]pyridin-6-yl]methyl}benzoic acid To a solution of the product from Step 1 (85 mg, 0.22 mmol) in MeOH (12 ml) and water (4 ml), was added LiOH (40 mg, 0.95 mmol). This mixture was then heated to 80° C. for 2 h. Reaction mixture was concentrated, dissolved in 10 ml water, acidified with 1 N HCl to pH=5, then filtered and washed with water to afford a pale yellow solid (67 mg, 82%). MS (ES+) m/e 365 [M+H]+.

Step 3. 3-{[2-(4-amino-furazan-3-yl)-1-ethyl-1H-imidazo[4,5-c]pyridin-6-yl]methyl}-N-[2-(4-morpholinyl)ethyl]benzamide Under nitrogen, to a solution of the product of Step 2 (31 mg, 85 µmol) in DMF (2 mL), was added [2-(4-morpholinyl)ethyl]amine (23 mg, 170 mmol), HOBT (35 mg, 0.26 mmol), HBTU (49 mg, 0.13 mmol), followed with 4-methylmorpholine (30 µL, 0.26 mmol). This mixture was then stirred at rt for overnight. The reaction mixture was concentrated, residue was purified with reverse phase HPLC (10% MeCN/H2O→80% MeCN/H2O, containing 0.1% TFA), to afford the title compound as a pale yellow solid (53 mg, 90%). %). 1H NMR (400 MHz, DMSO) δ ppm 9.74 (t, 1H, 4.4 Hz), 9.28 (s, 1H), 8.73 (t, 1H, 5.2 Hz), 8.16 (s, 1H), 7.87 (s, 1H), 7.73 (d, 1H, 8.0 Hz), 7.56 (d, 1H, 7.2 Hz), 7.49 (d, 1H, 7.6 Hz), 6.96 (s, 2H), 4.72 (q, 2H, 7.2 Hz), 4.41 (s, 2H), 4.00 (d, 2H, 11.2 Hz), 3.53-3.68 (m, 6H), 3.30 (bs, 2H), 3.14-3.17 (m, 2H), 1.42 (t, 3H, 7.2 Hz). MS (ES+) m/e 477 [M+H]+.

Example 22

N-(3-{[2-(4-amino-furazan-3-yl)-1-ethyl-1H-imidazo[4,5-c]pyridin-6-yl]oxy}phenyl)-4-{[2-(4-morpholinyl)ethyl]oxy}benzamide

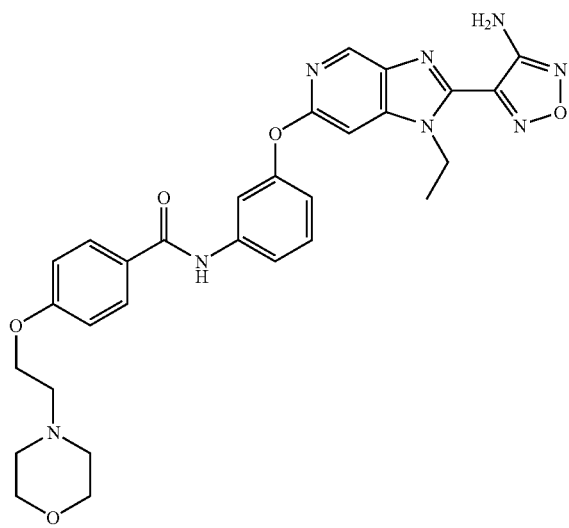

N-(3-{[2-(4-amino-furazan-3-yl)-1-ethyl-1H-imidazo[4,5-c]pyridin-6-yl]oxy}phenyl)-4-{[2-(4-morpholinyl)ethyl]oxy}benzamide Under argon, to a suspension of the HCl salt of 4-{[2-(4-morpholinyl)ethyl]oxy}benzoic acid (3.98 g, 13.8 mmol) in CH2Cl2 (100 ml) was added DMF (40 µl), followed with oxalylchloride (3.6 ml, 41.4 mmol). This mixture was then heated to reflux until a clear solution resulted. The reaction mixture was then concentrated, added CH2Cl2 (20 mL) and reconcentrated. A suspension of the above product in CH2Cl2 (100 mL), was added to a suspension of the product of Example 3 (3.96 g, 11.7 mmol) in pyridine (30 mL). This mixture was then heated to 70° C., the CH2Cl2 was distilled off, then stirred for 1 h. CH2Cl2 (200 mL) was added to the cooled reaction mixture, stirred for 15 min and then filtered to provide a first crop of product (crop 1). The filtrate was concentrated in vacuo and the residue taken up in EtOAc, washed with water (4×), brine, dried over Na2SO4, filtered and concentrated to provide Crop 2. Crops 1 and 2 were combined and recrystallized from MeOH to afforded a off white solid (5.54 g, 83%). 1H NMR (400 MHz, DMSO) δ ppm 11.35 (bs, 1H), 10.22 (s, 1H), 8.79 (d, 1H, 0.8 Hz), 7.99 (d, 2H, 8.8 Hz), 7.58-7.64 (m, 3H), 7.37 (t, 1H, 8.0 Hz), 7.12 (d, 2H, 8.8 Hz), 6.95 (s, 2H), 6.84-6.87 (m, 1H), 4.70 (q, 2H, 7.2 Hz), 4.53 (bs, 2H), 3.81-3.98 (m, 4H), 3.49-3.58 (m, 4H), 3.18-3.36 (m, 2H), 1.41 (t, 3H, 7.2 Hz). MS (ES+) m/e 571 [M+H]+.

Example 23

3-{[2-(4-amino-furazan-3-yl)-1-phenyl-1H-imidazo[4,5-c]pyridin-6-yl]oxy}-N-[2-(4-morpholinyl)ethyl]benzenesulfonamide

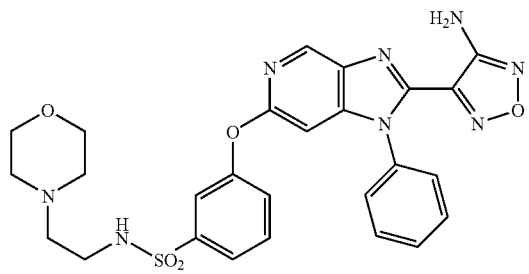

Step 1. 3-(Methyloxy)-N-[2-(4-morpholinyl)ethyl]benzenesulfonamide

2-Morpholinoethylamine (1.75 mL, 13.3 mmol) was added over 10 min to a solution of 3-(methyloxy)benzenesulfonyl chloride (2.5 g, 12.1 mmol) in CH2Cl2 (10 mL) and pyridine (4 mL) and the resulting solution was stirred at rt for 1 h. The mixture was concentrated, dissolved in EtOAc and the organic phase was washed with H2O and brine, dried (MgSO4), filtered and the filtrate was concentrated to give an orange oil (3.3 g, 92%) which was used directly in the next step. MS (ES+) m/e 301 [M+H]+.

Step 2. 3-Hydroxy-N-[2-(4-morpholinyl)ethyl]benzenesulfonamide

A solution of boron tribromide (1M in CH2Cl2, 20 mL, 20 mmol) was added to a −78° C. solution of the product of Step 1 in CH2Cl2 (50 mL) and the resulting mixture was allowed to warm to 0° C. After 2 h at 0° C. the mixture was re-cooled to −78° C. and quenched with sat. aq. NaHCO3 solution and allowed to warm to rt. The mixture was extracted with EtOAc, and the organic layers was washed with H2O and brine, dried (MgSO$_4$), filtered and the filtrate was concentrated to give the title compound as a crude oil (1.9 g, 66%) which was used directly in the next step. MS (ES+) m/e 287 [M+H]$^+$.

Step 3. N-[2-(4-Morpholinyl)ethyl]-3-{[5-nitro-4-(phenylamino)-2-pyridinyl]oxy}benzenesulfonamide A solution of the product of Step 2 (1.9 g, 6.6 mmol) in DMF (10 mL) was added dropwise over 10 min to a suspension of NaH (60% dispersion in oil, 265 mg, 6.6 mmol) in DMF (10 mL). After the final addition, a solution of the product of Example 1, Step 4 (1.65 g, 6.6 mmol) in DMF (15 mL) was added and the reaction mixture was heated to 60° C. overnight. The reaction mixture was cooled, poured into H$_2$O and extracted with EtOAc. The organic layers were combined, washed with H$_2$O and brine, dried (MgSO$_4$), filtered and the filtrate was concentrated. The crude product was purified by column chromatography (10%-100% EtOAc in hexane) to give the title compound as an orange oil (3.3 g, quant.). MS (ES+) m/e 500 [M+H]$^+$.

Step 4. 3-{[5-Amino-4-(phenylamino)-2-pyridinyl]oxy}-N-[2-(4-morpholinyl)ethyl]benzenesulfonamide The product of Step 3 (3.3 g, 6.6 mmol) was hydrogenated overnight with a balloon of hydrogen gas in MeOH (50 mL) in the presence of 5% Pd/C (300 mg). The reaction mixture was filtered through Celite and concentrated to give the title compound as a dark oil which was used directly in the next step (~3.1 g, quant.).

Step 5. 3-{[2-(Cyanomethyl)-1-phenyl-1H-imidazo[4,5-c]pyridin-6-yl]oxy}-N-[2-(4-morpholinyl)ethyl]benzenesulfonamide The product of Step 4 (3.1 g, 6.6 mmol), cyanoacetic acid (1.1 g, 13.2 mmol) and EDCI (2.5 g, 13.2 mmol) were combined in CH$_2$Cl$_2$ (25 mL). Triethylamine (3.7 mL, 26.4 mmol) was added and the resulting solution was allowed to stir overnight at rt. The reaction mixture was poured into H$_2$O and extracted with EtOAc. The organic layers were combined, washed with H$_2$O and brine, dried (MgSO$_4$), filtered and the filtrate was concentrated to give the crude amide which was used directly.

The crude amide from above was heated to 110° C. in glacial acetic acid (15 mL) for 5 h. The reaction mixture was then cooled and concentrated, the residue was made basic with aq. K$_2$CO$_3$ solution and the mixture was extracted with EtOAc. The organic layers were combined, washed with H$_2$O and brine, dried (MgSO$_4$), filtered and the filtrate was concentrated to give an oil which was purified by column chromatography (0%-5% MeOH in CH$_2$Cl$_2$) to give the title compound (2.4 g, 71% over two steps) as an off white foam. MS (ES+) m/e 519 [M+H]$^+$.

Step 6. 3-{[2-(4-Amino-furazan-3-yl)-1-phenyl-1H-imidazo[4,5-c]pyridin-6-yl]oxy}-N-[2-(4-morpholinyl)ethyl]benzenesulfonamide Sodium nitrite (100 mg, 1.4 mmol) was added to a solution of the product of Step 5 (500 mg, 0.96 mmol) in MeOH (5 mL) and 1M HCl (4 mL) and the resulting mixture was allowed to stir at rt for 30 min. The reaction mixture was poured into H$_2$O and extracted with EtOAc. The organic layers were combined, washed with H$_2$O and brine, dried (MgSO$_4$), filtered and the filtrate was concentrated to give a solid which was triturated with MeOH to give the desired oxime (271 mg, 52%) as a tan solid which was used directly in the next step. MS (ES+) m/e 549 [M+H]$^+$.

A slurry of the oxime from above (270 mg, 0.5 mmol) in dioxane (5 mL) and Et$_3$N (2 mL) was treated with hydroxylamine (50% aq. soln., 30 uL, 0.5 mmol) and heated to 110° C. overnight. The reaction mixture was then cooled and concentrated, partitioned between H$_2$O and EtOAc and the mixture was extracted with EtOAc. The organic layers were combined, washed with H$_2$O and brine, dried (MgSO$_4$), filtered and the filtrate was concentrated to give a solid which was triturated with EtOAc to provide the title compound as a tan solid. MS (ES+) m/e 563 [M+H]$^+$.

Example 24

N-(3-{[2-(4-amino-furazan-3-yl)-1-ethyl-1H-imidazo[4,5-c]pyridin-6-yl]oxy}phenyl)-6-{[2-(4-morpholinyl)ethyl]oxy}-3-pyridinecarboxamide

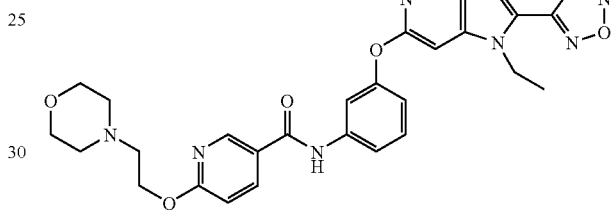

Step 1. 6-Oxo-1,6-dihydro-3-pyridinecarbonyl chloride

4-Hydroxynicotinic acid (2.09 g, 15 mmol) was heated to 80° C. in CH$_3$CN (10 mL) and pyridine (6 uL, 0.075 mmol). Thionyl chloride (1.15 mL, 15.8 mmol) was added dropwise with caution and heating was continued for 30 min after the final addition. The reaction mixture was cooled and the precipitate which formed as filtered, washed with cold CH$_3$CN and dried to give the title compound as a tan solid (1.6 g, 68%).

Step 2. N-(3-{[2-(4-Amino-1,2,5-oxadiazol-3-yl)-1-ethyl-1H-imidazo[4,5-c]pyridin-6-yl]oxy}phenyl)-6-oxo-1,6-dihydro-3-pyridinecarboxamide The product of Step 1 (93 mg, 0.6 mmol) was added to a solution of the product of Example 3 (200 mg, 0.6 mmol) in pyridine (1 mL) and the resulting mixture was allowed to stir at rt for 30 min. The solution was poured into H$_2$O and the precipitate which formed as filtered, washed with H$_2$O and Et$_2$O and dried to give the title compound as a tan solid (150 mg, 55%). MS (ES+) m/e 459 [M+H]$^+$.

Step 3. N-(3-{[2-(4-Amino-furazan-3-yl)-1-ethyl-1H-imidazo[4,5-c]pyridin-6-yl]oxy}phenyl)-6-{[2-(4-morpholinyl)ethyl]oxy}-3-pyridinecarboxamide 2-Chloroethylmorpholine hydrochloride (104 mg, 0.6 mmol) was added to a slurry of the product of Step 2 (135 mg, 0.3 mmol) and powdered K$_2$CO$_3$ (1 g) in DMF (2 mL) and the mixture was heated to 80° C. for 3 h. The mixture was cooled, diluted with H$_2$O and extracted with EtOAc. The combined organic extracts were washed with H₂O and brine, dried (MgSO₄), filtered and the filtrate was concentrated to give a yellow oil which was purified by reverse phase HPLC to give the title compound (50 mg, 30%). ¹H NMR (400 MHz, CD₃OD) δ ppm 9.13 (s, 1H), 8.69 (s, 1H), 8.09 (d, J=9.3, 1H); 7.92 (s, 1H), 7.69 (d, J=8.0, 1H), 7.60-7.53 (m, 2H), 7.12 (d, J=8.0, 1H), 6.67 (d, J=9.4, 1H), 4.76 (br q, 2H), 4.53 (br m, 2H), 3.83-3.70 (m, 8H), 3.33 (m, 2H), 1.46 (br t, 3H). MS (ES+) m/e 572 [M+H]⁺.

ROCK Kinase Assay:

ROCK inhibitor activity was determined using human recombinant ROCK1 kinase domain (amino acid 2-543) expressed in Sf9 cells (see WO9967283). The enzyme was purified using His-tag NTA column and Source 15 HPLC chromatography. The assay of Rock-1 activity involved incubation with peptide substrate and ATP³³, the subsequent incorporation of P³³ into the peptide was quantified by Scintillation Proximity Assay (SPA—Amersham Pharmacia).

For IC50 determination, test compounds were typically dissolved at 10 mM in 100% DMSO, with subsequent serial dilution in 100% DMSO. Compounds were typically assayed over an eleven-point dilution range with a concentration in the assay of 50 uM to 0.8 nM, in 3-fold dilutions. IC50 values were calculated by bespoke curve fitting software and then converted to pIC50.

Assays were performed in opaque, white walled, 384 well plates, in a total assay volume of 20 ul. The assays contained: 1 nM hROCK1; 1 uM biotinylated peptide (biotin-Ahx-AKRRRLSSLRA-CONH₂); 1 uM ATP; 1.85 kBq per well ATP(□-33P); 25 mM Hepes pH 7.4; 15 mM MgCl₂; 0.015% BSA. The reactions were incubated at 22° C. for 120 minutes, then terminated by the addition of a 50 ul solution containing 60 mM EDTA and streptavidin PVT SPA beads. The SPA beads were added to a concentration of 0.14 mg per well. The plates were allowed to incubate at 22° C. for 10 minutes before centrifugation at 1500 rpm for 1 minute. P³³ incorporation was quantified by scintillation counting in a Packard TopCount.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A compound selected from the group consisting of:
   3-{[2-(4-Amino-furazan-3-yl)-1-ethyl-1H-imidazo[4,5-c]pyridin-6-yl]thio}phenol;
   N-(3-{[2-(4-Amino-furazan-3-yl)-1-ethyl-1H-imidazo[4,5-c]pyridin-6-yl]thio}phenyl)acetamide;
   N-(3-{[2-(4-Amino-furazan-3-yl)-1-ethyl-1H-imidazo[4,5-c]pyridin-6-yl]thio}phenyl)ethanethioamide;
   4-(6-{[3,4-Bis(methyloxy)phenyl]thio}-1-ethyl-1H-imidazo[4,5-c]pyridin-2-yl)-furazan-3-amine;
   Methyl 3-{[2-(4-amino-furazan-3-yl)-1-ethyl-1H-imidazo[4,5-c]pyridin-6-yl]thio}benzoate;
   4-(1-Ethyl-6-{[3-(methyloxy)phenyl]thio}-1H-imidazo[4,5-c]pyridin-2-yl)-furazan-3-amine;
   3-{[2-(4-Amino-furazan-3-yl)-1-ethyl-1H-imidazo[4,5-c]pyridin-6-yl]thio}benzoic acid;
   4-(1-Ethyl-6-{[2-(methyloxy)phenyl]thio}-1H-imidazo[4,5-c]pyridin-2-yl)-furazan-3-amine;
   4-[1-Ethyl-6-(1H-imidazol-2-ylthio)-1H-imidazo[4,5-c]pyridin-2-yl]-furazan-3-amine;
   4-[6-(Cyclopentylthio)-1-ethyl-1H-imidazo[4,5-c]pyridin-2-yl]-furazan-3-amine;
   4-[1-Ethyl-6-(1,3-thiazol-2-ylthio)-1H-imidazo[4,5-c]pyridin-2-yl]-furazan-3-amine;
   4-{1-Ethyl-6-[(phenylmethyl)thio]-1H-imidazo[4,5-c]pyridin-2-yl}-furazan-3-amine;
   4-[1-Ethyl-6-(phenylthio)-1H-imidazo[4,5-c]pyridin-2-yl]-furazan-3-amine;
   methyl 2-{[2-(4-amino-furazan-3-yl)-1-ethyl-1H-imidazo[4,5-c]pyridin-6-yl]thio}benzoate;
   N-(4-{[2-(4-Amino-furazan-3-yl)-1-ethyl-1H-imidazo[4,5-c]pyridin-6-yl]thio}phenyl)acetamide;
   4-{6-[(3-Chloro-4-fluorophenyl)thio]-1-ethyl-1H-imidazo[4,5-c]pyridin-2-yl}-furazan-3-amine;
   4-{[2-(4-Amino-furazan-3-yl)-1-ethyl-1H-imidazo[4,5-c]pyridin-6-yl]thio}benzoic acid;
   N-(2-{[2-(4-Amino-furazan-3-yl)-1-ethyl-1H-imidazo[4,5-c]pyridin-6-yl]thio}ethyl)acetamide;
   4-{6-[(2,5-dimethyl-3-furanyl)thio]-1-ethyl-1H-imidazo[4,5-c]pyridin-2-yl}-furazan-3-amine;
   4-[1-Ethyl-6-(phenylsulfinyl)-1H-imidazo[4,5-c]pyridin-2-yl]-furazan-3-amine;
   4-{6-[(3,4-Dichlorophenyl)thio]-1-ethyl-1H-imidazo[4,5-c]pyridin-2-yl}-furazan-3-amine;
   4-[1-Ethyl-6-(2-pyridinylthio)-1H-imidazo[4,5-c]pyridin-2-yl]-furazan-3-amine;
   4-{1-Ethyl-6-[(4-fluorophenyl)thio]-1H-imidazo[4,5-c]pyridin-2-yl}-furazan-3-amine;
   7-{[2-(4-Amino-furazan-3-yl)-1-ethyl-1H-imidazo[4,5-c]pyridin-6-yl]thio}-3-methyl-2H-chromen-2-one;
   4-(1-Ethyl-6-{[4-(trifluoromethyl)phenyl]thio}-1H-imidazo[4,5-c]pyridin-2-yl)-furazan-3-amine;
   1-((2S)-3-{[2-(4-Amino-furazan-3-yl)-1-ethyl-1H-imidazo[4,5-c]pyridin-6-yl]thio}-2-methylpropanoyl)-L-proline;
   4-(1-Ethyl-6-{[4-(methylthio)phenyl]thio}-1H-imidazo[4,5-c]pyridin-2-yl)-furazan-3-amine;
   4-[1-Ethyl-6-(4-pyridinylthio)-1H-imidazo[4,5-c]pyridin-2-yl]-furazan-3-amine;
   4-[1-Ethyl-6-([1,3]thiazolo[4,5-b]pyridin-2-ylthio)-1H-imidazo[4,5-c]pyridin-2-yl]-furazan-3-amine;
   4-(1-Ethyl-6-{[5-(methyloxy)-1,3-benzothiazol-2-yl]thio}-1H-imidazo[4,5-c]pyridin-2-yl)-furazan-3-amine;
   Methyl (2E)-3-(4-{[2-(4-amino-furazan-3-yl)-1-ethyl-1H-imidazo[4,5-c]pyridin-6-yl]thio}phenyl)-2-propenoate;
   4-(1-Ethyl-6-{[4-(methylsulfonyl)phenyl]sulfinyl}-1H-imidazo[4,5-c]pyridin-2-yl)-furazan-3-amine;
   4-(1-Ethyl-6-{[4-(methylsulfinyl)phenyl]sulfinyl}-1H-imidazo[4,5-c]pyridin-2-yl)-furazan-3-amine;
   4-{6-[(4-Fluorophenyl)oxy]-1-phenyl-1H-imidazo[4,5-c]pyridin-2-yl}-furazan-3-amine;
   4-(1-Ethyl-6-{[3-(methyloxy)phenyl]oxy}-1H-imidazo[4,5-c]pyridin-2-yl)-furazan-3-amine;
   4-{6-[(3,4-Dimethylphenyl)oxy]-1-ethyl-1H-imidazo[4,5-c]pyridin-2-yl}-furazan-3-amine;
   N-(3-{[2-(4-Amino-furazan-3-yl)-1-phenyl-1H-imidazo[4,5-c]pyridin-6-yl]oxy}phenyl)acetamide;

4-{6-[(3-Aminophenyl)oxy]-1-phenyl-1H-imidazo[4,5-c]pyridin-2-yl}-furazan-3-amine;
4-{6-[(4-Aminophenyl)oxy]-1-phenyl-1H-imidazo[4,5-c]pyridin-2-yl}-furazan-3-amine;
3-{[2-(4-Amino-furazan-3-yl)-1-ethyl-1H-imidazo[4,5-c]pyridin-6-yl]oxy}benzonitrile;
1-(3-{[2-(4-Amino-furazan-3-yl)-1-ethyl-1H-imidazo[4,5-c]pyridin-6-yl]oxy}phenyl)ethanone;
N-(4-{[2-(4-Amino-furazan-3-yl)-1-phenyl-1H-imidazo[4,5-c]pyridin-6-yl]oxy}phenyl)acetamid;
4-(1-Ethyl-6-{[3-(1-methylethyl)phenyl]oxy}-1H-imidazo[4,5-c]pyridin-2-yl)-furazan-3-amine;
4-(6-{[3-(Dimethylamino)phenyl]oxy}-1-ethyl-1H-imidazo[4,5-c]pyridin-2-yl)-furazan-3-amine;
4-(1-Ethyl-6-{[3-(4-morpholinyl)phenyl]oxy}-1H-imidazo[4,5-c]pyridin-2-yl)-furazan-3-amine;
N-(3-{[2-(4-Amino-furazan-3-yl)-1-ethyl-1H-imidazo[4,5-c]pyridin-6-yl]oxy}phenyl)-4-methylbenzenesulfonamide;
4-(1-Ethyl-7-{[3-(methyloxy)phenyl]oxy}-1H-imidazo[4,5-c]pyridin-2-yl)-furazan-3-amine;
1,1-Dimethylethyl (3-{[2-(4-amino-furazan-3-yl)-1-ethyl-1H-imidazo[4,5-c]pyridin-6-yl]oxy}phenyl)carbamate;
4-{2-(4-Amino-furazan-3-yl)-6-[(4-fluorophenyl)oxy]-1H-imidazo[4,5-c]pyridin-1-yl}phenol;
4-{6-[(3-Aminophenyl)oxy]-1-ethyl-1H-imidazo[4,5-c]pyridin-2-yl}-furazan-3-amine;
N-(3-{[2-(4-Amino-furazan-3-yl)-1-ethyl-1H-imidazo[4,5-c]pyridin-6-yl]oxy}phenyl)methanesulfonamide;
N-(3-{[2-(4-Amino-furazan-3-yl)-1-(4-hydroxyphenyl)-1H-imidazo[4,5-c]pyridin-6-yl]oxy}phenyl)acetamide;
N-(3-{[2-(4-Amino-furazan-3-yl)-1-ethyl-1H-imidazo[4,5-c]pyridin-6-yl]oxy}phenyl)-N'-methylurea;
N-(3-{[2-(4-Amino-furazan-3-yl)-1-(4-{[2-(dimethylamino)ethyl]oxy}phenyl)-1H-imidazo[4,5-c]pyridin-6-yl]oxy}phenyl)acetamide;
N-(4-{[2-(4-Amino-furazan-3-yl)-1-(4-{[2-(dimethylamino)ethyl]oxy}phenyl)-1H-imidazo[4,5-c]pyridin-6-yl]oxy}phenyl)acetamide;
Methyl 4-{[2-(4-amino-furazan-3-yl)-1-ethyl-1H-imidazo[4,5-c]pyridin-6-yl]oxy}benzoate;
Methyl 3-{[2-(4-amino-furazan-3-yl)-1-ethyl-1H-imidazo[4,5-c]pyridin-6-yl]oxy}benzoate;
4-[6-[(4-Fluorophenyl)oxy]-1-(2-methyl-1,2,3,4-tetrahydro-7-isoquinolinyl)-1H-imidazo[4,5-c]pyridin-2-yl]-furazan-3-amine;
1-(3-{[2-(4-Amino-furazan-3-yl)-1-ethyl-1H-imidazo[4,5-c]pyridin-6-yl]oxy}phenyl)ethanol;
2-(3-{[2-(4-Amino-furazan-3-yl)-1-ethyl-1H-imidazo[4,5-c]pyridin-6-yl]oxy}phenyl)-2-butanol;
6-{[2-(4-Amino-furazan-3-yl)-1-ethyl-1H-imidazo[4,5-c]pyridin-6-yl]oxy}-3,4-dihydro-1(2H)-naphthalenone;
N-(3-{[2-(4-Amino-furazan-3-yl)-1-ethyl-1H-imidazo[4,5-c]pyridin-6-yl]oxy}phenyl)-N'-(phenylmethyl)urea;
Methyl (3-{[2-(4-amino-furazan-3-yl)-1-ethyl-1H-imidazo[4,5-c]pyridin-6-yl]oxy}phenyl)acetate;
(3-{[2-(4-Amino-furazan-3-yl)-1-ethyl-1H-imidazo[4,5-c]pyridin-6-yl]oxy}phenyl)acetic acid;
4-{[2-(4-Amino-furazan-3-yl)-1-ethyl-1H-imidazo[4,5-c]pyridin-6-yl]oxy}benzonitrile;
3-{[2-(4-Amino-furazan-3-yl)-1-ethyl-1H-imidazo[4,5-c]pyridin-6-yl]oxy}benzoic acid;
N-(3-{[2-(4-Amino-furazan-3-yl)-1-(4-{[2-(methylAmino)ethyl]oxy}phenyl)-1H-imidazo[4,5-c]pyridin-6-yl]oxy}phenyl)acetamide;
N-(3-{[1-{4-[(2-Aminoethyl)oxy]phenyl}-2-(4-amino-furazan-3-yl)-1H-imidazo[4,5-c]pyridin-6-yl]oxy}phenyl)acetamide;
N-[3-({2-(4-Amino-furazan-3-yl)-1-[4-({[(2S)-1-methyl-2-pyrrolidinyl]methyl}oxy)phenyl]-1H-imidazo[4,5-c]pyridin-6-yl}oxy)phenyl]acetamide;
N-(3-{[2-(4-Amino-furazan-3-yl)-1-ethyl-1H-imidazo[4,5-c]pyridin-6-yl]oxy}phenyl)-4-(methyloxy)benzamide;
N-(3-{[2-(4-Amino-furazan-3-yl)-1-ethyl-1H-imidazo[4,5-c]pyridin-6-yl]oxy}phenyl)-4-fluorobenzamide;
N-(3-{[2-(4-Amino-furazan-3-yl)-1-ethyl-1H-imidazo[4,5-c]pyridin-6-yl]oxy}phenyl)-2-furancarboxamide;
N-(3-{[2-(4-Amino-furazan-3-yl)-1-ethyl-1H-imidazo[4,5-c]pyridin-6-yl]oxy}phenyl)-2-methylpropanamide;
N-(3-{[2-(4-Amino-furazan-3-yl)-1-ethyl-1H-imidazo[4,5-c]pyridin-6-yl]oxy}phenyl)butanamide;
N-(3-{[2-(4-Amino-furazan-3-yl)-1-ethyl-1H-imidazo[4,5-c]pyridin-6-yl]oxy}phenyl)-2-(methyloxy)acetamide;
3-{[2-(4-Amino-furazan-3-yl)-1-ethyl-1H-imidazo[4,5-c]pyridin-6-yl]oxy}phenol;
Methyl 3-{[2-(4-amino-furazan-3-yl)-1-phenyl-1H-imidazo[4,5-c]pyridin-6-yl]oxy}benzoate;
3-{[2-(4-Amino-furazan-3-yl)-1-phenyl-1H-imidazo[4,5-c]pyridin-6-yl]oxy}benzoic acid;
N-(3-{[2-(4-Amino-furazan-3-yl)-1-ethyl-1H-imidazo[4,5-c]pyridin-6-yl]oxy}phenyl)-4-morpholinecarboxamide;
N-(3-{[2-(4-Amino-furazan-3-yl)-1-ethyl-1H-imidazo[4,5-c]pyridin-6-yl]oxy}phenyl)benzamide;
N-(3-{[2-(4-Amino-furazan-3-yl)-1-ethyl-1H-imidazo[4,5-c]pyridin-6-yl]oxy}phenyl)-4-fluorobenzenesulfonamide;
N-(4-{[2-(4-Amino-furazan-3-yl)-1-(4-hydroxyphenyl)-1H-imidazo[4,5-c]pyridin-6-yl]oxy}phenyl)acetamide;
3-{[2-(4-Amino-furazan-3-yl)-1-phenyl-1H-imidazo[4,5-c]pyridin-6-yl]oxy}-N,N-dimethylbenzamide;
3-{[2-(4-Amino-furazan-3-yl)-1-phenyl-1H-imidazo[4,5-c]pyridin-6-yl]oxy}-N-methylbenzamide;
3-{[2-(4-Amino-furazan-3-yl)-1-phenyl-1H-imidazo[4,5-c]pyridin-6-yl]oxy}benzamide;
4-(1-Phenyl-6-{[3-(1-piperidinylcarbonyl)phenyl]oxy}-1H-imidazo[4,5-c]pyridin-2-yl)-furazan-3-amine;
3-{[2-(4-Amino-furazan-3-yl)-1-phenyl-1H-imidazo[4,5-c]pyridin-6-yl]oxy}-N-ethylbenzamide;
N-(3-{[2-(4-Amino-furazan-3-yl)-1-ethyl-1H-imidazo[4,5-c]pyridin-6-yl]oxy}phenyl)-N-methylacetamide;
N-(3-{[2-(4-Amino-furazan-3-yl)-1-(1,2,3,4-tetrahydro-7-isoquinolinyl)-1H-imidazo[4,5-c]pyridin-6-yl]oxy}phenyl)acetamide;
3-{[2-(4-Amino-furazan-3-yl)-1-phenyl-1H-imidazo[4,5-c]pyridin-6-yl]oxy}-N-[2-(methyloxy)ethyl]benzamide;
3-{[2-(4-Amino-furazan-3-yl)-1-phenyl-1H-imidazo[4,5-c]pyridin-6-yl]oxy}-N-[2-(4-morpholinyl)ethyl]benzamide;
1-(3-{[2-(4-Amino-furazan-3-yl)-1-phenyl-1H-imidazo[4,5-c]pyridin-6-yl]oxy}phenyl)ethanone;
N-(3-{[2-(4-Amino-furazan-3-yl)-1-ethyl-1H-imidazo[4,5-c]pyridin-6-yl]oxy}phenyl)-N'-phenylurea;
N-(3-{[2-(4-Amino-furazan-3-yl)-1-ethyl-1H-imidazo[4,5-c]pyridin-6-yl]oxy}phenyl)-4-(methyloxy)benzenesulfonamide;
N'-(3-{[2-(4-Amino-furazan-3-yl)-1-ethyl-1H-imidazo[4,5-c]pyridin-6-yl]oxy}phenyl)-N,N-dimethylsulfamide;

N-(3-{[2-(4-Amino-furazan-3-yl)-1-ethyl-1H-imidazo[4,5-c]pyridin-6-yl]oxy}phenyl)-1-butanesulfonamide;

N-(3-{[2-(4-Amino-furazan-3-yl)-1-ethyl-1H-imidazo[4,5-c]pyridin-6-yl]oxy}phenyl)-3-pyridinecarboxamide;

4-{1-Athyl-6-[(phenylmethyl)oxy]-1H-imidazo[4,5-c]pyridin-2-yl}-furazan-3-amine;

N-(3-{[2-(4-Amino-furazan-3-yl)-1-(4-{[2-(dimethylAmino)ethyl]oxy}phenyl)-1H-imidazo[4,5-c]pyridin-6-yl]oxy}phenyl)methanesulfonamide;

4-{6-[(3-Nitrophenyl)oxy]-1-phenyl-1H-imidazo[4,5-c]pyridin-2-yl}-furazan-3-amine;

N-(3-{[2-(4-Amino-furazan-3-yl)-1-ethyl-1H-imidazo[4,5-c]pyridin-6-yl]oxy}phenyl)-4-cyanobenzamide;

N-(3-{[2-(4-Amino-furazan-3-yl)-1-ethyl-1H-imidazo[4,5-c]pyridin-6-yl]oxy}phenyl)cyclohexanecarboxamide;

N-(3-{[2-(4-Amino-furazan-3-yl)-1-ethyl-1H-imidazo[4,5-c]pyridin-6-yl]oxy}phenyl)-3-(methyloxy)benzamide;

N-(3-{[2-(4-Amino-furazan-3-yl)-1-ethyl-1H-imidazo[4,5-c]pyridin-6-yl]oxy}phenyl)-4-(dimethylamino)benzamide;

N-(3-{[2-(4-Amino-furazan-3-yl)-1-ethyl-1H-imidazo[4,5-c]pyridin-6-yl]oxy}phenyl)-4-(methyloxy)benzamide;

N-(3-{[2-(4-Amino-furazan-3-yl)-1-ethyl-1H-imidazo[4,5-c]pyridin-6-yl]oxy}phenyl)urea;

3-{[2-(4-Amino-furazan-3-yl)-1-phenyl-1H-imidazo[4,5-c]pyridin-6-yl]oxy}-N-(cyclopropylmethyl)benzamide;

3-{[2-(4-Amino-furazan-3-yl)-1-phenyl-1H-imidazo[4,5-c]pyridin-6-yl]oxy}-N-[(4-methyl-1,3-thiazol-2-yl)methyl]benzamide;

3-{[2-(4-Amino-furazan-3-yl)-1-phenyl-1H-imidazo[4,5-c]pyridin-6-yl]oxy}-N-[(1,5-dimethyl-1H-pyrazol-4-yl)methyl]benzamide;

3-{[2-(4-Amino-furazan-3-yl)-1-phenyl-1H-imidazo[4,5-c]pyridin-6-yl]oxy}-N-[3-(4-morpholinyl)propyl]benzamide;

4-[6-[(4-Fluorophenyl)oxy]-1-(1,2,3,4-tetrahydro-7-isoquinolinyl)-1H-imidazo[4,5-c]pyridin-2-yl]-furazan-3-amine;

4-[2-(4-Amino-furazan-3-yl)-6-bromo-1H-imidazo[4,5-c]pyridin-1-yl]phenol;

N-[5-{[2-(4-Amino-furazan-3-yl)-1-ethyl-1H-imidazo[4,5-c]pyridin-6-yl]thio}-2-(methyloxy)phenyl]acetamide;

1-(3-{[2-(4-Amino-furazan-3-yl)-1-ethyl-1H-imidazo[4,5-c]pyridin-6-yl]oxy}phenyl)-1-propanone;

3-{[2-(4-Amino-furazan-3-yl)-1-phenyl-1H-imidazo[4,5-c]pyridin-6-yl]oxy}-N-[3-(ethyloxy)propyl]benzamide;

N-(4-{2-(4-Amino-furazan-3-yl)-6-[(4-fluorophenyl)oxy]-1H-imidazo[4,5-c]pyridin-1-yl}phenyl)methanesulfonamide;

4-{1-[2-(Aminoacetyl)-1,2,3,4-tetrahydro-7-isoquinolinyl]-6-[(4-fluorophenyl)oxy]-1H-imidazo[4,5-c]pyridin-2-yl}-furazan-3-amine;

N-(3-{[2-(4-Amino-furazan-3-yl)-1-ethyl-1H-imidazo[4,5-c]pyridin-6-yl]oxy}phenyl)-4-(ethyloxy)benzamide;

N-(3-{[2-(4-Amino-furazan-3-yl)-1-ethyl-1H-imidazo[4,5-c]pyridin-6-yl]oxy}phenyl)-3-methylbutanamide;

4-({[(3-{[2-(4-Amino-furazan-3-yl)-1-ethyl-1H-imidazo[4,5-c]pyridin-6-yl]oxy}phenyl)Amino]carbonyl}amino)benzoic acid;

4-[6-Bromo-1-(4-{[2-(dimethylamino)ethyl]oxy}phenyl)-1H-imidazo[4,5-c]pyridin-2-yl]-furazan-3-amine;

2-[7-{2-(4-Amino-furazan-3-yl)-6-[(4-fluorophenyl)oxy]-1H-imidazo[4,5-c]pyridin-1-yl}-3,4-dihydro-2(1H)-isoquinolinyl]acetamide;

3-{[2-(4-Amino-furazan-3-yl)-1-ethyl-1H-imidazo[4,5-c]pyridin-6-yl]amino}benzenethiol;

2-(4-Amino-furazan-3-yl)-1-ethyl-N-(phenylmethyl)-1H-imidazo[4,5-c]pyridin-6-amine;

4-[6-[(4-fluorophenyl)oxy]-1-(4-{[2-(methylamino)ethyl]oxy}phenyl)-1H-imidazo[4,5-c]pyridin-2-yl]-furazan-3-amine;

4-{2-(4-amino-furazan-3-yl)-6-[(4-fluorophenyl)oxy]-1H-imidazo[4,5-c]pyridin-1-yl}-2-chlorophenol;

4-{1-(3-chloro-4-{[2-(dimethylamino)ethyl]oxy}phenyl)-6-[(4-fluorophenyl)oxy]-1H-imidazo[4,5-c]pyridin-2-yl}-furazan-3-amine;

3-{[2-(4-amino-furazan-3-yl)-1-(4-hydroxyphenyl)-1H-imidazo[4,5-c]pyridin-6-yl]oxy}-N-[2-(4-morpholinyl)ethyl]benzamide;

N-[2-(acetylamino)ethyl]-3-{[2-(4-amino-furazan-3-yl)-1-phenyl-1H-imidazo[4,5-c]pyridin-6-yl]oxy}benzamide;

3-{[2-(4-amino-furazan-3-yl)-1-phenyl-1H-imidazo[4,5-c]pyridin-6-yl]oxy}-N-(tetrahydro-2-furanylmethyl)benzamide;

3-{[2-(4-amino-furazan-3-yl)-1-phenyl-1H-imidazo[4,5-c]pyridin-6-yl]oxy}-N-[2-(dimethylamino)ethyl]benzamide;

3-{[2-(4-amino-furazan-3-yl)-1-phenyl-1H-imidazo[4,5-c]pyridin-6-yl]oxy}-N-[2-(1-methyl-1H-pyrrol-2-yl)ethyl]benzamide;

3-{[2-(4-amino-furazan-3-yl)-1-phenyl-1H-imidazo[4,5-c]pyridin-6-yl]oxy}-N-[2-(2-pyridinyl)ethyl]benzamide;

3-{[2-(4-amino-furazan-3-yl)-1-phenyl-1H-imidazo[4,5-c]pyridin-6-yl]oxy}-N-[3-(dimethylamino)propyl]benzamide;

4-[6-(1H-benzimidazol-4-yloxy)-1-phenyl-1H-imidazo[4,5-c]pyridin-2-yl]-furazan-3-amine;

N-(3-{[2-(4-amino-furazan-3-yl)-1-ethyl-1H-imidazo[4,5-c]pyridin-6-yl]oxy}phenyl)-6-methyl-3-pyridinecarboxamide;

N-(3-{[2-(4-amino-furazan-3-yl)-1-ethyl-1H-imidazo[4,5-c]pyridin-6-yl]oxy}phenyl)-2-methyl-3-pyridinecarboxamide;

4-{1-[4-(aminomethyl)phenyl]-6-[(4-fluorophenyl)oxy]-1H-imidazo[4,5-c]pyridin-2-yl}-furazan-3-amine;

3-{[2-(4-amino-furazan-3-yl)-1-phenyl-1H-imidazo[4,5-c]pyridin-6-yl]oxy}-N-[3-(1H-imidazol-1-yl)propyl]benzamide;

3-{[2-(4-amino-furazan-3-yl)-1-phenyl-1H-imidazo[4,5-c]pyridin-6-yl]oxy}-N-[2-(1-pyrrolidinyl)ethyl]benzamide;

3-{[2-(4-amino-furazan-3-yl)-1-phenyl-1H-imidazo[4,5-c]pyridin-6-yl]oxy}-N-[2-(4-hydroxyphenyl)ethyl]benzamide;

3-{[2-(4-amino-furazan-3-yl)-1-phenyl-1H-imidazo[4,5-c]pyridin-6-yl]oxy}-N-[2-(3-pyridinyl)ethyl]benzamide;

3-{[2-(4-amino-furazan-3-yl)-1-phenyl-1H-imidazo[4,5-c]pyridin-6-yl]oxy}-N-[2-(phenyloxy)ethyl]benzamide;

3-{[2-(4-amino-furazan-3-yl)-1-phenyl-1H-imidazo[4,5-c]pyridin-6-yl]oxy}-N-{2-[3,5-bis(methyloxy)phenyl]ethyl}benzamide;

3-{[2-(4-amino-furazan-3-yl)-1-phenyl-1H-imidazo[4,5-c]pyridin-6-yl]oxy}-N-[3-(2-oxo-1-pyrrolidinyl)propyl]benzamide;
3-{[2-(4-amino-furazan-3-yl)-1-phenyl-1H-imidazo[4,5-c]pyridin-6-yl]oxy}-N-(1,3-benzodioxol-5-ylmethyl)benzamide;
3-{[2-(4-amino-furazan-3-yl)-1-phenyl-1H-imidazo[4,5-c]pyridin-6-yl]oxy}-N-(1,4-dioxan-2-ylmethyl)benzamide;
3-{[2-(4-amino-furazan-3-yl)-1-phenyl-1H-imidazo[4,5-c]pyridin-6-yl]oxy}-N-(4-pyridinylmethyl)benzamide;
3-{[2-(4-amino-furazan-3-yl)-1-phenyl-1H-imidazo[4,5-c]pyridin-6-yl]oxy}-N-[3-(1-pyrrolidinyl)propyl]benzamide;
3-{[2-(4-amino-furazan-3-yl)-1-phenyl-1H-imidazo[4,5-c]pyridin-6-yl]oxy}-N-[3-(4-methyl-1-piperazinyl)propyl]benzamide;
3-{[2-(4-amino-furazan-3-yl)-1-phenyl-1H-imidazo[4,5-c]pyridin-6-yl]oxy}-N-[2-(4-pyridinyl)ethyl]benzamide;
3-{[2-(4-amino-furazan-3-yl)-1-phenyl-1H-imidazo[4,5-c]pyridin-6'-yl]oxy}-N-(2-cyanoethyl)benzamide;
N-(3-{[2-(4-amino-furazan-3-yl)-1-ethyl-1H-imidazo[4,5-c]pyridin-6-yl]oxy}-2-methylphenyl)acetamide;
7-{[2-(4-amino-furazan-3-yl)-1-ethyl-1H-imidazo[4,5-c]pyridin-6-yl]oxy}-4-methyl-2(1H)-quinolinone;
N-(3-{[2-(4-amino-furazan-3-yl)-1-ethyl-1H-imidazo[4,5-c]pyridin-6-yl]oxy}phenyl)-2-(dimethylamino)-5-pyrimidinecarboxamide;
N-(3-{[2-(4-amino-furazan-3-yl)-1-ethyl-1H-imidazo[4,5-c]pyridin-6-yl]oxy}phenyl)-2-(methyloxy)-3-pyridinecarboxamide;
N-(3-{[2-(4-amino-furazan-3-yl)-1-ethyl-1H-imidazo[4,5-c]pyridin-6-yl]oxy}phenyl)-4-(1-piperidinyl)benzamide;
N-(3-{[2-(4-amino-furazan-3-yl)-1-ethyl-1H-imidazo[4,5-c]pyridin-6-yl]oxy}phenyl)-4-(methyloxy)-3-(trifluoromethyl)benzamide;
N-(3-{[2-(4-amino-furazan-3-yl)-1-ethyl-1H-imidazo[4,5-c]pyridin-6-yl]oxy}phenyl)-3-fluoro-4-(methyloxy)benzamide;
N-(3-{[2-(4-amino-furazan-3-yl)-1-ethyl-1H-imidazo[4,5-c]pyridin-6-yl]oxy}phenyl)-3-chloro-4-(methyloxy)benzamide;
N-(3-{[2-(4-amino-furazan-3-yl)-1-ethyl-1H-imidazo[4,5-c]pyridin-6-yl]oxy}phenyl)-4-(4-morpholinyl)benzamide;
N-(3-{[2-(4-amino-furazan-3-yl)-1-ethyl-1H-imidazo[4,5-c]pyridin-6-yl]oxy}phenyl)-2-methyl-1,3-thiazole-5-carboxamide;
N-(3-{[2-(4-amino-furazan-3-yl)-1-ethyl-1H-imidazo[4,5-c]pyridin-6-yl]oxy}phenyl)-1-methyl-1H-1,2,3-benzotriazole-5-carboxamide;
N-(3-{[2-(4-amino-furazan-3-yl)-1-ethyl-1H-imidazo[4,5-c]pyridin-6-yl]oxy}phenyl)-4-methyl-3,4-dihydro-2H-1,4-benzoxazine-7-carboxamide;
N-(3-{[2-(4-amino-furazan-3-yl)-1-(1,2,3,4-tetrahydro-7-isoquinolinyl)-1H-imidazo[4,5-c]pyridin-6-yl]oxy}phenyl)-4-(methyloxy)benzamide;
N-[(3-{[2-(4-amino-furazan-3-yl)-1-phenyl-1H-imidazo[4,5-c]pyridin-6-yl]oxy}phenyl)carbonyl]-beta-alanine;
3-{[2-(4-amino-furazan-3-yl)-1-phenyl-1H-imidazo[4,5-c]pyridin-6-yl]oxy}-N-(3-amino-3-oxopropyl)benzamide;
N-[4-(aminomethyl)phenyl]-3-{[2-(4-amino-furazan-3-yl)-1-phenyl-1H-imidazo[4,5-c]pyridin-6-yl]oxy}benzamide;
4-[6-(1H-benzimidazol-5-yloxy)-1-ethyl-1H-imidazo[4,5-c]pyridin-2-yl]-furazan-3-amine;
N-(3-{[2-(4-amino-furazan-3-yl)-1-ethyl-1H-imidazo[4,5-c]pyridin-6-yl]oxy}phenyl)-4-{[2-(4-morpholinyl)ethyl]oxy}benzamide;
N-(3-{[2-(4-amino-furazan-3-yl)-1-ethyl-1H-imidazo[4,5-c]pyridin-6-yl]oxy}phenyl)pyrazolo[1,5-a]pyridine-3-carboxamide;
N-(3-{[2-(4-amino-furazan-3-yl)-1-ethyl-1H-imidazo[4,5-c]pyridin-6-yl]oxy}phenyl)-1-methyl-1H-imidazole-2-carboxamide;
N-(3-{[2-(4-amino-furazan-3-yl)-1-ethyl-1H-imidazo[4,5-c]pyridin-6-yl]oxy}phenyl)-6-[(2,2,2-trifluoroethyl)oxy]-3-pyridinecarboxamide;
N-(3-{[2-(4-amino-furazan-3-yl)-1-ethyl-1H-imidazo[4,5-c]pyridin-6-yl]oxy}phenyl)-4-(3,5-dimethyl-1H-pyrazol-1-yl)benzamide;
N-(3-{[2-(4-amino-furazan-3-yl)-1-ethyl-1H-imidazo[4,5-c]pyridin-6-yl]oxy}phenyl)-4-(trifluoromethyl)-3-pyridinecarboxamide;
4-[2-(4-amino-furazan-3-yl)-6-(methyloxy)-1H-imidazo[4,5-c]pyridin-1-yl]phenol;
N-(3-{[2-(4-amino-furazan-3-yl)-1-ethyl-1H-imidazo[4,5-c]pyridin-6-yl]oxy}phenyl)-4-(1H-imidazol-1-yl)benzamide;
N-(3-{[2-(4-amino-furazan-3-yl)-1-ethyl-1H-imidazo[4,5-c]pyridin-6-yl]oxy}phenyl)-6-(1H-pyrazol-1-yl)-3-pyridinecarboxamide;
4-[1-(4-{[2-(dimethylamino)ethyl]oxy}phenyl)-6-(methyloxy)-1H-imidazo[4,5-c]pyridin-2-yl]-furazan-3-amine;
N-(3-{[2-(4-amino-furazan-3-yl)-1-ethyl-1H-imidazo[4,5-c]pyridin-6-yl]oxy}phenyl)-4-{[2-(dimethylamino)ethyl]oxy}benzamide;
N-(3-{[2-(4-amino-furazan-3-yl)-1-ethyl-1H-imidazo[4,5-c]pyridin-6-yl]oxy}phenyl)-1-methyl-4-piperidinecarboxamide;
4-{2-(4-amino-furazan-3-yl)-6-[(3-aminophenyl)oxy]-1H-imidazo[4,5-c]pyridin-1-yl}phenyl 4-(methyloxy)benzoate;
N-(3-{[2-(4-amino-furazan-3-yl)-1-(4-hydroxyphenyl)-1H-imidazo[4,5-c]pyridin-6-yl]oxy}phenyl)-4-(dimethylamino)butanamide;
4-{2-(4-amino-furazan-3-yl)-6-[(3-aminophenyl)oxy]-1H-imidazo[4,5-c]pyridin-1-yl}phenyl 2-methylpropanoate;
N'-(3-{[2-(4-amino-furazan-3-yl)-1-(4-hydroxyphenyl)-1H-imidazo[4,5-c]pyridin-6-yl]oxy}phenyl)-N,N-dimethylsulfamide;
N-(3-{[2-(4-amino-furazan-3-yl)-1-(4-{[2-(dimethylamino)ethyl]oxy}phenyl)-1H-imidazo[4,5-c]pyridin-6-yl]oxy}phenyl)-4-(methyloxy)benzamide;
N-(3-{[2-(4-amino-furazan-3-yl)-1-(4-hydroxyphenyl)-1H-imidazo[4,5-c]pyridin-6-yl]oxy}phenyl)methanesulfonamide;
N-(3-{[2-(4-amino-furazan-3-yl)-1-ethyl-1H-imidazo[4,5-c]pyridin-6-yl]oxy}phenyl)-3,4-bis(methyloxy)benzamide;
N-(3-{[2-(4-amino-furazan-3-yl)-1-ethyl-1H-imidazo[4,5-c]pyridin-6-yl]oxy}phenyl)-2,3-dihydro-1-benzofuran-5-carboxamide;
N-(3-{[2-(4-amino-furazan-3-yl)-1-ethyl-1H-imidazo[4,5-c]pyridin-6-yl]oxy}phenyl)-4-chloro-2-pyridinecarboxamide;

N-(3-{[2-(4-amino-furazan-3-yl)-1-(4-{[2-(dimethylamino)ethyl]oxy}phenyl)-1H-imidazo[4,5-c]pyridin-6-yl]oxy}phenyl)-6-methyl-3-pyridinecarboxamide;

N-(3-{[2-(4-amino-furazan-3-yl)-1-ethyl-1H-imidazo[4,5-c]pyridin-6-yl]oxy}phenyl)-4-(dimethylamino)butanamide;

5-{[2-(4-amino-furazan-3-yl)-1-ethyl-1H-imidazo[4,5-c]pyridin-6-yl]oxy}-1,3-dimethyl-1,3-dihydro-2H-benzimidazol-2-one;

3-{[2-(4-amino-furazan-3-yl)-1-(4-fluorophenyl)-1H-imidazo[4,5-c]pyridin-6-yl]oxy}-N-[2-(4-morpholinyl)ethyl]benzamide;

3-{[2-(4-amino-furazan-3-yl)-1-(4-fluorophenyl)-1H-imidazo[4,5-c]pyridin-6-yl]oxy}-N-[3-(4-methyl-1-piperazinyl)propyl]benzamide;

3({2-(4-amino-furazan-3-yl)-1-[4-(trifluoromethyl)phenyl]-1H-imidazo[4,5-c]pyridin-6-yl}oxy)-N-[2-(4-morpholinyl)ethyl]benzamide;

3-({2-(4-amino-furazan-3-yl)-1-[4-(trifluoromethyl)phenyl]-1H-imidazo[4,5-c]pyridin-6-yl}oxy)-N-[3-(4-methyl-1-piperazinyl)propyl]benzamide;

N'-(3-{[2-(4-amino-furazan-3-yl)-1-(4-{[2-(dimethylamino)ethyl]oxy}phenyl)-1H-imidazo[4,5-c]pyridin-6-yl]oxy}phenyl)-N,N-dimethylsulfamide;

N-(3-{[2-(4-amino-furazan-3-yl)-1-(4-{[2-(dimethylamino)ethyl]oxy}phenyl)-1H-imidazo[4,5-c]pyridin-6-yl]oxy}phenyl)-2-methylpropanamide;

methyl 3-{[2-(4-amino-furazan-3-yl)-1-(phenylmethyl)-1H-imidazo[4,5-c]pyridin-6-yl]oxy}benzoate;

3-{[2-(4-amino-furazan-3-yl)-1-(phenylmethyl)-1H-imidazo[4,5-c]pyridin-6-yl]oxy}benzoic acid;

3-{[2-(4-amino-furazan-3-yl)-1-(phenylmethyl)-1H-imidazo[4,5-c]pyridin-6-yl]oxy}-N-[2-(4-morpholinyl)ethyl]benzamide;

N-(3-{[2-(4-amino-furazan-3-yl)-1-(4-{[2-(dimethylamino)ethyl]oxy}phenyl)-1H-imidazo[4,5-c]pyridin-6-yl]oxy}phenyl)-N'-methylurea;

3-{[2-(4-amino-furazan-3-yl)-1-(4-fluorophenyl)-1H-imidazo[4,5-c]pyridin-6-yl]oxy}-N-[3-(2-oxo-1-pyrrolidinyl)propyl]benzamide;

3-({2-(4-amino-furazan-3-yl)-1-[4-(trifluoromethyl)phenyl]-1H-imidazo[4,5-c]pyridin-6-yl}oxy)-N-[3-(2-oxo-1-pyrrolidinyl)propyl]benzamide;

3-{[2-(4-amino-furazan-3-yl)-1-phenyl-1H-imidazo[4,5-c]pyridin-6-yl]oxy}-N-{[4-(methyloxy)phenyl]methyl}benzamide;

3-{[2-(4-amino-furazan-3-yl)-1-phenyl-1H-imidazo[4,5-c]pyridin-6-yl]oxy}-N-[4-(methyloxy)phenyl]benzamide;

3-{[2-(4-amino-furazan-3-yl)-1-phenyl-1H-imidazo[4,5-c]pyridin-6-yl]oxy}-N-[4-(dimethylamino)phenyl]benzamide;

3-{[2-(4-amino-furazan-3-yl)-1-phenyl-1H-imidazo[4,5-c]pyridin-6-yl]oxy}-N-[3-(dimethylamino)phenyl]benzamide;

N-(3-{[2-(4-amino-furazan-3-yl)-1-phenyl-1H-imidazo[4,5-c]pyridin-6-yl]oxy}phenyl)-4-(dimethylamino)benzamide;

N-(3-{[2-(4-amino-furazan-3-yl)-1-phenyl-1H-imidazo[4,5-c]pyridin-6-yl]oxy}phenyl)-4-(methyloxy)benzamide;

3-{[2-(4-amino-furazan-3-yl)-1-ethyl-1H-imidazo[4,5-c]pyridin-6-yl]oxy}-N-[3-(2-oxo-1-pyrrolidinyl)propyl]benzamide;

3-{[2-(4-amino-furazan-3-yl)-1-ethyl-1H-imidazo[4,5-c]pyridin-6-yl]oxy}-N-[2-(4-morpholinyl)ethyl]benzamide;

3-{[2-(4-amino-furazan-3-yl)-1-ethyl-1H-imidazo[4,5-c]pyridin-6-yl]oxy}-N-[3-(4-methyl-1-piperazinyl)propyl]benzamide;

4-(aminomethyl)-N-(3-{[2-(4-amino-furazan-3-yl)-1-ethyl-1H-imidazo[4,5-c]pyridin-6-yl]oxy}phenyl)benzamide;

N-(3-{[2-(4-amino-furazan-3-yl)-1-ethyl-1H-imidazo[4,5-c]pyridin-6-yl]oxy}phenyl)-3-(3-pyridinyl)propanamide;

4-(aminomethyl)-N-(3-{[2-(4-amino-furazan-3-yl)-1-phenyl-1H-imidazo[4,5-c]pyridin-6-yl]oxy}phenyl)benzamide;

methyl 3-{[2-(4-amino-furazan-3-yl)-1H-imidazo[4,5-c]pyridin-6-yl]oxy}benzoate;

3-{[2-(4-amino-furazan-3-yl)-1-ethyl-1H-imidazo[4,5-c]pyridin-6-yl]oxy}-N-[4-(dimethylamino)phenyl]benzamide;

3-{[2-(4-amino-furazan-3-yl)-1-ethyl-1H-imidazo[4,5-c]pyridin-6-yl]oxy}-N-[4-(4-morpholinyl)phenyl]benzamide;

3-{[2-(4-amino-furazan-3-yl)-1-ethyl-1H-imidazo[4,5-c]pyridin-6-yl]oxy}-N-[4-(methyloxy)phenyl]benzamide;

N-(3-{[2-(4-amino-furazan-3-yl)-1-phenyl-1H-imidazo[4,5-c]pyridin-6-yl]oxy}phenyl)-3-(4-morpholinyl)propanamide;

3-({2-(4-amino-furazan-3-yl)-1-[2-(4-morpholinyl)ethyl]-1H-imidazo[4,5-c]pyridin-6-yl}oxy)benzoic acid;

3-({2-(4-amino-furazan-3-yl)-1-[2-(4-morpholinyl)ethyl]-1H-imidazo[4,5-c]pyridin-6-yl}oxy)-N-[3-(2-oxo-1-pyrrolidinyl)propyl]benzamide;

3-({2-(4-amino-furazan-3-yl)-1-[2-(4-morpholinyl)ethyl]-1H-imidazo[4,5-c]pyridin-6-yl}oxy)-N-[3-(4-methyl-1-piperazinyl)propyl]benzamide;

4-{1-ethyl-6-[(3-{[3-(4-morpholinyl)propyl]oxy}phenyl)oxy]-1H-imidazo[4,5-c]pyridin-2-yl}-furazan-3-amine;

1-{3-[(3-{[2-(4-amino-furazan-3-yl)-1-ethyl-1H-imidazo[4,5-c]pyridin-6-yl]oxy}phenyl)oxy]propyl}-2-pyrrolidinone;

4-{6-[(3-{[3-(4-acetyl-1-piperazinyl)propyl]oxy}phenyl)oxy]-1-ethyl-1H-imidazo[4,5-c]pyridin-2-yl}-furazan-3-amine;

1-(3-{[2-(4-amino-furazan-3-yl)-1-ethyl-1H-imidazo[4,5-c]pyridin-6-yl]oxy}phenyl)-4-(4-morpholinyl)-1-butanone;

3-{[2-(4-amino-furazan-3-yl)-1H-imidazo[4,5-c]pyridin-6-yl]oxy}-N-[2-(4-morpholinyl)ethyl]benzamide;

3-({2-(4-amino-furazan-3-yl)-1-[2-(methyloxy)phenyl]-1H-imidazo[4,5-c]pyridin-6-yl}oxy)-N-[3-(2-oxo-1-pyrrolidinyl)propyl]benzamide;

3-({2-(4-amino-furazan-3-yl)-1-[2-(methyloxy)phenyl]-1H-imidazo[4,5-c]pyridin-6-yl}oxy)-N-[3-(4-methyl-1-piperazinyl)propyl]benzamide;

3-({2-(4-amino-furazan-3-yl)-1-[2-(methyloxy)phenyl]-1H-imidazo[4,5-c]pyridin-6-yl}oxy)-N-[2-(4-morpholinyl)ethyl]benzamide;

3-{[2-(4-amino-furazan-3-yl)-1-ethyl-1H-imidazo[4,5-c]pyridin-6-yl]oxy}-N-(4-{[2-(4-morpholinyl)ethyl]oxy}phenyl)benzamide;

3-{[2-(4-amino-furazan-3-yl)-1-phenyl-1H-imidazo[4,5-c]pyridin-6-yl]oxy}-N-[2-(4-morpholinyl)ethyl]benzenesulfonamide;

N-(3-{[2-(4-amino-furazan-3-yl)-1-ethyl-1H-imidazo[4,5-c]pyridin-6-yl]oxy}phenyl)-3-(3-hydroxyphenyl)propanamide;

N-(3-{[2-(4-amino-furazan-3-yl)-1-ethyl-1H-imidazo[4,5-c]pyridin-6-yl]oxy}phenyl)-3-(4-hydroxyphenyl)propanamide;

N-(3-{[2-(4-amino-furazan-3-yl)-1-ethyl-1H-imidazo[4,5-c]pyridin-6-yl]oxy}phenyl)-4-(2-oxo-1-pyrrolidinyl)butanamide;

3-({2-(4-amino-furazan-3-yl)-1-[2-(methyloxy)ethyl]-1H-imidazo[4,5-c]pyridin-6-yl}oxy)-N-[3-(2-oxo-1-pyrrolidinyl)propyl]benzamide;

3-({2-(4-amino-furazan-3-yl)-1-[2-(methyloxy)ethyl]-1H-imidazo[4,5-c]pyridin-6-yl}oxy)-N-[2-(4-morpholinyl)ethyl]benzamide;

3-{[2-(4-amino-furazan-3-yl)-1-ethyl-1H-imidazo[4,5-c]pyridin-6-yl]oxy}-N-{2-[4-hydroxy-3-(methyloxy)phenyl]ethyl}benzamide;

N-(3-{[2-(4-amino-furazan-3-yl)-1-phenyl-1H-imidazo[4,5-c]pyridin-6-yl]oxy}phenyl)-3-(2-oxo-1-pyrrolidinyl)propanamide;

N-(3-{[2-(4-amino-furazan-3-yl)-1-phenyl-1H-imidazo[4,5-c]pyridin-6-yl]oxy}phenyl)-4-(2-oxo-1-pyrrolidinyl)butanamide;

3-{[2-(4-amino-furazan-3-yl)-1-(cyclopropylmethyl)-1H-imidazo[4,5-c]pyridin-6-yl]oxy}-N-[2-(4-morpholinyl)ethyl]benzamide;

3-{[2-(4-amino-furazan-3-yl)-1-ethyl-1H-imidazo[4,5-c]pyridin-6-yl]oxy}-N-(4-piperidinylmethy)benzamide;

3-{[2-(4-amino-furazan-3-yl)-1-ethyl-1H-imidazo[4,5-c]pyridin-6-ly]oxy}-N-[2-(4-piperidinyl)ethyl]benzamide;

N-(3-{[2-(4-amino-furazan-3-yl)-1-phenyl-1H-imidazo[4,5-c]pyridin-6-yl]oxy}phenyl)-4-{[2-(4-morpholiny)ethyl]oxy}benzamide;

N-[2-(4-acetyl-1-piperazinyl)ethyl]-3-{[2-(4-amino-furazan-3-yl)-1-ethyl-1-H-imidazo[4,5-c]pyridin-6-yl]oxy}benzamide;

3-{[2-(4-amino-furazan-3-yl)-1-ethyl-1H-imidazo[4,5-c]pyridin-6-yl]oxy}-N-[3-(4-methyl-1-piperazinyl)-3-oxopropyl]benzamide;

3-{[2-(4-amino-furazan-3-yl)-1-ethyl-1H-imidazo[4,5-c]pyridin-6-yl]oxy}-N-(4-{[2-(dimethylamino)ethyl]oxy}phenyl)benzamide; and N-(3-{[2-(4-amino-furazan-3-yl)-1-(cyclopropylmethyl)-1H-imidazo[4,5-c]pyridin-6-yl]oxy}phenyl)-4-{[2-(4-morpholinyl)ethyl]oxy}benzamide.

2. A compound which is N-(3-{[2-(4-amino-furazan-3-yl)-1-ethyl-1H-imidazo [4,5-c]pyridin-6-yl]oxy}phenyl)-4-{[2-(4-morpholinyl)ethyl]oxy}benzamide.

\* \* \* \* \*